US008623887B2

(12) United States Patent
Zahn et al.

(10) Patent No.: US 8,623,887 B2
(45) Date of Patent: *Jan. 7, 2014

(54) COMPOUNDS

(75) Inventors: Stephan Karl Zahn, Vienna (AT); Bojan Bister, Vienna (AT); Guido Boehmelt, Gaaden (AT); Ulrich Guertler, Vienna (AT); Andreas Mantoulidis, Vienna (AT); Ulrich Reiser, Vienna (AT); Andreas Schoop, Vienna (AT); Flavio Solca, Vienna (AT); Ulrike Tontsch-Grunt, Baden (AT); Matthias Treu, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1278 days.

This patent is subject to a terminal disclaimer.

(21) Appl. No.: 11/747,337

(22) Filed: May 11, 2007

(65) Prior Publication Data

US 2009/0163467 A1 Jun. 25, 2009

(30) Foreign Application Priority Data

May 15, 2006 (EP) .................................... 06113967

(51) Int. Cl.
*A61K 31/505* (2006.01)
*C07D 239/02* (2006.01)
*C07D 211/56* (2006.01)
*C07D 211/98* (2006.01)

(52) U.S. Cl.
USPC ............ 514/275; 514/329; 544/330; 546/244

(58) Field of Classification Search
USPC .................... 514/275, 329; 544/330; 546/244
See application file for complete search history.

(56) References Cited

U.S. PATENT DOCUMENTS

| 6,593,326 | B1 | 7/2003 | Bradbury et al. |
| 7,241,769 | B2 | 7/2007 | Stadtmueller et al. |
| 7,521,457 | B2 | 4/2009 | Stadtmueller et al. |
| 2003/0114472 | A1 | 6/2003 | De Corte et al. |
| 2004/0039005 | A1 | 2/2004 | De Corte et al. |
| 2004/0224966 | A1 | 11/2004 | Brumby et al. |
| 2005/0090493 | A1 | 4/2005 | Breault et al. |
| 2005/0113398 | A1 | 5/2005 | Argade et al. |
| 2006/0035891 | A1 | 2/2006 | Li et al. |
| 2007/0032514 | A1 | 2/2007 | Zahn et al. |

FOREIGN PATENT DOCUMENTS

| CA | 2 565 568 A1 | 12/2005 |
| CA | 2 573 371 A1 | 3/2006 |
| EP | 1 598 343 A1 | 11/2005 |
| WO | 0012485 A1 | 3/2000 |
| WO | 0027825 A1 | 5/2000 |
| WO | 01/72717 A1 | 10/2001 |
| WO | 02/04429 A1 | 1/2002 |
| WO | 0204429 A1 | 1/2002 |
| WO | 2004/014382 A1 | 2/2004 |
| WO | 2004074244 A2 | 9/2004 |
| WO | 2004080980 A1 | 9/2004 |
| WO | 2006/021544 A1 | 3/2006 |
| WO | 2007/003596 A1 | 1/2007 |

OTHER PUBLICATIONS

King, F.D. (Ed.), "Bioisosteres, conformational restriction and pro-drugs—case history: an example of a conformational restriction approach," Medical Chemistry: Principles and Practice, 1994, Chapter 14, 206-209.*
Dar AA, Goff LW, Majid S, Berlin J, El-Rifai W. Aurora kinase inhibitors—rising stars in cancer therapeutics? Mol Cancer Ther. Feb. 2010; 9(2): 268-78. Epub Feb. 2, 2010.*
Calabresi P and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
Hrabakova R, Kollareddy M, Tyleckova J, Halada P, Hajduch M, Gadher SJ, Kovarova H. InCancer cell resistance to aurora kinase inhibitors: identification of novel targets for cancer therapy. J Proteome Res. Jan. 4, 2013; 12(1): 455-69. Epub Dec. 10, 2012.*
Song J, Lei FT, Xiong X, Hague R. Intracellular signals of T cell costimulation. Cell Mol Immunol. Aug. 2008; 5(4): 239-47.*
Eniko Forro et al; Lipase-Catalized Enantioselective Ting Opening of Unactivated Alicyclic-Fused Beta-Lactams in an Organic Solvent; Organic Letters (2003) vol. 5 No. 8 pp. 1209-1212.
International Search Report for PCT/EP2007/054723 mailed on Oct. 10, 2007.
Cecil Textbook of Medicine, edited by Bennet, J.C., and Plum, F., 20th edition; vol. 1; 1996; pp. 1004-1010.

(Continued)

*Primary Examiner* — Paul Zarek
(74) *Attorney, Agent, or Firm* — Michael P. Morris; Mary-Ellen M. Devlin

(57) ABSTRACT

The present invention encompasses compounds of general formula (1)

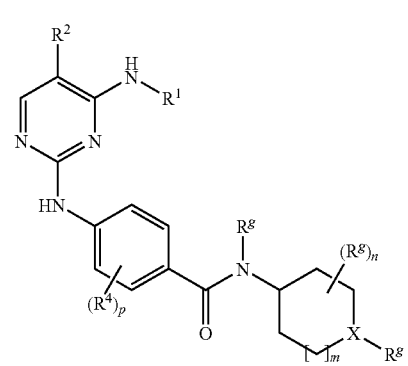

(1)

wherein
$R^1$, $R^2$, $R^4$, $R^g$, X, m, n and p are defined as in claim 1, which are suitable for the treatment of diseases characterized by excessive or abnormal cell proliferation, and their use for preparing a pharmaceutical composition having the above-mentioned properties.

15 Claims, No Drawings

(56) References Cited

OTHER PUBLICATIONS

Ahmad; Polo-like kinase (Plk) 1: a novel target for the treatment of prostate cancer; FASB Journal 18; 2004; pp. 5-7.
Turner et al.; Recent Advances in the Medicinal Chemistry of Antifungal Agents; Current Pharmaceutical Design; 1996; No. 2; pp. 209-224.
Sugar et al.; Comparison of Three Methods of Antifungal Susceptibility Testing with the Proposed NCCLS Standard Broth Macrodilution Assay: Lack of Effect of Phenol Red; Diagn. Microbiol. Infect. Dis; 1995; vol. 21; pp. 129-133.
Snyder et al.; Common bacteria whose susceptibility to antimicrobials is no longer predictable; J. Med. Liban; 2000; vol. 48(4); pp. 208-214.

* cited by examiner

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Pro Leu Glu Arg Arg Leu Ser Leu Val Pro Asp Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Pro Leu Glu Arg Arg Leu Ser Leu Val Pro Lys Met
1               5                   10

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Arg Arg Trp Ser Leu Gly Leu Arg Arg Trp Ser Leu Gly Leu Arg
1               5                   10                  15

Arg Trp Ser Leu Gly Leu Arg Arg Trp Ser Leu Gly
            20                  25
```

COMPOUNDS

The present invention relates to new compounds of general formula (1)

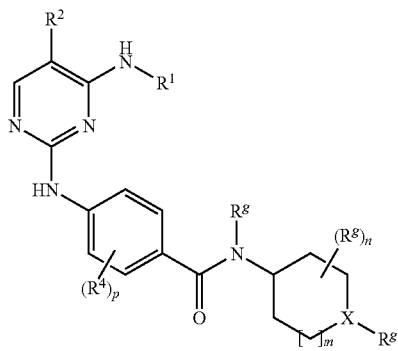

wherein the groups $R^1$, $R^2$, $R^4$, $R^g$, X, m, n and p have the meanings given in the claims and specification, the isomers thereof, processes for preparing these pyrimidines and their use as pharmaceutical compositions.

The aim of the present invention is to indicate new active substances which can be used for the prevention and/or treatment of diseases characterised by excessive or abnormal cell proliferation.

DETAILED DESCRIPTION OF THE INVENTION

It has now been found that, surprisingly, compounds of general formula (1), wherein the groups $R^1$, $R^2$, $R^4$, $R^g$, X, m, n and p have the meanings given hereinafter act as inhibitors of specific cell cycle kinases. Thus, the compounds according to the invention may be used for example for the treatment of diseases connected with the activity of specific cell cycle kinases and characterised by excessive or abnormal cell proliferation.

The present invention relates to compounds of general formula (1)

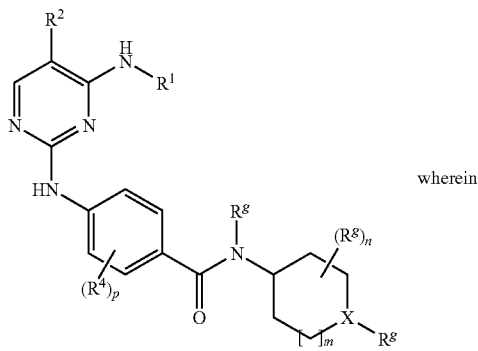

wherein

X denotes N or CH, and $R^1$ denotes $C_{3-10}$cycloalkyl, substituted by $R^3$ and optionally by one or more $R^4$, and $R^2$ denotes a group selected from among hydrogen, halogen, —CN, —$NO_2$, $C_{1-4}$alkyl, $C_{1-4}$haloalkyl, $C_{3-10}$cycloalkyl, $C_{4-16}$cycloalkylalkyl and $C_{7-16}$arylalkyl, and $R^3$ denotes a suitable group selected from among —C(O)$R^c$, —C(O)O$R^c$, —C(O)N$R^cR^c$, —S(O)$_2R^c$, —N($R^f$)S(O)$_2R^c$, —N($R^f$)C(O)$R^c$, —N($R^f$)C(O)O$R^c$, and —N($R^f$)C(O)N$R^cR^c$, and $R^4$ denotes a group selected from among $R^a$, $R^b$ and $R^a$ substituted by one or more identical or different $R^c$ and/or $R^b$, and each $R^a$ independently of one another is selected from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each $R^b$ denotes a suitable group and each is independently selected from among =O, —O$R^c$, $C_{1-3}$haloalkyloxy, —O$CF_3$, =S, —S$R^c$, =N$R^c$, =NO$R^c$, —N$R^cR^c$, halogen, —$CF_3$, —CN, —NC, —OCN, —SCN, —$NO_2$, —S(O)$R^c$, —S(O)$_2R^c$, —S(O)$_2$O$R^c$, —S(O)N$R^cR^c$, —S(O)$_2$N$R^cR^c$, —OS(O)$R^c$, —OS(O)$_2R^c$, —OS(O)$_2$O$R^c$, —OS(O)$_2$N$R^cR^c$, —C(O)$R^c$, —C(O)O$R^c$, —C(O)N$R^cR^c$, —CN($R^f$)N$R^cR^c$, —CN(OH)$R^c$, —CN(OH)N$R^cR^c$, —OC(O)$R^c$, —OC(O)O$R^c$, —OC(O)N$R^cR^c$, —OCN($R^f$)N$R^cR^c$, —N($R^f$)C(O)$R^c$, —N($R^f$)C(S)$R^c$, —N($R^f$)S(O)$_2R^c$, —N($R^f$)C(O)O$R^c$, —N($R^f$)C(O)N$R^cR^c$, —[N($R^f$)C(O)]$_2R^c$, —N[C(O)]$_2R^c$, —N[C(O)]$_2$O$R^c$, —[N($R^f$)C(O)]$_2$O$R^c$ and —N($R^f$)CN($R^f$)N$R^cR^c$, and each $R^c$ independently of one another denotes hydrogen or a group optionally substituted by one or more identical or different $R^d$ and/or $R^e$ selected from among $C_{1-6}$alkyl, $C_{3-10}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each $R^d$ independently of one another denotes hydrogen or a group optionally substituted by one or more identical or different $R^e$ and/or $R^f$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each $R^e$ is a suitable group and each is independently selected from among =O, —O$R^f$, $C_{1-3}$haloalkyloxy, —O$CF_3$, =S, —S$R^f$, =N$R^f$, =NO$R^f$, —N$R^fR^f$, halogen, —$CF_3$, —CN, —NC, —OCN, —SCN, —$NO_2$, —S(O)$R^f$, —S(O)$_2R^f$, —S(O)$_2$O$R^f$, —S(O)N$R^fR^f$, —S(O)$_2$N$R^fR^f$, —OS(O)$R^f$, —OS(O)$_2R^f$, —OS(O)$_2$O$R^f$, —OS(O)$_2$N$R^fR^f$, —C(O)$R^f$, —C(O)O$R^f$, —C(O)N$R^fR^f$, —CN($R^g$)N$R^fR^f$, —CN(OH)$R^f$, —C(NOH)N$R^fR^f$, —OC(O)$R^f$, —OC(O)O$R^f$, —OC(O)N$R^fR^f$, —OCN($R^g$)N$R^fR^f$, —N($R^g$)C(O)$R^f$, —N($R^g$)C(S)$R^f$, —N($R^g$)S(O)$_2R^f$, —N($R^d$)C(O)O$R^f$, —N($R^g$)C(O)N$R^f R^f$, and —N($R^g$)CN($R^f$)N$R^fR^f$, and each $R^f$ independently of one another denotes hydrogen or a group optionally substituted by one or more identical or different $R^g$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each $R^g$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkyl, 5-12 membered heteroaryl and 6-18 membered heteroarylalkyl, and m denotes 0 or 1, and n denotes 0, 1, 2, 3 or 4, and p denotes 0, 1 or 2, optionally in the form of the tautomers, the racemates, the enantiomers, the diastereomers and the mixtures thereof, and optionally the pharmacologically acceptable acid addition salts thereof, with the proviso that the following compounds 4-[4-((1R,2S)-2-isopropylcarbamoyl-cyclopentylamino)-5-trifluoromethyl-pyrimidin-2-ylamino]-N-(1-methyl-piperidin-4-yl)-benzamide, 4-[4-((1R,2S)-2-isopropylcarbamoyl-cyclopentylamino)-5-trifluoromethyl-pyrimidin-2-ylamino]-N-piperidin-4-yl-benzamide, 2-fluoro-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide, 2-chloro-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide, 2-fluoro-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide 4-[4-((1R,2S)-2-carbamoyl-cyclopentylamino)-5-methyl-pyrimidin-2-ylamino]-N-(1-methyl-piperidin-4-yl)-benzamide, 4-[4-((1R,2S)-2-carbamoyl-cyclopentylamino)-5-nitro-pyrimidin-2-ylamino]-N-(1-methyl-piperidin-4-yl)-benzamide, 4-[4-((1R,2S)-2-carbamoyl-cyclopentylamino)-5-fluoro-pyrimidin-2-ylamino]-N-(1-methyl-piperidin-4-yl)-benzamide, 4-[4-((1R,2S)-2-carbamoyl-cyclopentylamino)-5-chloro-pyrimidin-2-ylamino]-N-(1-methyl-piperidin-4-yl)-benzamide, 4-[4-((1R,2S)-2-carbamoyl-cyclopentylamino)-5-isopropyl-pyrimidin-2-ylamino]-N-(1-methyl-piperidin-4-yl)-benzamide, 4-[5-bromo-4-((1R,2S)-2-carbamoyl-cyclopentylamino)-pyrimidin-2-ylamino]-N-(1-methyl-piperidin-4-yl)-benzamide, 4-[4-((1R,2S)-2-carbamoyl-cyclopentylamino)-5-iodo-pyrimidin-2-ylamino]-N-(1-methyl-piperidin-4-yl)-benzamide, N-methyl-N-(1-methyl-piperidin-4-yl)-4-{4-[(1R,2S)-2-(pyrrolidine-1-carbonyl)-cyclopentylamino]-5-trifluoromethyl-pyrimidin-2-ylamino}-benzamide, 4-[4-((1R,2S)-2-cyclopentylcarbamoyl-cyclopentylamino)-5-trifluoromethyl-pyrimidin-2-ylamino]-N-methyl-N-(1-methyl-piperidin-4-yl)-benzamide, 4-{4-[(1R,2S)-2-(1,1-dioxo-tetrahydro-1$\lambda^6$-thiophen-3-yl-carbamoyl)-cyclopentylamino]-5-trifluoromethyl-pyrimidin-2-ylamino}-N-methyl-N-(1-methyl-piperidin-4-yl)-benzamide, N-methyl-N-(1-methyl-piperidin-4-yl)-4-{4-[(1R,2S)-2-(2,2,2-trifluoro-ethylcarbamoyl)-cyclopentylamino]-5-trifluoromethyl-pyrimidin-2-ylamino}-benzamide, N-methyl-4-{4-[(1R,2S)-2-(3-methyl-butylcarbamoyl)-cyclopentylamino]-5-trifluoromethyl-pyrimidin-2-ylamino}-N-(1-methyl-piperidin-4-yl)-benzamide, 4-{4-[(1R,2S)-2-(3-dimethylamino-propylcarbamoyl)-cyclopentylamino]-5-trifluoromethyl-pyrimidin-2-ylamino}-N-methyl-N-(1-methyl-piperidin-4-yl)-benzamide, 4-{4-[(1R,2S)-2-(azetidine-1-carbonyl)-cyclopentylamino]-5-trifluoromethyl-pyrimidin-2-ylamino}-N-methyl-N-(1-methyl-piperidin-4-yl)-benzamide, N-methyl-4-{4-[(1R,2S)-2-(4-methyl-piperidine-1-carbonyl)-cyclopentylamino]-5-trifluoromethyl-pyrimidin-2-ylamino}-N-(1-methyl-piperidin-4-yl)-benzamide, 4-[4-((1R,3S)-3-carbamoyl-cyclopentylamino)-5-trifluoromethyl-pyrimidin-2-ylamino]-N-methyl-N-(1-methyl-piperidin-4-yl)-benzamide, 4-[4-((1S,3R)-3-carbamoyl-cyclopentylamino)-5-trifluoromethyl-pyrimidin-2-ylamino]-N-methyl-N-(1-methyl-piperidin-4-yl)-benzamide, 4-[4-((1R,2S)-2-carbamoyl-cyclopentylamino)-5-cyano-pyrimidin-2-ylamino]-N-(1-methyl-piperidin-4-yl)-benzamide 4-[4-((1R,2S)-2-carbamoyl-cyclopentylamino)-5-phenylethynyl-pyrimidin-2-ylamino]-N-(1-methyl-piperidin-4-yl)-benzamide and 4-[4-((1R,2S)-2-carbamoyl-cyclopentylamino)-5-cyclopropyl-pyrimidin-2-ylamino]-N-(1-methyl-piperidin-4-yl)-benzamide are not included.

In one aspect the invention relates to compounds of general formula (1), wherein X denotes N.

In another aspect the invention relates to compounds of general formula (1), wherein m is equal to 1.

In another aspect the invention relates to compounds of general formula (1), wherein $R^2$ denotes a group selected from among halogen and $C_{1-4}$haloalkyl.

In another aspect the invention relates to compounds of general formula (1), wherein $R^2$ denotes —$CF_3$.

In another aspect the invention relates to compounds of general formula (1), wherein $R^1$ denotes $C_{4-6}$cycloalkyl.

In another aspect the invention relates to compounds of general formula (1), wherein $R^1$ denotes cyclopentyl.

In another aspect the invention relates to compounds of general formula (1), or the pharmaceutically effective salts thereof, for use as pharmaceutical compositions.

In another aspect the invention relates to compounds of general formula (1), or the pharmaceutically effective salts thereof, for preparing a pharmaceutical composition with an antiproliferative activity.

In another aspect the invention relates to a pharmaceutical preparation, containing as active substance one or more compounds of general formula (1), or the pharmaceutically effective salts thereof, optionally in combination with conventional excipients and/or carriers.

In another aspect the invention relates to the use of compounds of general formula (1) for preparing a pharmaceutical composition for the treatment and/or prevention of cancer, infections, inflammations and autoimmune diseases.

In another aspect the invention relates to a pharmaceutical preparation comprising a compound of general formula (1), optionally in the form of the tautomers, the racemates, the enantiomers, the diastereomers and the mixtures thereof, and optionally the pharmaceutically effective salts thereof and at least one other cytostatic or cytotoxic active substance different from formula (1).

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

Heteroalkyl represents unbranched or branched aliphatic hydrocarbon chains which contain 1 to 3 heteroatoms, while each of the available carbon and heteroatoms in the heteroalkyl chain may optionally each be substituted independently and the heteroatoms independently of one another are selected from among O, N, P, PO, $PO_2$, S, SO and $SO_2$ (e.g. dimethylaminomethyl, dimethylaminoethyl, dimethylaminopropyl, diethylaminomethyl, diethylaminoethyl, diethylaminopropyl, 2-diisopropylaminoethyl, bis-2-methoxyethylamino, [2-(dimethylamino-ethyl)-ethyl-amino]-methyl, 3-[2-(dimethylamino-ethyl)-ethyl-amino]-propyl, hydroxymethyl, 2-hydroxyethyl, 3-hydroxypropyl, methoxy, ethoxy, propoxy, methoxymethyl, 2-methoxyethyl).

Haloalkyl refers to alkyl groups wherein one or more hydrogen atoms are replaced by halogen atoms. Haloalkyl includes both saturated alkyl groups and unsaturated alkenyl and alkynyl groups, such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$ and —$CHFCH_2CF_3$.

Halogen refers to fluorine, chlorine, bromine and/or iodine atoms.

By cycloalkyl is meant a mono- or polycyclic ring, wherein the ring system may be a saturated ring but also an unsaturated, non-aromatic ring or a spiro compound, which may optionally also contain double bonds, such as for example cyclopropyl, cyclopropenyl, cyclobutyl, cyclobutenyl, cyclopentyl, cyclopentenyl, cyclohexyl, cyclohexenyl, cycloheptanyl, cycloheptenyl, norbornyl, norbornenyl, indanyl, adamantyl, bicyclo[2.2.3]octanyl, spiroheptanyl and spiro[4.2]heptanyl.

Cycloalkylalkyl includes a non-cyclic alkyl as hereinbefore defined wherein a hydrogen atom bound to a carbon atom, usually to a terminal C atom, is replaced by a cycloalkyl group as hereinbefore defined.

Aryl relates to monocyclic or bicyclic rings with 6-12 carbon atoms such as for example phenyl and naphthyl.

Arylalkyl includes a non-cyclic alkyl as hereinbefore defined wherein a hydrogen atom bound to a carbon atom, usually to a terminal C atom, is replaced by an aryl group as hereinbefore defined.

By heteroaryl are meant mono- or polycyclic rings which contain, instead of one or more carbon atoms, one or more heteroatoms, which may be identical or different, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridinyl, imidazopyridinyl, naphthyridinyl, indolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl as hereinbefore defined wherein a hydrogen atom bound to a carbon atom, usually to a terminal C atom, is replaced by a heteroaryl group as hereinbefore defined.

Heterocycloalkyl relates to saturated or unsaturated, non-aromatic mono-, polycyclic or bridged polycyclic rings or spiro compounds comprising 3-12 carbon atoms, which carry heteroatoms, such as nitrogen, oxygen or sulphur, instead of one or more carbon atoms. Examples of such heterocyclyl groups are tetrahydrofuranyl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2.2.1]heptane, 8-oxa-3-aza-bicyclo[3.2.1]octane, 3,8-diaza-bicyclo[3.2.1]octane, 2,5-diaza-bicyclo[2.2.1]heptane, 3,8-diaza-bicyclo[3.2.1]octane, 3,9-diaza-bicyclo[4.2.1]nonane and 2,6-diaza-bicyclo[3.2.2]nonane.

Heterocycloalkylalkyl relates to the non-cyclic alkyl as hereinbefore defined wherein a hydrogen atom bound to a carbon atom, usually to a terminal C atom, is replaced by a heterocycloalkyl group as hereinbefore defined.

By the word "substituted" is meant that a hydrogen atom which is bound directly to the atom in question is replaced by a different atom or a different atomic group. Bivalent substituents such as =O, =S, =NR, =NOR, =NNRR, =NN(R)C(O)NRR, =$N_2$ and others demand substitution by two hydrogen atoms which are bound directly to the atom in question. Accordingly, bivalent substituents of this kind may not be substituents in aromatic systems.

| List of abbreviations | |
|---|---|
| eq | equivalent(s) |
| Ac | acetyl |
| Bn | benzyl |
| Boc | t-butyloxycarbonyl |
| Bu | butyl |
| resp. | respectively |
| cHex | cyclohexane |
| DC | thin layer chromatography |
| DCC | dicyclohexylcarbodiimide |
| DCM | dichloromethane |
| DMAP | N,N-dimethylaminopyridine |
| DMF | N,N-dimethylformamide |

-continued

| List of abbreviations | |
|---|---|
| DMA | N,N-dimethylacetamide |
| DMSO | dimethylsulphoxide |
| EE | ethyl acetate |
| ESI | electron spray ionization |
| Et | ethyl |
| EtOH | ethanol |
| h | hour(s) |
| hex | hexyl |
| HPLC | high performance liquid chromatography |
| Hünig base | N-ethyl-diisopropylamine |
| i | iso |
| IR | infra-red spectroscopy |
| cat., cat | catalyst, catalytic |
| conc. | concentrated |
| bp., b.p. | boiling point |
| LC | liquid chromatography |
| LDA | lithium diisopropylamide |
| min | minute(s) |
| Me | methyl |
| MeCN | acetonitrile |
| MS | mass spectrometry |
| NMP | N-methylpyrrolidone |
| NMR | nuclear magnetic resonance |
| Ph | phenyl |
| Pr | propyl |
| rac | racemic |
| $R_f$(Rf) | retention factor |
| RP | reversed phase |
| RT | ambient temperature or retention time (HPLC) |
| tert | tertiary |
| THF | tetrahydrofuran |
| TBTU | O-(benzotriazol-1-yl)-N,N,N',N'-tetramethyl-uronium tetrafluoroborate |
| UV | ultraviolet |

The Examples that follow illustrate the present invention without restricting its scope.

General

Unless stated to the contrary, all the reactions are carried out in commercially obtainable apparatus using methods conventional in chemical laboratories. The solvents used are purchased in pro analyst quality and used without further purification. All the reagents are used directly in the synthesis without further purification.

Air- and/or moisture-sensitive starting materials are preferably stored under protective gas and corresponding reactions and manipulations with them are carried out under protective gas (nitrogen or argon).

Chromatography

For the preparative medium pressure chromatography (MPLC, normal phase) silica gel obtained from Millipore (Granula Silica Si-60A 35-70 μm) or C-18 RP silica gel (RP-phase) obtained from Macherey Nagel (Polygoprep 100-50 C18) is used.

The thin layer chromatography is carried out on ready-made silica gel 60 DC plates (with fluorescence indicator F-254) made by Merck.

For the preparative HPLC, columns made by Waters (XTerra Prep. MS C18, 5 μM, 30*100 mm or XTerra Prep. MS C18, 5 μm, 50*100 mm OBD or Symmetrie C18, 5 μm, 19*100 mm), are used, the analytical HPLC (reaction monitoring) is carried out with columns made by Agilent (Zorbax SB-C8, 5 μm, 21.2*50 mm).

For the chiral HPLC, columns made by Daicel Chemical Industries, Ltd. (Chiralpak AD-H, Chiralpak AS, Chiracel OD-RH, Chiracel OD-H or Chiracel OJ-H in various sizes and 5 μm material) are used.

HPLC-Mass Spectroscopy/UV-Spectrometry

The retention time/MS-ESI$^+$ for characterising the Examples are produced using an HPLC-MS apparatus (high performance liquid chromatography with mass detector) made by Agilent.

The apparatus is constructed so that the chromatography (column: XTerra MS C18, 2.5 μm, 2.1*30 mm, Messrs. Waters, Part. No. 186000592) is followed by a diode array detector (G1315B made by Agilent) and a mass detector (1100 LS-MSD SL; G1946D; Agilent) connected in series.

This apparatus is operated with a flow of 1.1 mL/min. For a separation process a gradient is run through within 3.1 min (gradient at the start: water/MeCN 95/5, gradient at the finish: water/MeCN 5/95; 0.1% HCOOH (formic acid) is added to each of the two solvents).

Where the preparation of the starting compounds has not been described, these are commercially obtainable or may be produced analogously to known compounds or methods described herein. Substances described in the literature are prepared using the methods of synthesis published.

Preparation of the Compounds According to the Invention

The compounds according to the invention may be prepared using the methods of synthesis described hereinafter, the substituents of the general formulae having the meanings mentioned hereinbefore. These methods are intended as an illustration of the invention without restricting it to their content and restricting the scope of the compounds claimed to these Examples.

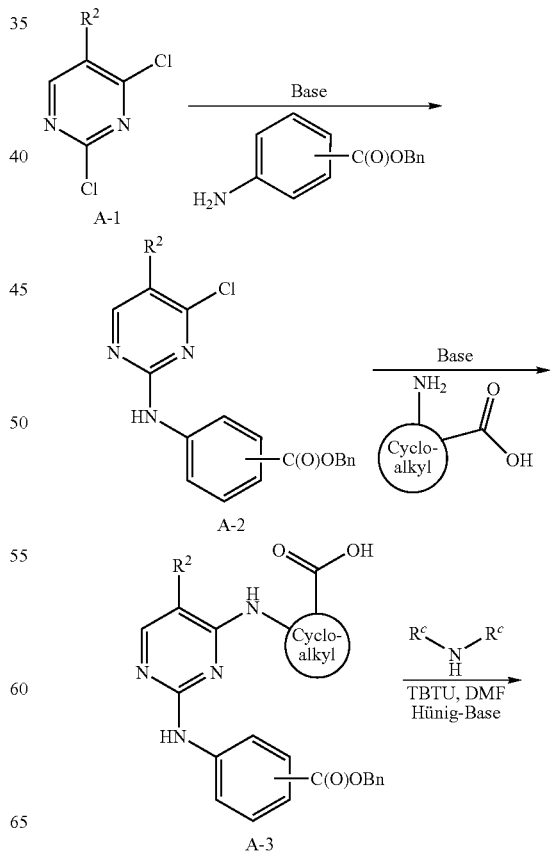

Synthesis scheme A

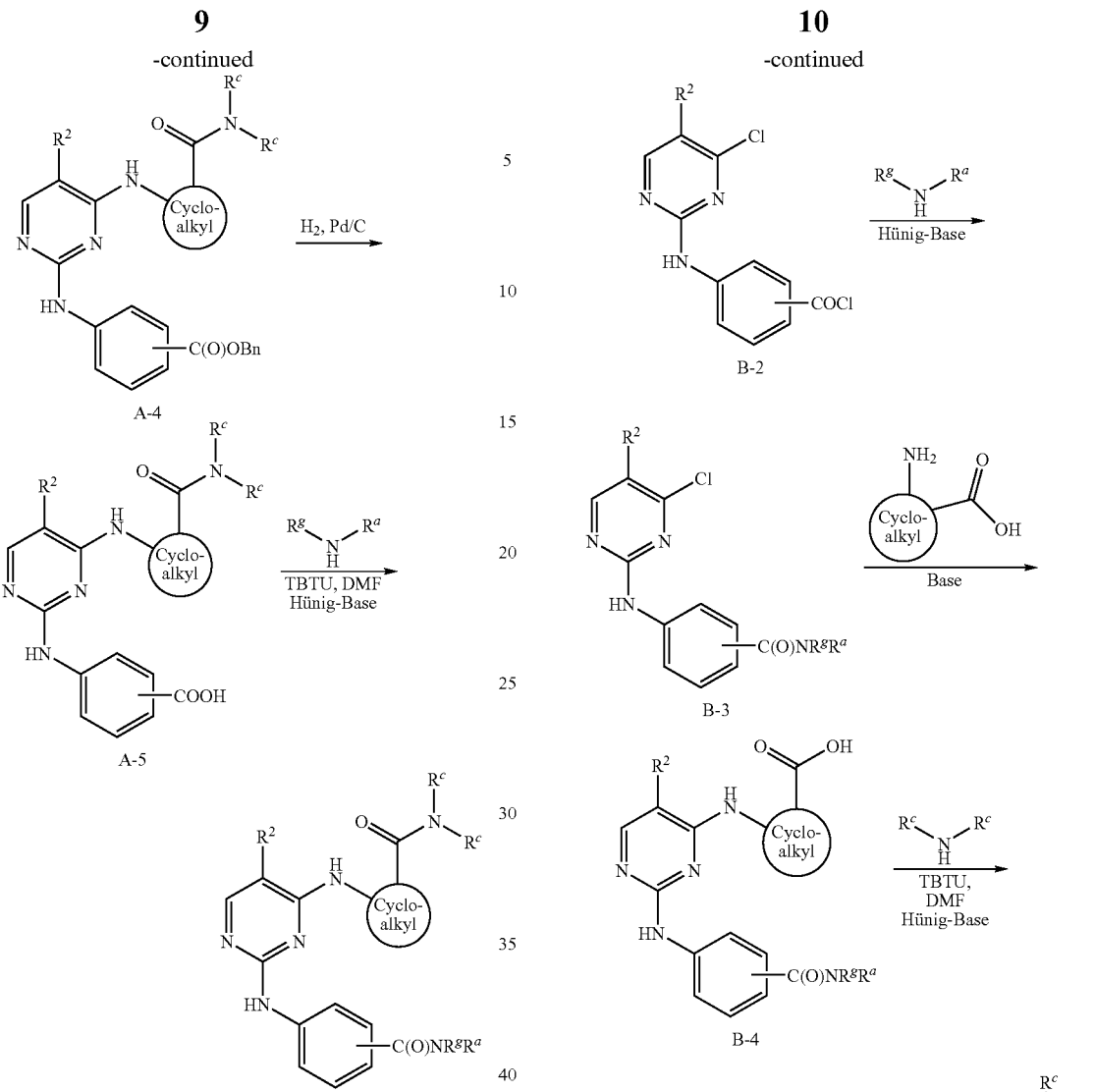
Synthesis scheme B
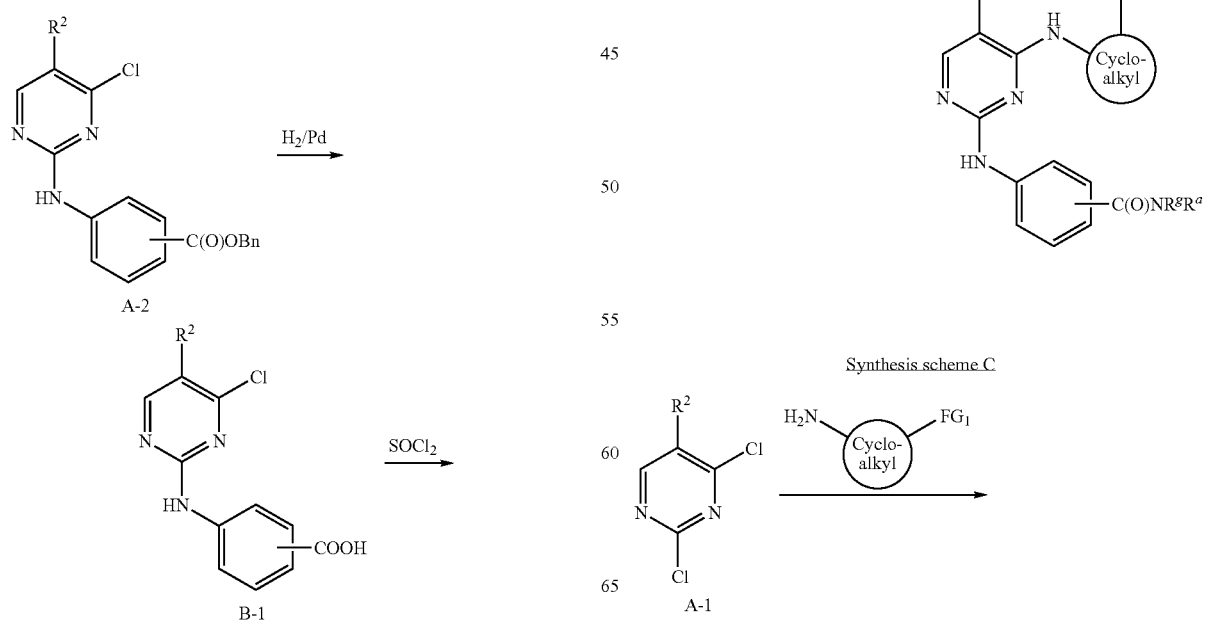
Synthesis scheme C

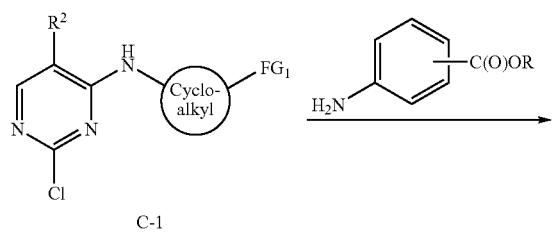
C-1
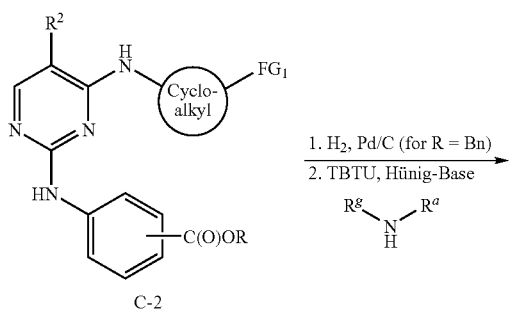
C-2
1. H$_2$, Pd/C (for R = Bn)
2. TBTU, Hünig-Base
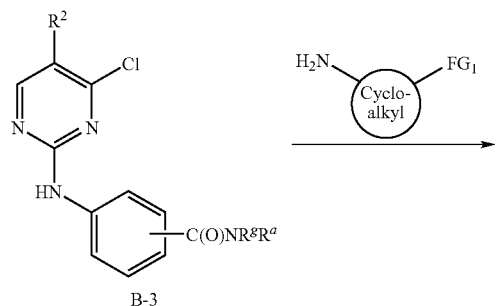
C-3
R = H or Bn
Synthesis scheme D
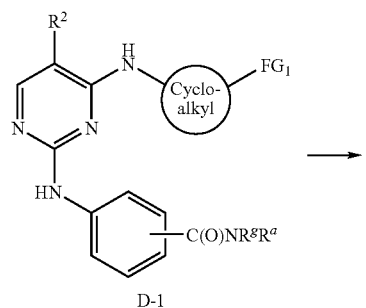
B-3
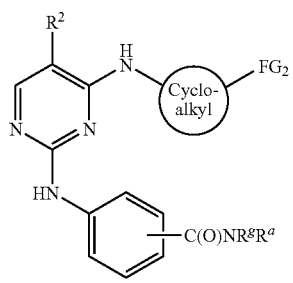
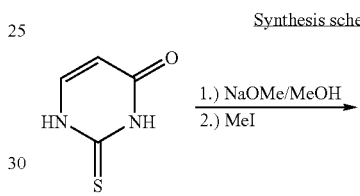
D-1
Optionally after the synthesis of the diaminopyrimidine it is also possible to transform one or more functional groups (FG$_1$ or FG$_2$). This is described in the Examples, where relevant.
Synthesis scheme E
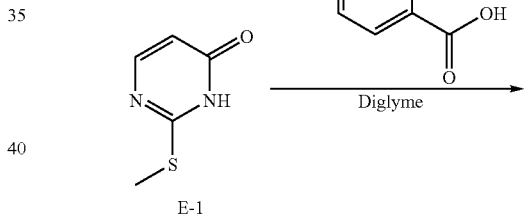
1.) NaOMe/MeOH
2.) MeI
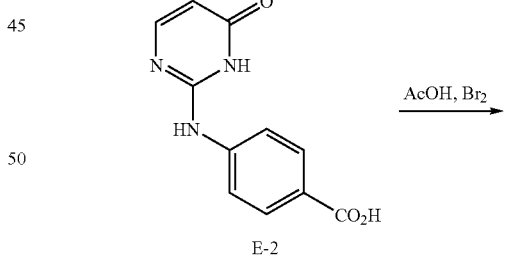
E-1
Diglyme
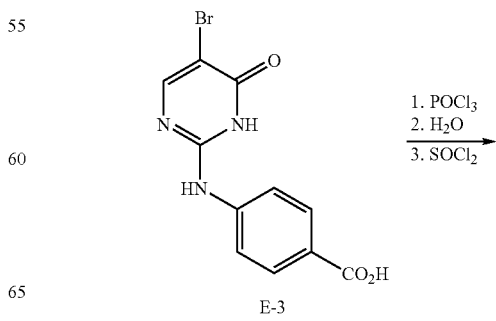
E-2
AcOH, Br$_2$
1. POCl$_3$
2. H$_2$O
3. SOCl$_2$
E-3

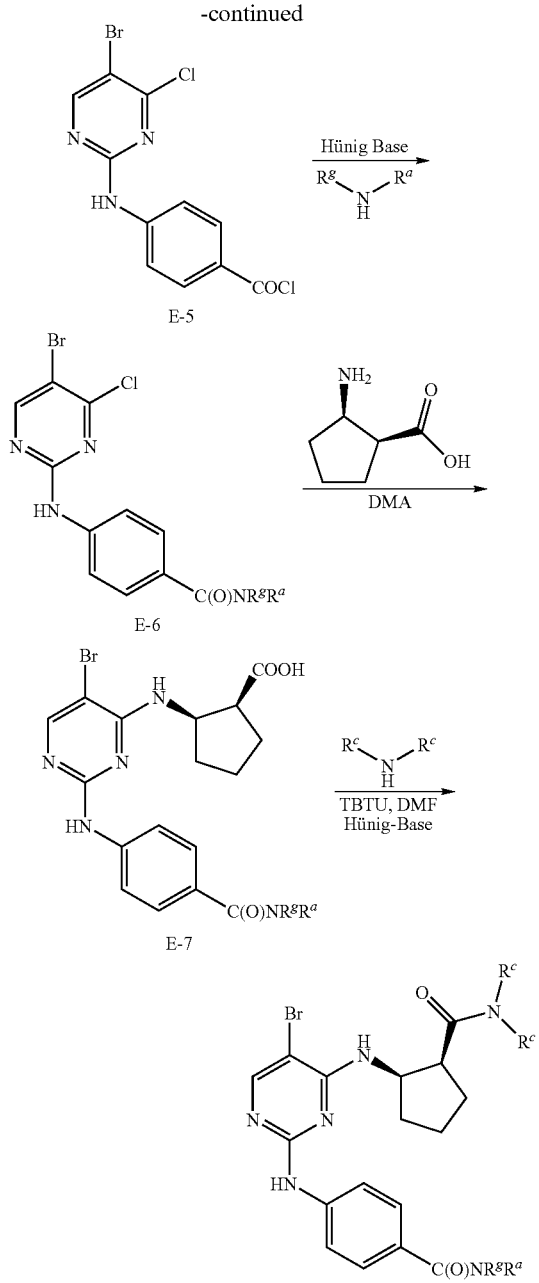

A-1a) 2,4-dichloro-5-trifluoromethyl-pyrimidine

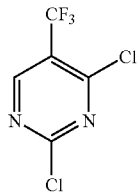 [SMILES: FC(F)(F)c1cnc(Cl)nc1Cl]

48 g (267 mmol) 5-trifluoromethyluracil are suspended in 210 mL phosphorus oxychloride (POCl₃) while moisture is excluded. 47.7 g (320 mmol, 1.2 eq) diethylaniline are added dropwise to this suspension so slowly that the temperature remains between 25° C. and 30° C. After the addition has ended the mixture is stirred for another 5-10 min in the water bath and heated for 5-6 h at 80-90° C. while moisture is excluded. The mixture obtained is stirred into approx. 1200 g sulphuric acid-containing ice water and the aqueous phase is immediately extracted 3 times with in each case 500 mL ether or tert-butyl-methyl-ether. The combined ethereal extracts are washed twice with 300 mL sulphuric acid-containing ice water (approx. 0.1 M) and with cold saline solution and dried. The desiccant is filtered off and the solvent is eliminated in vacuo. The residue is distilled in vacuo (10 mbar) through a short column (head temperature: 65-70° C.), to obtain 35.3 g of a liquid which is poured off under protective gas and stored.

DC: $R_f$=0.83 (cHex:EE=3:1)

benzyl 4-aminobenzoate

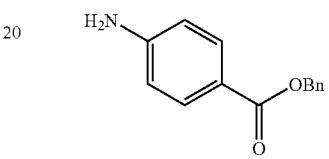

15.01 g (89.9 mmol) 4-nitrobenzoic acid are suspended in 500 mL MeCN and then combined with 15.03 g (108.7 mmol, 1.2 eq) potassium carbonate. 15.4 g (90.4 mmol, 1.01 eq) benzylbromide are added dropwise with stirring and the reaction mixture is heated for 5 h with stirring at 60° C. It is combined with 750 mL distilled water, extracted 4 times with 250 mL of EE and after the organic phases have been combined dried on sodium sulphate. After all the volatile constituents have been eliminated in vacuo the crude product is suspended twice in succession in toluene and evaporated down in vacuo. 20.6 g (80.1 mmol) benzyl 4-nitrobenzoate are obtained, which is used in the next step without any further purification.

20.6 g of the benzyl 4-nitrobenzoate are dissolved in 350 mL dioxane and this solution is combined with 6.9 g (49.9 mmol, 0.61 eq) Raney nickel. The mixture is hydrogenated at 5 bar H₂ pressure for 16 h with stirring. The catalyst is filtered off and all the volatile constituents are eliminated in vacuo. 17 g benzyl 4-aminobenzoate are obtained.

A-2a) benzyl 4-(4-chloro-5-trifluoromethyl-pyrimidin-2-ylamino)-benzoate

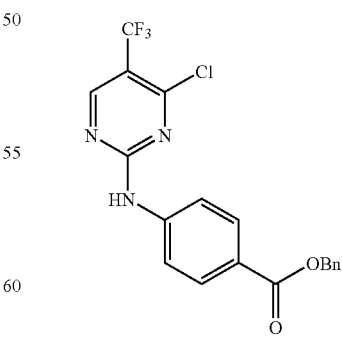

10 g (44 mmol) benzyl 4-aminobenzoate are dissolved in 200 mL DMA, 8 mL Hünig base (0.97 eq) are added and 10.4 g (48.21 mmol) 2,4-dichloro-5-trifluoromethylpyrimidine, dissolved in 50 mL DMA, are added dropwise at RT to this solution. The reaction mixture is stirred at 60° C. overnight, then combined with 300 mL DCM and extracted with water (3 times 300 mL). The organic phase is dried and the solvent is eliminated in vacuo. The crude product is combined with 100 mL MeOH, digested and left to stand for 2 h. Then it is stirred for 10 min, the precipitate is filtered off and washed with MeOH. Finally the crude product is again suspended in MeOH, filtered off, washed with a little MeOH and dried in the vacuum dryer at 60° C. 8.5 g A-2a are obtained.

$R_f$=0.71 (silica gel, cHex:EE 1:2)

MS-ESI$^+$: 408 (M+H)$^+$

A-3a) benzyl 4-[4-((1R,2S)-2-carboxy-cyclopentylamino)-5-trifluoromethyl-pyrimidin-2-ylamino]-benzoate

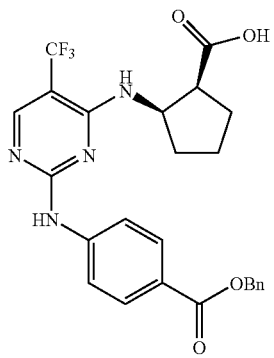 [SMILES: O=C(OCc1ccccc1)c1ccc(Nc2ncc(C(F)(F)F)c(N[C@@H]3CCC[C@@H]3C(=O)O)n2)cc1]

2.05 g (5 mmol, 1 eq) A-2a and 1 g (1S,2R)-2-amino-1-cyclopentanecarboxylic acid hydrochloride (6 mmol, 1.2 eq) are placed in 18 mL EtOH, 7.3 mL (42.5 mmol, 8.5 eq) Hünig base are added and the mixture is stirred for 4 h at 70° C. The reaction mixture is stirred into 275 mL water, filtered to remove the insoluble matter, the filtrate is adjusted to pH 2 with saturated, aqueous KHSO$_4$ solution, stirred for 5 min and the precipitate formed is suction filtered. The crude product is washed with water, dried in vacuo and 2.37 g A-3a are obtained.

MS-ESI: 501 (M+H)$^+$

The synthesis with (1R,2S)-2-amino-1-cyclopentanecarboxylic acid or (1R*,2S*)-(±)-2-amino-1-cyclopentanecarboxylic acid is carried out analogously. The corresponding products are designated A-2b (chiral, enantiomer to A-2a) and A-2c (racemic).

Preparation of (1S,2R)-2-aminocyclopentanecarboxylic acid hydrochloride

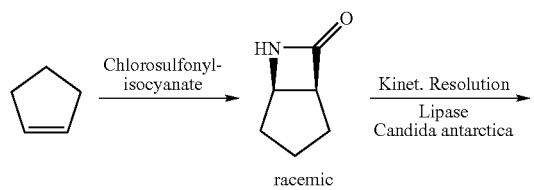

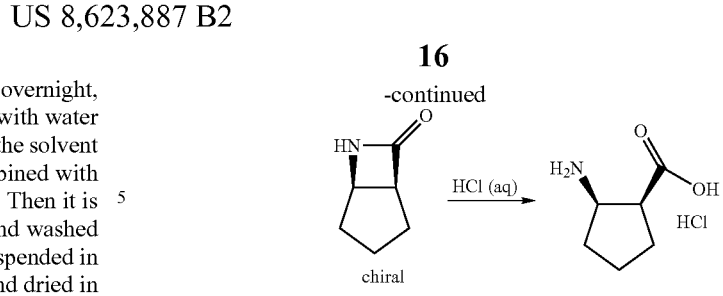

The synthesis is carried out according to Forro, E. and Fueloep, F. (2003) Lipase-Catalyzed Enantioselective Ring Opening of Unactivated Alicyclic-Fused β-Lactams in an Organic Solvent. *Org. Lett.* 5, 1209-1212.

A-4a) benzyl 4-[4-((1R,2S)-2-isopropylcarbamoyl-cyclopentylamino)-5-trifluoromethyl-pyrimidin-2-ylamino]-benzoate

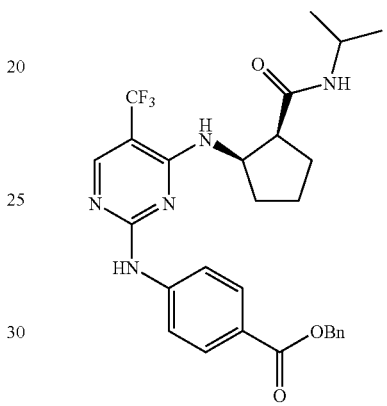

2.59 g (4.9 mmol) A-3a, 2.21 g (6.9 mmol, 1.4 eq) TBTU and 4.21 mL (24.6 mmol, 5 eq) Hünig base are dissolved in 75 mL DMF and stirred for 20 min at RT. Then 0.63 mL (7.38 mmol, 1.5 eq) isopropylamine are added and the mixture is stirred overnight at RT. It is suction filtered through basic aluminium oxide, washed with DMF and the mother liquor is stirred into 400 mL water, stirred for another 30 min and the precipitate is suction filtered. The crude product is washed with water and dried in vacuo. For purification it is stirred with 50 mL MeCN for 30 min at 5° C., suction filtered, washed with some cold MeCN and the residue is dried in vacuo. 2.13 g A-4a are obtained.

$R_f$=0.53 (silica gel, cHx:EE 1:1)

MS-ESI$^+$: 542 (M+H)$^+$

The compounds A-4-d and A-4-e are prepared analogously using ethylamine and cyclopropylamine respectively, and are used as educts in the synthesis sequence for Examples 9 and 10.

A-4d

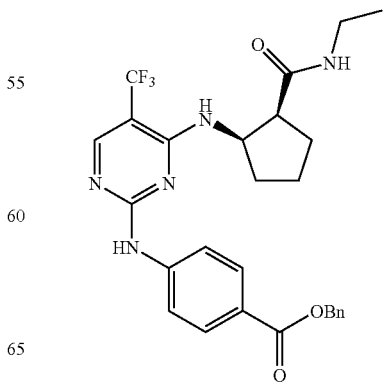

-continued

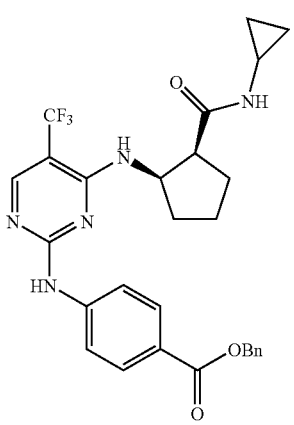

A-4e

A-5a) 4-[4-((1R,2S)-2-isopropylcarbamoyl-cyclopentylamino)-5-trifluoromethyl-pyrimidin-2-ylamino]-benzoic acid

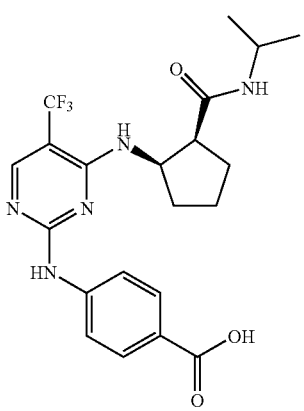 [SMILES: CC(C)NC(=O)[C@H]1CCC[C@H]1Nc1nc(Nc2ccc(C(=O)O)cc2)ncc1C(F)(F)F]

2.13 g (3.9 mmol) A-4a are dissolved in 150 mL THF and 250 mg palladium hydroxide/C-catalyst (20 wt. % Pd on charcoal) are added. The mixture is hydrogenated for 16 h at an H$_2$ pressure of 6 bar with stirring at RT. Then 30 mL MeOH are added, the catalyst is filtered off through kieselguhr, washed with MeOH and the filtrate is evaporated down. The residue is boiled with 45 mL EtOH, slowly cooled to 5° C., stirred for another 1 h and then suction filtered and washed with cold EtOH. 2.46 g A-5a are obtained.

R$_f$=0.46 (silica gel, CH$_2$Cl$_2$:MeOH:AcOH 5:1:0.1)
MS-ESI$^+$: 452 (M+H)$^+$ The syntheses of the enantiomeric compound A-5b and racemate A-5c are carried out analogously.

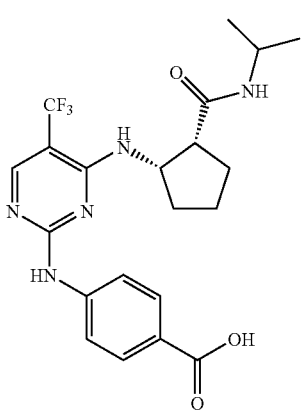

A-5b

-continued

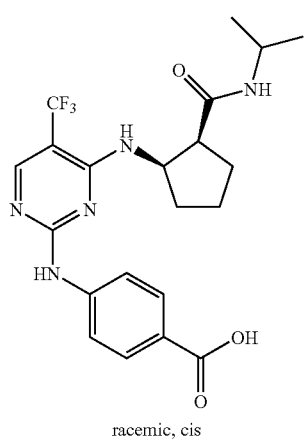

A-5c racemic, cis

A-5d) 4-[4-((1R,2S)-2-isopropylcarbamoyl-cyclobutylamino)-5-trifluoromethyl-pyrimidin-2-ylamino]-benzoic acid

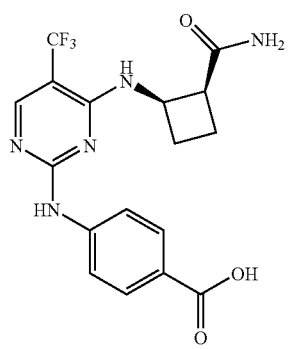 [SMILES: NC(=O)[C@H]1CC[C@H]1Nc1nc(Nc2ccc(C(=O)O)cc2)ncc1C(F)(F)F]

250 mg (2.8 mmol, 1 eq) B-1a are dissolved in 1 mL DMA and 0.74 mL (4.3 mmol, 5.5 eq) Hünig base are added. Then 461 mg (2.4 mmol, 3 eq) cis-2-aminocyclobutane-carboxylic acid amide are added and the reaction mixture is heated to 70° C. After 1 h the reaction is complete. The reaction mixture is combined with RP gel, the volatile constituents are eliminated in vacuo and the product is purified by column chromatography through an RP phase and isolated (water/MeCN 78/22 (+0.2% HCOOH) to water/MeCN 58/42 in 12 min). Corresponding product fractions are combined, freed from the solvent by freeze-drying and 50 mg A-5d are obtained.

methyl-(1,2,2,6,6-pentamethyl-piperidin-4-yl)-amine

Educt Synthesis Example 1

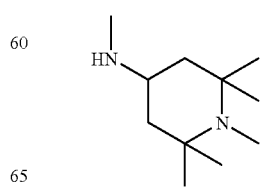

2 g (11.8 mmol, 1 eq) 1,2,2,6,6-pentamethyl-4-piperidone are dissolved in 10 mL THF, 3.99 g (59.1 mmol, 5 eq) methylamine hydrochloride are added and the reaction mixture is stirred for 1 h at RT. Then 4.85 g (59.1 mmol, 5 eq) sodium acetate and 2.78 g (11.82 mmol, 1 eq) sodium trisacetoxyborohydride are added and the reaction mixture is stirred for 16 h at RT. Monitoring of the reaction by thin layer chromatography shows total conversion. It is filtered to remove the insoluble matter, the filtrate is combined with silica gel and the volatile constituents are eliminated in vacuo. 373 mg of the amine is obtained by purification by column chromatography (normal phase, silica gel, DCM/MeOH/NH$_3$(aq) 7/3/0.3).

$R_f$=0.47 (silica gel, CH$_2$Cl$_2$/MeOH/NH$_3$ 6/4/0.4)

(1-ethyl-piperidin-4-yl)-methyl-amine

Educt Synthesis Example 5

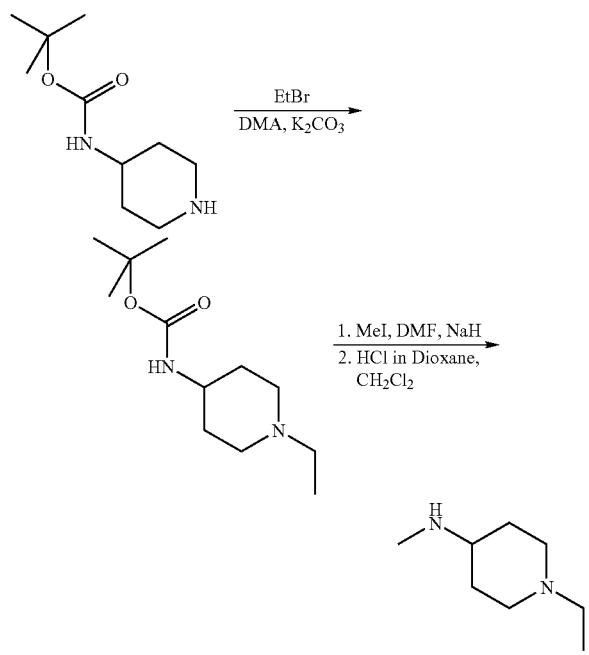

10 g of 4-(Boc-amino)piperidine, 4 mL of ethylbromide and 10 g of potassium carbonate are stirred in 75 mL of DMA for 2 h at 120° C. The reaction mixture is stirred into 500 mL water, extracted 3 times with 150 mL EE, the organic phase is dried on MgSO$_4$, evaporated down and the residue is dissolved in 300 mL diethyl ether. It is combined with 20 mL of 4 M hydrochloric acid in 1,4-dioxane while cooling with ice, stirred for another 15 min at 0° C. and the precipitate is suction filtered, washed with diethyl ether and dried in vacuo. 11.5 g tert-butyl (1-ethyl-piperidin-4-yl)-carbamate hydrochloride are obtained, which is used without any further purification.

1 g (3.8 mmol, 1 eq) tert-butyl (1-ethyl-piperidin-4-yl)-carbamate hydrochloride is dissolved in 25 mL DMF, 378 mg (9.4 mmol, 2.5 eq, 60% dispersion in oil) of sodium hydride are added and after the addition of 246 μL (3.95 mmol, 1.1 eq) methyliodide the mixture is stirred for 30 min at RT. The reaction mixture is stirred into 150 mL water, adjusted to pH 8 with saturated aqueous NaHCO$_3$ solution and extracted 3 times with 50 mL EE. The organic phase is dried on MgSO$_4$, the solvent is eliminated in vacuo and 300 mg tert-butyl (1-ethyl-piperidin-4-yl)-methyl-carbamate are obtained. This is placed in 5 mL DCM, 928 μL hydrochloric acid (4 M in 1,4-dioxane, 3 eq) are added and the mixture is stirred for 4 h at RT. After the conversion has reached only approx. 30% 1 mL trifluoroacetic acid is added and the mixture is stirred for 1 h at RT. It is evaporated down in vacuo and the crude (1-ethyl-piperidin-4-yl)-methyl-amine is used without further purification for the amide coupling.

tert-butyl 4-isopropylamino-piperidin-1-carboxylate

Educt Synthesis of Example 6

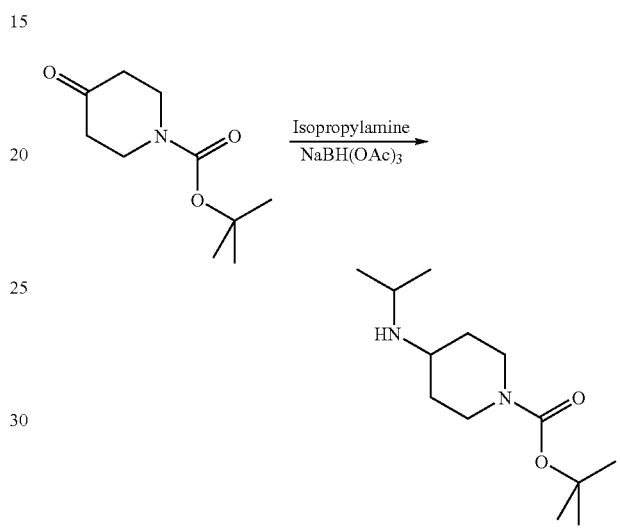

500 mg (2.51 mmol, 1 eq) 1-Boc-4-piperidinone are placed in 7 mL of 1,2-dichloroethane, 214 μL (2.51 mmol, 1 eq) isopropylamine are added and the mixture is stirred for 20 min at RT. After the addition of 145 μL (2.51 mmol, 1 eq) glacial acetic acid, 745 mg (3.5 mmol, 1.4 eq) sodium trisacetoxyborohydride are added batchwise and the mixture is stirred overnight at RT. The reaction mixture is combined with 25 mL saturated, aqueous NaHCO$_3$ solution, then after the development of gas has ended it is extracted 3 times with 20 mL DCM, the combined organic phases are dried on MgSO$_4$, the solvent is eliminated in vacuo and 527 mg of the amine product is obtained, which is used without any further purification.

(±)-Cis-2-aminocyclobutanecarboxylic Acid Amide

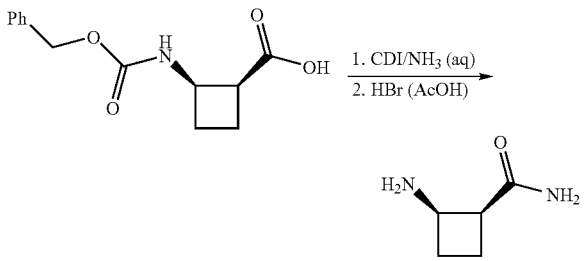

5 g (20.1 mmol, 1 eq) cis-2-(benzyloxycarbonylamino)-cyclobutanecarboxylic acid are dissolved in 10 mL THF and 3.9 g (24.1 mmol, 1.2 eq) carbonyldiimidazole (CDI) are added. The clear solution is stirred for 40 min at RT and then 26.6 mL aqueous ammonia solution (1.4 mol, 70 eq, 28-30%) are added. 30 min after the addition the reaction mixture is poured onto 500 mL water and extracted 3 times with 150 mL EE. After combining the organic phases, drying on $MgSO_4$ and eliminating all the volatile constituents in vacuo 4.05 g of the N-Z-cis-2-aminocyclobutanecarboxylic acid amide is obtained.

MS-ESI$^+$: 249 (M+H)$^+$

In order to eliminate the protective group 2 g (8.06 mmol, 1 eq) of the product are suspended at 0° C. in a solution of 100 mL hydrogen bromide in glacial acetic acid (33%) and stirred for 2 h at 0° C. The solution is stirred into approx. 500 mL diethyl ether, the precipitate is suction filtered and stirred for 2 h in diethyl ether. The precipitate is washed with THF and 1.27 g cis-2-aminocyclobutanecarboxylic acid amide are obtained as the hydrobromide.

MS-ESI$^+$: 115 (M+H)$^+$ (±)-Cis-2-aminocyclobutanecarboxylic acid isopropylamide

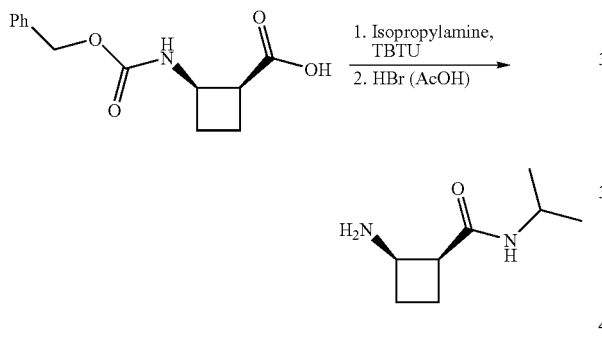

1 g (4 mmol, 1 eq) cis-2-(benzyloxycarbonylamino)-cyclobutanecarboxylic acid are dissolved in 2 mL THF and 3.22 g (10 mmol, 2.5 eq) TBTU and 3.43 mL (20 mmol, 5 eq) Hünig base are added. The suspension is stirred for 30 min at RT and then 513 µL (6.02 mmol, 1.5 eq) isopropylamine are added dropwise. After 16 h stirring at RT the conversion is complete and the reaction mixture is stirred into 200 mL water. It is extracted 3 times with 50 mL EE. After combining the organic phases, drying on $MgSO_4$ and eliminating all the volatile constituents in vacuo 1.1 g of N-Z-cis-2-aminocyclobutanecarboxylic acid isopropylamide is obtained.

$R_f$=0.57 (silica gel, $CH_2Cl_2$/MeONH$_3$ 9/1/0.1)

MS-ESI$^+$: 291 (M+H)$^+$

In order to eliminate the protective group 1.1 g (3.79 mmol, 1 eq) of the product are suspended at 0° C. in a solution of 100 mL hydrogen bromide in glacial acetic acid (33%) and stirred for 2 h at 0° C. The solution is stirred into approx. 500 mL diethyl ether, the precipitate is suction filtered and stirred for 2 h in diethyl ether. After washing the precipitate with THF, 644 mg cis-2-aminocyclobutanecarboxylic acid isopropylamide are obtained as the hydrobromide.

MS-ESI$^+$: 157 (M+H)$^+$

B-1a) 4-(4-chloro-5-trifluoromethyl-pyrimidin-2-ylamino)-benzoic acid

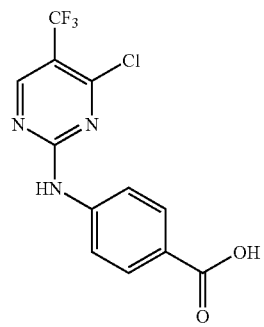 [SMILES: O=C(O)c1ccc(Nc2ncc(C(F)(F)F)c(Cl)n2)cc1]

2 g (4.91 mmol) A-2a are dissolved in 88 mL dioxane, 220 mg palladium hydroxide (1.57 mmol, 0.32 eq) are added and the mixture is stirred for 16 h at 3 bar $H_2$ pressure and RT. The reaction mixture is filtered through Celite®, washed with THF, the filtrate is freed from the solvent in vacuo and 1.31 g B-1a are obtained, which are used without further purification.

MS-ESI+: 318 (M+H)$^+$

B-2a) 4-(4-chloro-5-trifluoromethyl-pyrimidin-2-ylamino)-benzoyl chloride

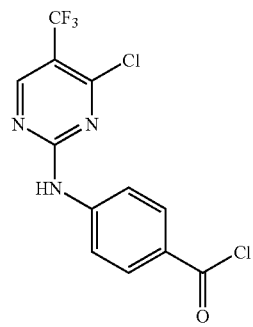 [SMILES: O=C(Cl)c1ccc(Nc2ncc(C(F)(F)F)c(Cl)n2)cc1]

1.31 g (4.13 mmol) B-1a are suspended in 100 mL toluene, 360 µL (4.96 mmol, 1.2 eq) thionyl chloride are cautiously added with stirring and the solution is refluxed for 1 h. All the volatile constituents are eliminated in vacuo after cooling to RT and the residue B-2a is further reacted without any more purification.

B-3a) 4-(4-chloro-5-trifluoromethyl-pyrimidin-2-ylamino)-N-methyl-N-(1-methyl-piperidin-4-yl)-benzamide

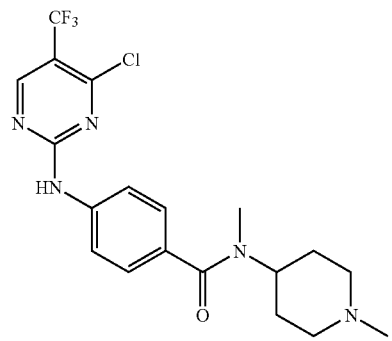 [SMILES: CN1CCC(N(C)C(=O)c2ccc(Nc3ncc(C(F)(F)F)c(Cl)n3)cc2)CC1]

1.36 g (4.05 mmol) B-2a are dissolved in 10 mL THF and combined with 1.04 mL (6.1 mmol, 1.5 eq) Hünig base. After the addition of 589 µL (4.1 mmol, 1 eq) 1-methyl-4-(methylamino)-piperidine the solution is stirred for 1 h at RT. The reaction mixture is poured into approx. 100 mL distilled water, stirred for 30 min and the aqueous phase is extracted 3 times with 100 mL EE. After drying the organic phase on MgSO$_4$, filtration and elimination of the volatile constituents in vacuo, 1.64 g B-3a are obtained.

R$_f$=0.30 (silica gel, CH$_2$Cl$_2$/MeOH/NH$_3$ 5/1/0.1)
MS-ESI+: 428 (M+H)$^+$ B-4c) (±)-(1S*,2R*)-2-(2-{4-[methyl-(1-methyl-piperidin-4-yl)-carbamoyl]-phenylamino}-5-trifluoromethyl-pyrimidin-4-ylamino)-cyclopentanecarboxylic acid

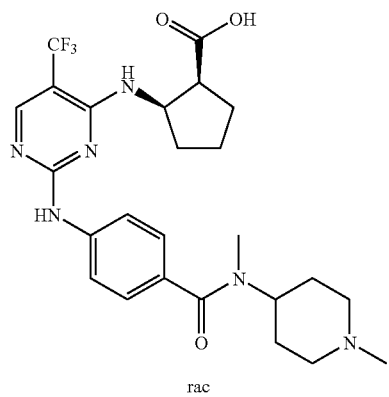 [SMILES: CN1CCC(N(C)C(=O)c2ccc(Nc3ncc(C(F)(F)F)c(N[C@@H]4CCC[C@@H]4C(=O)O)n3)cc2)CC1]

rac 1 g (2.34 mmol) B-3a are dissolved in 2.9 mL DMA and then 1.2 mL (7.01 mmol, 3 eq) Hünig base are added. After the addition of 465 mg (2.81 mmol, 1.2 eq) cis-2-amino-1-cyclopentanecarboxylic acid (racemic) the mixture is stirred for approx. 30 min at 120° C. The reaction mixture is combined with RP gel, the volatile constituents are eliminated in vacuo, the product is purified by column chromatography through an RP phase and isolated (water/MeCN 85/15 (+0.2% HCOOH) to water/MeCN 72/28 in 10 min). Corresponding product fractions are combined, freed from the solvent by freeze-drying and 578 mg B-4-c are obtained.

MS-ESI$^+$: 521 (M+H)$^+$

B-4a is prepared analogously using EtOH as solvent and (1S,2R)-2-aminocyclopentanecarboxylic acid as starting material.

B-4a) (1S,2R)-2-(2-{4-[methyl-(1-methyl-piperidin-4-yl)-carbamoyl]-phenylamino}-5-trifluoromethyl-pyrimidin-4-ylamino)-cyclopentanecarboxylic acid

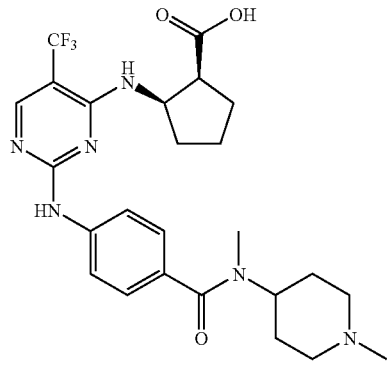

MS-ESI$^+$:521 (M + H)$^-$

B-4-d) (1S,3R)-3-(2-[4-[methyl-(1-methyl-piperidin-4-yl)-carbamoyl]-phenylamino]-5-trifluoromethyl-pyrimidin-4-ylamino)-cyclopentanecarboxylic acid

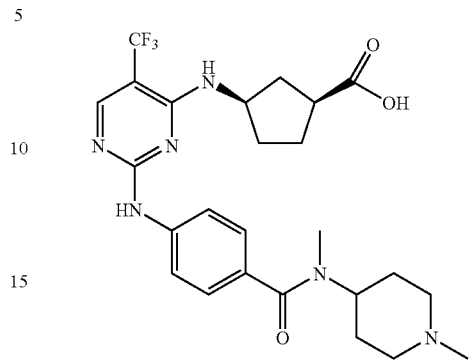

200 mg (0.46 mmol, 1 eq) B-3a are dissolved in 750 µL DMA and 160 µL (0.92 mmol, 2 eq) Hünig base are added. Then 72 mg (0.56 mmol, 1.2 eq) (1S,3R)-3-aminocyclopentanecarboxylic acid are added and the reaction mixture is heated to 120° C. with stirring for 40 min. The reaction mixture is combined with RP gel, the volatile constituents are eliminated in vacuo, the product is purified by column chromatography through an RP phase and isolated (from water/MeCN 85/15 (+0.2% HCOOH) to water/MeCN 76/24 in 20 min). Corresponding product fractions are combined, freed from the solvent by freeze-drying and 150 mg of B-4-d are obtained.

The enantiomeric compound B-4-e may be prepared analogously using (1R,3S)-3-aminocyclopentanecarboxylic acid.

B-4e

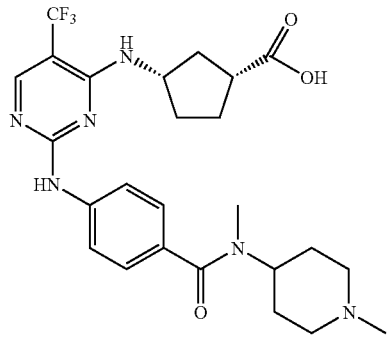 [SMILES: CN1CCC(N(C)C(=O)c2ccc(Nc3ncc(C(F)(F)F)c(N[C@@H]4CC[C@H](C(=O)O)C4)n3)cc2)CC1]

3-amino-bicyclo[2,2,2]octane-2-carboxylic acid

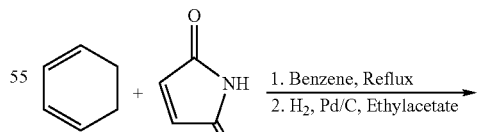

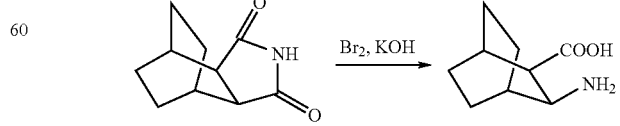

9.7 g (99.9 mmol, 1 eq) maleimide are suspended in 100 mL benzene and then 8 g (99.9 mmol, 1 eq) cyclohexadiene, suspended in 20 mL benzene, are slowly added at 5° C. The reaction mixture is slowly heated to reflux temperature and refluxed for 3 h with stirring. After cooling to 0° C. the precipitate is filtered off and dried in vacuo. 14.7 g of the cycloaddition product are obtained.

MS-ESI⁺: 178 (M+H)⁺

12.2 g (68.6 mmol, 1 eq) of the cycloaddition product are dissolved in 240 mL EE and 1.2 g of palladium on activated charcoal (20% w/w Pd, 11.3 mmol, 0.16 eq) are added. The reaction mixture is stirred at RT under a hydrogen atmosphere (5 bar) until no more hydrogen is taken up (20 h). Then a mixture of MeOH and DCM (1/1, 50 mL) is added, the catalyst is filtered off and the volatile constituents are eliminated in vacuo. 12.1 g product are obtained, which is reacted without further purification.

At 0° C. 3.7 mL (72.2 mmol, 1 eq) bromine are added dropwise to a solution of 36.6 g (652.2 mmol, 9 eq) potassium hydroxide in water. 13 g (72.7 mmol, 1 eq) of the hydrogenation product are added to the solution while continuing to cool to 0° C. After warming up to RT the mixture is heated to 60° C. for 2.5 h. The reaction mixture is cooled to RT, acidified with aqueous hydrochloric acid and all the volatile constituents are eliminated in vacuo. The residue is triturated with cold water, the precipitate is filtered off, the filtrate is evaporated to dryness, decocted with hot 1-butanol, filtered again to remove the insoluble matter and washed with hot 1-butanol. The filtrate is evaporated down in vacuo and recrystallisation from EtOH yields 2.4 g of the title compound.

MS-ESI⁺: 170 (M+H)⁺

B-4f) 3-(2-{4-[methyl-(1-methyl-piperidin-4-yl)-carbamoyl]-phenylamino}-5-trifluoromethyl-pyrimidin-4-ylamino)-bicyclo[2,2,2]octane-2-carboxylic acid

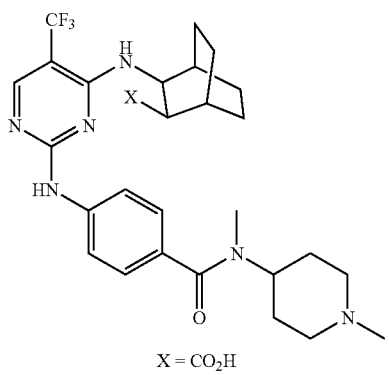

B-4f is prepared analogously to B-4a with EtOH as solvent by reacting 3-amino-bicyclo[2,2,2]octane-2-carboxylic acid with B-3a.

MS-ESI⁺: 561 (M+H)⁺

B-4g) 3-(2-{4-[methyl-(1-methyl-piperidin-4-yl)-carbamoyl]-phenylamino}-5-trifluoromethyl-pyrimidin-4-ylamino)-cyclobutanecarboxylic acid

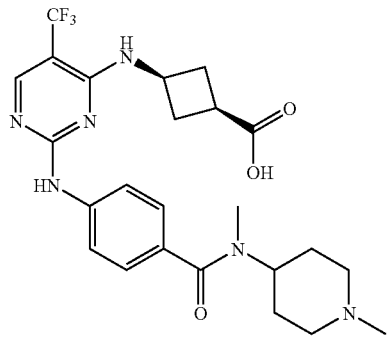 [SMILES: CN1CCC(N(C)C(=O)c2ccc(Nc3ncc(C(F)(F)F)c(N[C@H]4C[C@@H](C(=O)O)C4)n3)cc2)CC1]

B-4g is prepared analogously to B-4a with EtOH as solvent by reacting cis-3-amino-cyclobutanecarboxylic acid with B-3a.

B-4h) (±)-(1S*,2R*)-2-(2-{4-[methyl-(1-methyl-piperidin-4-yl)-carbamoyl]-phenylamino}-5-trifluoromethyl-pyrimidin-4-ylamino)-cyclohexanecarboxylic acid

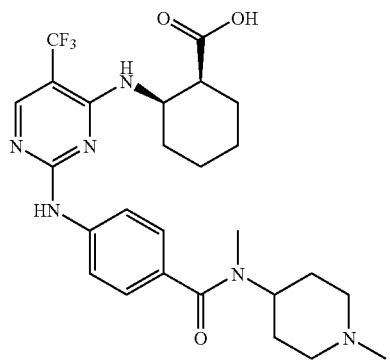 [SMILES: CN1CCC(N(C)C(=O)c2ccc(Nc3ncc(C(F)(F)F)c(N[C@@H]4CCCC[C@@H]4C(=O)O)n3)cc2)CC1]

B-4h is prepared analogously to B-4a with 1-butanol as solvent by reacting (±)-cis-2-amino-cyclohexanecarboxylic acid with B-3a.

B-4i) (±)-(1S*,6R*)-6-(2-{4-[methyl-(1-methyl-piperidin-4-yl)-carbamoyl]-phenylamino}-5-trifluoromethyl-pyrimidin-4-ylamino)-cyclohex-3-enecarboxylic acid

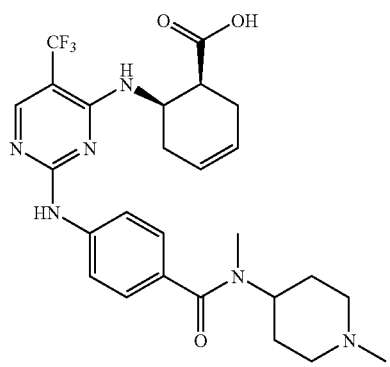 [SMILES: CN1CCC(N(C)C(=O)c2ccc(Nc3ncc(C(F)(F)F)c(N[C@@H]4CC=CC[C@@H]4C(=O)O)n3)cc2)CC1]

B-4i is prepared analogously to B-4a with 1-butanol as solvent by reacting (±)-cis-2-amino-cyclohex-3-enecarboxylic acid (Messrs. BioBlocks) with B-3a.

cis-(±)-2-amino-cyclopentanecarboxylic acid-isopropylamide

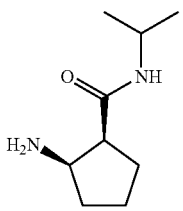

55 mg (0.43 mmol) cis-(±)-2-amino-cyclopentanecarboxylic acid are suspended in 900 µL (25 eq) isopropylamine and 205 mg (0.064 mmol, 1.5 eq) TBTU and 550 µL DMF are added. The mixture is stirred for 16 h and the reaction mixture is taken up in DCM/MeOH/NH$_3$(aq) 9/1/0.1 and combined with 7 mL silica gel. After all the volatile constituents have been eliminated in vacuo the residue is chromatographed (silica gel DCM/MeOH/NH$_3$ 9/1/0.1). 63 mg of the title compound are obtained.

$R_f$=0.33 (silica gel, DCM/MeOH/NH$_3$ 85/15/1.5)

The chiral compound (1S,2R)-2-aminocyclopentane-carboxylic acid isopropylamide is prepared analogously to this procedure using (1S,2R)-2-aminocyclopentanecarboxylic acid. In addition, a number of amides are prepared in this way starting from 2-aminocyclopentanecarboxylic acid (racemic or chiral).

General Method for Synthesising Compounds of Type C-1

A correspondingly R²-substituted 2,4-dichloropyrimidine A-1 (commercially obtainable or prepared by chlorination of the corresponding uracil as described for A-1a by way of example) is dissolved in THF (dioxane, DMA, NMP, acetone or DCM) (approx. 2-5 mL/mmol), 1-1.6 eq Hünig base (triethylamine, potassium carbonate or another suitable base) and the reaction mixture is maintained at a controlled temperature (−78° C. for very reactive pyrimidines, RT or elevated temperature for pyrimidines with a tendency to be less reactive). Then approx. 0.75-1 eq of the amine, dissolved in the corresponding solvent (see above), are added and the reaction mixture is stirred or thawed or heated for a specific time at the corresponding temperature, depending on the reactivity of the pyrimidine used. After the reaction has ended (reaction monitored by HPLC or DC) the reaction mixture is combined with silica gel and all the volatile constituents are eliminated in vacuo. Purification by column chromatography yields the desired substitution products. Depending on the group R² of the pyrimidine the two possible regioisomers are produced in different ratios. They can generally be separated by chromatography.

C-1c) (±)-(1S*,2R*)-2-(2-chloro-5-trifluoromethyl-pyrimidin-4-ylamino)-cyclopentane-carboxylic acid isopropylamide

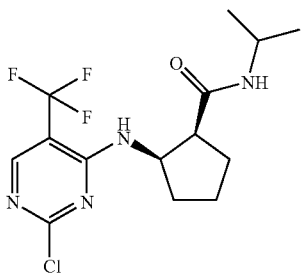 [SMILES: CC(C)NC(=O)[C@H]1CCC[C@H]1Nc1nc(Cl)ncc1C(F)(F)F]

2 g (9.2 mmol) A-1a and 1.8 mL (11.2 mmol, 1.2 eq) Hünig base are dissolved in 60 mL THF, cooled to −78° C., then cis-(±)-2-aminocyclopentanecarboxylic acid-isopropylamide, dissolved in 60 mL THF, is slowly added dropwise at −78° C. The reaction mixture is allowed to thaw to RT overnight with stirring. Then 40 mL silica gel are added and all the volatile constituents are eliminated in vacuo. The two regioisomeric products are separated by column chromatography, the desired regioisomer being the first product eluted (silica gel, cHex/EE from 85/15 to 80/20 within 30 min). 590 mg C-1c and 690 mg of the regioisomeric product C-1c' are isolated.

$R^f$(C-1c)=0.21 (silica gel, cHex/EE 3/1), [$R^f$(C-1c')=0.10]

MS-ESI+: 351 (M+H)⁺

UV$_{max}$=246 nm

C-1a (1S,2R)-2-(2-chloro-5-trifluoromethyl-pyrimidin-4-ylamino)-cyclopentanecarboxylic acid-isopropylamide

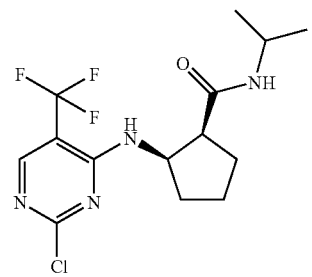 [SMILES: CC(C)NC(=O)[C@H]1CCC[C@H]1Nc1nc(Cl)ncc1C(F)(F)F]

The chiral compound C-1a is prepared from (1S,2R)-2-aminocyclopentanecarboxylic acid isopropylamide analogously.

C-1d (1S,2R)-2-(2-chloro-5-methyl-pyrimidin-4-ylamino)-cyclopentanecarboxylic acid isopropylamide

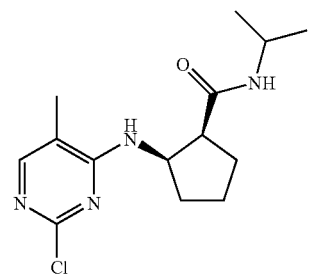 [SMILES: Cc1cnc(Cl)nc1N[C@@H]1CCC[C@@H]1C(=O)NC(C)C]

1 g (6.1 mmol, 1 eq) 5-methyl-2,4-dichloropyrimidine (prepared analogously to A-1a) are dissolved in 3 mL DMA and then 5.3 mL (30.5 mmol, 5 eq) Hünig base are added dropwise. 1.03 g (6.1 mmol, 1 eq) (1S,2R)-2-aminocyclopentanecarboxylic acid isopropylamide are added and the reaction mixture is stirred for 1 h at 70° C. HPLC monitoring shows that the reaction is total and only one regioisomer is formed. The reaction mixture is combined with RP gel, the volatile constituents are eliminated in vacuo, the product is purified by column chromatography through an RP phase and isolated (from water/MeCN (+0.2% HCOOH in each case) from 82/18 to 60/40 in 15 min). Corresponding product fractions are combined, freed from the solvent by freeze-drying and 956 mg of C-1d are obtained.

$R_f$=0.15 (silica gel, cHex:EE 1:1)

MS-ESI+: 297/299 (M+H)⁺

C-1e (1S,2R)-2-(2-chloro-5-bromo-pyrimidin-4-ylamino)-cyclopentanecarboxylic acid-isopropylamide

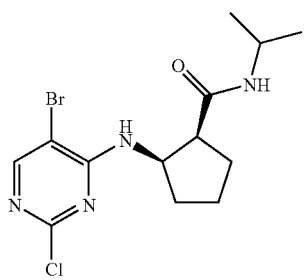 [SMILES: CC(C)NC(=O)[C@H]1CCC[C@H]1Nc1nc(Cl)ncc1Br]

C-1e is synthesised analogously to the preparation of C-1d using 1-butanol (0.7 M) as solvent at 70° C. and stirring for 2 h. It is isolated by evaporation in vacuo and washing the precipitate with MeOH.
MS-ESI+: 361/363 (M+H)$^+$

C-1f (1S,2R)-2-(2,5-dichloro-pyrimidin-4-ylamino)-cyclopentanecarboxylic acid isopropylamide

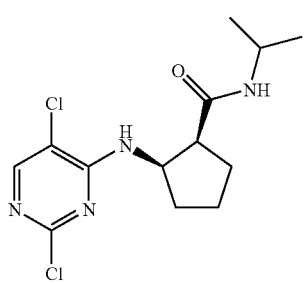 [SMILES: CC(C)NC(=O)[C@H]1CCC[C@H]1Nc1nc(Cl)ncc1Cl]

C-1f is synthesised analogously to the preparation of C-1d using DCM (0.3 M) as solvent.
The starting compounds are combined at 0° C. and the reaction mixture is stirred for 6 h at RT.
$R_f$=0.63 (silica gel, EE)

C-2a 4-[4-((1R,2S)-2-isopropylcarbamoyl-cyclopentylamino)-5-trifluoromethyl-pyrimidin-2-ylamino]-2-ethoxy-benzoic acid

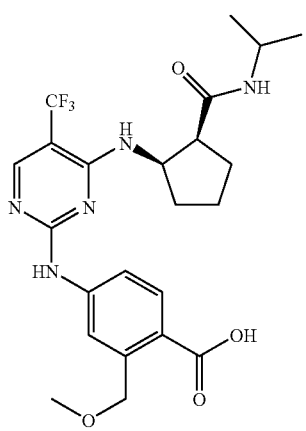 [SMILES: COCc1cc(Nc2ncc(C(F)(F)F)c(N[C@@H]3CCC[C@@H]3C(=O)NC(C)C)n2)ccc1C(=O)O]

120 mg (0.34 mmol, 1 eq) C-1a are suspended with 102 mg (0.56 mmol, 1.7 eq) 2-ethoxy-4-aminobenzoic acid in 500 μL DMA (anhydrous), combined with 221 μL dioxanic HCl (0.89 mmol, 2.6 eq, 4 M) and shaken for 2.5 h at 70° C. The reaction mixture is poured into 10 mL water, acidified with concentrated aqueous hydrochloric acid and the precipitate is filtered off. After drying in vacuo 143 mg C-2a are obtained and used without further purification.

The reaction is carried out analogously with other 2-alkoxy-substituted benzoic acids (synthesis of the starting compounds for the preparation of Examples 131, 133 and 134). 2-Chloro-4-amino-benzoic acid is used for the preparation of Example 135.

2-ethoxy-4-amino-benzoic acid

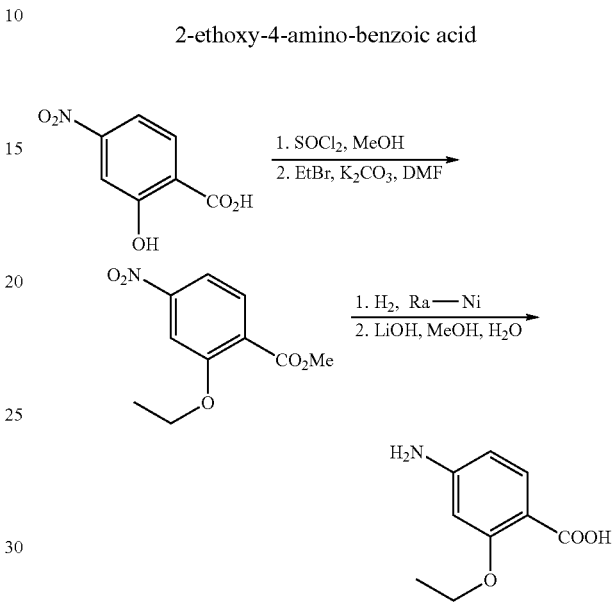

4.05 g (21.7 mmol, 1 eq) 2-hydroxy-4-nitro-benzoic acid are dissolved in 40 mL MeOH and 1.8 mL (24.8 mmol, 1.14 eq) thionyl chloride are slowly added dropwise. The mixture is refluxed for 2 h at 50° C. and stirred for another 2 h. After cooling the volatile constituents are eliminated in vacuo and 4.36 g of the crude methyl 2-hydroxy-4-nitro-benzoate are obtained, which are reacted without further purification. 1 g (5.1 mmol, 1 eq) of the methyl ester are dissolved in 25 mL DMF, 2.1 g (15.3 mmol, 3 eq) potassium carbonate are added and then 1.4 mL (18.8 mmol, 3.7 eq) bromoethane are added dropwise. The reaction mixture is stirred for 16 h at RT, then poured into 100 mL water and the pH is adjusted with concentrated aqueous hydrochloric acid to pH 3. It is extracted twice with 100 mL EE, dried on MgSO$_4$ and after the elimination of all the volatile constituents in vacuo 1.28 g of methyl 2-ethoxy-4-nitro-benzoate are obtained. 1.28 g (5.06 mmol, 1 eq) of the nitro compound are dissolved in 50 mL MeOH, a spatula tip of Raney nickel is added and the reaction mixture is stirred in the autoclave under a hydrogen pressure of 4 bar for 16 h. The catalyst is filtered off through Celite® and the filtrate is freed in vacuo of all the volatile constituents. 0.99 g of the aniline are obtained [MS-ESI+: 351 (M+H)$^+$].

This amount is dissolved in 5 mL MeOH and a solution of 0.35 g (14.6 mmol, 2.9 eq) lithium hydroxide in 10 mL water is added. After 16 h stirring at RT the reaction mixture is concentrated in vacuo, the residue is taken up in 10 mL water and acidified with aqueous hydrochloric acid. The precipitate is filtered off, washed with water and dried in vacuo. 392 mg 2-ethoxy-4-amino-benzoic acid are obtained.

C-2d 4-[4-((1R,2S)-2-isopropylcarbamoyl-cyclopentylamino)-5-methyl-pyrimidin-2-yl-amino]-benzoic acid

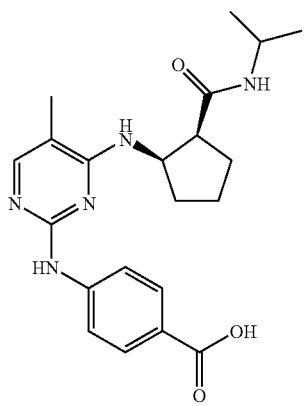 [SMILES: Cc1cnc(Nc2ccc(C(=O)O)cc2)nc1N[C@@H]1CCC[C@@H]1C(=O)NC(C)C]

956 mg (3.2 mmol, 1 eq) C-1d are dissolved in 5.4 mL 1-butanol and this solution is combined with 446 mg (3.2 mmol, 1 eq) 4-amino-benzoic acid. After the addition of 105 µL (0.42 mmol, 0.13 eq) dioxanic hydrochloric acid (4 M), the mixture is refluxed for 2 h with stirring. After cooling the precipitate formed is filtered off and washed with 2 mL cold 1-butanol. After drying in vacuo 1.15 g C-2d are obtained and used without further purification.

MS-ESI+: 398 (M+H)+

C-2e 4-[4-((1R,2S)-2-isopropylcarbamoyl-cyclopentylamino)-5-chloro-pyrimidin-2-yl-amino]-benzoic acid

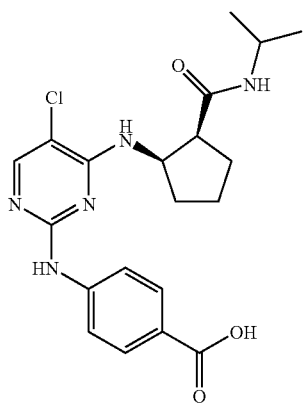 [SMILES: CC(C)NC(=O)[C@H]1CCC[C@H]1Nc1nc(Nc2ccc(C(=O)O)cc2)ncc1Cl]

C-2e is synthesised analogously to the preparation of C-2d.

D-1a) (±)-4-[4-((1R*,2S*)-2-amino-cyclohexylamino)-5-trifluoromethyl-pyrimidin-2-ylamino]-N-methyl-N-(1-methyl-piperidin-4-yl)-benzamide

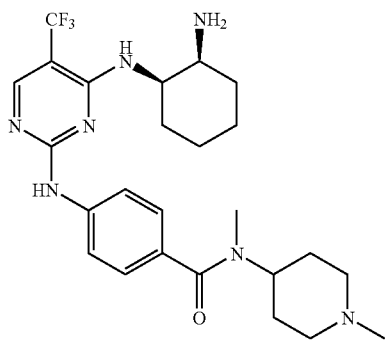 [SMILES: CN1CCC(N(C)C(=O)c2ccc(Nc3ncc(C(F)(F)F)c(N[C@@H]4CCCC[C@@H]4N)n3)cc2)CC1]

500 mg (1.17 mmol, 1 eq) B-3a are dissolved in 5 mL 1-butanol and combined with 760 µL (4.44 mmol, 3.8 eq) of Hünig base. Then 165 µL (1.40 mmol, 1.2 eq) cis-1,2-diaminocyclohexane are added and the reaction mixture is heated to 150° C. for 15 min in the microwave. All the volatile constituents are eliminated in vacuo and the residue is taken up in DCM. The mixture is then washed twice with dilute aqueous ammonium chloride solution, the organic phase is dried on MgSO4, the solvent is eliminated in vacuo and 477 mg D-1a are obtained.

MS-ESI+: 506 (M+H)+

D-1b) (±)-4-[4-((1R*,2S*)-2-amino-cyclopentylamino)-5-trifluoromethyl-pyrimidin-2-ylamino]-N-methyl-N-(1-methyl-piperidin-4-yl)-benzamide

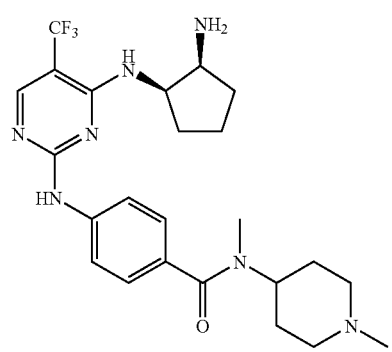

364 mg (0.85 mmol, 1 eq) B-3a is dissolved in 1 mL DMA and then 177 mg (1.02 mmol, 1.2 eq) cis-1,2-diaminocyclopentane dihydrochloride are added. The reaction mixture is combined with 1.5 mL (8.76 mmol, 10.3 eq) Hünig base and heated to 150° C. in the microwave for 20 min with stirring. Then all the volatile constituents are eliminated in vacuo and the crude product (418 mg) is further reacted without purification.

E-1) 2-methylsulphanyl-1H-pyrimidin-4-one

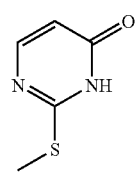

20 g (153 mmol) 2-thiouracil are suspended in 250 mL MeOH and then 8.7 g (152.9 mmol, 1 eq) sodium methoxide are added. The solution is stirred for 5 min at RT and then 12.4 mL (198.8 mmol, 1.3 eq) methyl iodide are added dropwise. The reaction mixture is stirred overnight, then poured onto water and extracted 3× with approx. 150 mL chloroform. The combined organic phases are dried on MgSO4, the solvent is eliminated in vacuo and 16 g E-1 are obtained.

E-2) 4-(6-oxo-1,6-dihydro-pyrimidin-2-ylamino)-benzoic acid

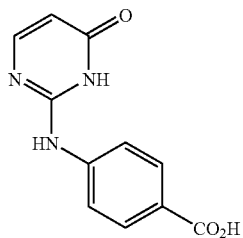 [SMILES: O=C(O)c1ccc(Nc2nccc(=O)[nH]2)cc1]

4.1 g (28.8 mmol) E-1 are dissolved in 10 mL diglyme (diethyleneglycol dimethylether) and this solution is combined with 4.79 g (34.6 mmol, 1.2 eq) 4-aminobenzoic acid. The reaction mixture is refluxed for 16 h. After cooling to RT the precipitate is suction filtered, washed with a little diglyme, then with diethyl ether and dried in vacuo. 5.27 g E-2 are obtained.

MS-ESI$^+$: 232 (M+H)$^+$

E-3) 4-(5-bromo-6-oxo-1,6-dihydro-pyrimidin-2-ylamino)-benzoic acid

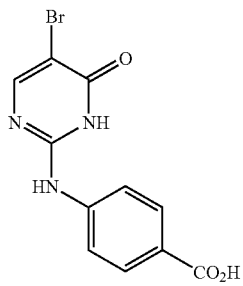 [SMILES: O=C(O)c1ccc(Nc2ncc(Br)c(=O)[nH]2)cc1]

9 g (38.9 mmol) E-2 are placed in 10 mL acetic acid and a solution of 2.1 mL (40.9 mmol, 1.05 eq) bromine in 50 mL acetic acid is added dropwise thereto and the mixture is stirred for approx. 1 h at RT. The reaction mixture is stirred into 800 mL water, the precipitate is suction filtered and the precipitate obtained is washed with water and dried in vacuo. 11.5 g E-3 are obtained.

$R_f$=0.27 (silica gel, EE:MeOH 7:3)
MS-ESI$^+$: 309/311 (M+H)$^+$

E-5) 4-(4-chloro-5-bromo-pyrimidin-2-ylamino)-benzoyl Chloride and

E-4) 4-(4-chloro-5-bromo-pyrimidin-2-ylamino)-benzoic acid

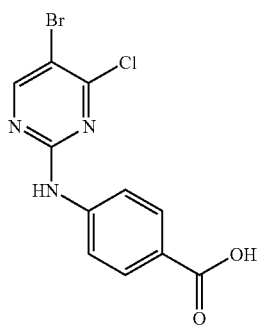

E-4

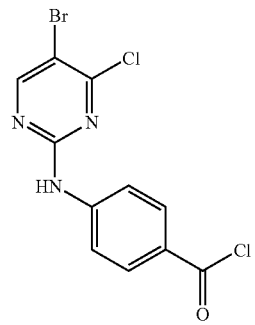

E-5

5 g (16.1 mmol) E-3 are suspended in 70 mL phosphorus oxychloride and refluxed for 1 h with stirring. The reaction mixture is added dropwise to 600 mL water/ice with vigorous stirring, stirred for another 30 min and the crude acid E-4 is filtered off. This is dried in vacuo and used further without purification.

In order to prepare the acid chloride 2.7 g (8.2 mmol) of the crude acid are dissolved in 20 mL toluene and 715 µL (9.9 mmol, 1.2 eq) thionyl chloride are added. The reaction mixture is stirred for 1 h at reflux temperature and then evaporated down in vacuo. After drying in vacuo 2.9 g E-5 is obtained.

E-6) 4-(5-bromo-4-chloro-pyrimidin-2-ylamino)-N-methyl-N-(1-methyl-piperidin-4-yl)-benzamide

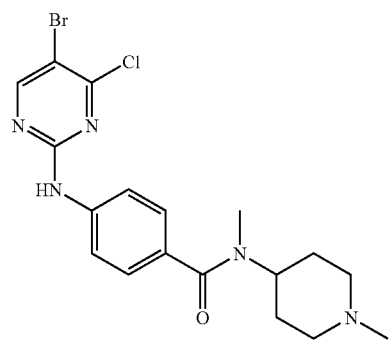 [SMILES: CN1CCC(N(C)C(=O)c2ccc(Nc3ncc(Br)c(Cl)n3)cc2)CC1]

500 mg (1.44 mmol, 1 eq) E-5 are dissolved in 20 mL THF and mixed with 370 µL (2.16 mmol, 1.5 eq) Hünig base, followed by 209 µL (1.44 mmol, 1 eq) 1-methyl-4-(methylamino)-piperidine. The reaction mixture is stirred for 16 h at RT and then poured into 250 mL water. It is extracted 4 times with 100 mL EE. The combined organic phases are dried on MgSO$_4$ and the solvent is eliminated in vacuo. 418 mg E-6 are obtained.

$R_f$=0.64 (silica gel, DCM:MeOH:NH$_3$ 5:1:0.1)
MS-ESI$^+$: 440/442 (M+H)$^+$

E-7a) (1S,2R)-2-(5-bromo-2-{4-[methyl-(1-methyl-piperidin-4-yl)-carbamoyl]-phenylamino}-pyrimidin-4-ylamino)-cyclopentanecarboxylic acid

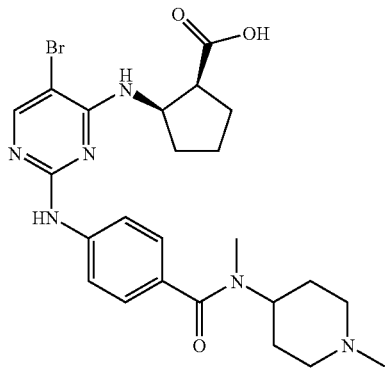 [SMILES: CN1CCC(N(C)C(=O)c2ccc(Nc3ncc(Br)c(N[C@@H]4CCC[C@@H]4C(=O)O)n3)cc2)CC1]

1.91 g (4.35 mmol, 1 eq) E-6 are suspended in 5 mL DMA and mixed with 1.5 mL (8.7 mmol, 2 eq) Hünig base. 865 mg (5.22 mmol, 1.2 eq) (1S,2R)-2-aminocyclopentane-carboxylic acid are added to the solution and the reaction mixture is stirred for 120 min at 120° C. (CEM microwave, 100 W). The reaction mixture is evaporated down, stirred in approx. 200 mL water and extracted 3 times with 100 mL EE. The combined organic phases are dried on MgSO$_4$ and evaporated down in vacuo. Then RP gel is added, the volatile constituents are eliminated in vacuo, the product is purified by column chromatography through an RP phase and isolated (water/MeCN (+0.2% HCOOH in each case) from 92/8 to 79/21 in 20 min). Corresponding product fractions are combined and freed from the solvent by freeze-drying. 1.26 g E-7a are obtained.

MS-ESI$^+$: 531/533 (M+H)$^+$

E-7b) (±)-(1S*,2R*)-2-(5-bromo-2-[4-[methyl-(1-methyl-piperidin-4-yl)-carbamoyl]-phenylamino]-pyrimidin-4-ylamino)-cyclopentanecarboxylic acid

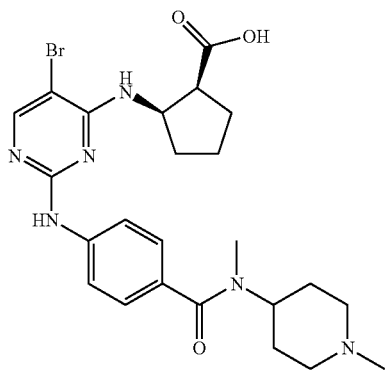 [SMILES: CN1CCC(N(C)C(=O)c2ccc(Nc3ncc(Br)c(N[C@@H]4CCC[C@@H]4C(=O)O)n3)cc2)CC1]

E-7b is prepared analogously to E-7a using racemic cis-2-amino-cyclopentanecarboxylic acid.

Example 1

4-[4-((1R,2S)-2-isopropylcarbamoyl-cyclopentylamino)-5-trifluoromethyl-pyrimidin-2-ylamino]-N-methyl-N-(1,2,2,6,6-pentamethyl-piperidin-4-yl)-benzamide 100 mg (0.22 mmol) A-5a are dissolved in 2 mL DMF, 190 µL (1.11 mmol, 5 eq) Hünig base and 112 mg (0.35 mmol, 1.6 eq) TBTU are added. The reaction mixture is stirred for 30 min at RT and then 88 mg (0.38 mmol, 1.7 eq, content 80%) methyl-(1,2,2,6,6-pentamethyl-piperidin-4-yl)-amine are added dropwise. The mixture is stirred for 2 days at RT, the reaction mixture is filtered through basic aluminium oxide, then combined with RP gel, the volatile constituents are eliminated in vacuo and the product is purified by column chromatography through an RP phase and isolated (water/MeCN (+0.2% HCOOH in each case) from 80/20 to 55/45 in 15 min). Corresponding product fractions are combined, mixed with concentrated hydrochloric acid, freed from the solvent by freeze-drying and 61 mg of compound 1 are obtained as the hydrochloride.

Examples 3, 5 and 8 are prepared analogously. A-5c is used in the case of the racemic Examples 2 and 7 and A-5b is used instead of A-5a in the case of Example 4. Examples 9-10 are also prepared analogously to general Synthesis scheme A using the benzoic acids obtained by hydrogenolysis from A-4-b and A-4-c (analogously to the method described for A-5a), Example 84 is prepared using A-5d.

Example 6

N-isopropyl-4-[4-((1R,2S)-2-isopropylcarbamoyl-cyclopentylamino)-5-trifluoromethyl-pyrimidin-2-ylamino]-N-(1-methyl-piperidin-4-yl)-benzamide This is synthesised as described for Example 1 by amide coupling starting from A-5a. In this process tert-butyl 4-iso-propylamino-piperidine-1-carboxylate is used as the amine component. The coupling product is then freed from the protective group and methylated as follows.

98 mg of the coupling product from A-5a and tert-butyl 4-isopropylamino-piperidine-1-carboxylate are stirred in 2 mL DCM and 2 mL trifluoroacetic acid for 2 h at RT. 10 mL water are added and adjusted to pH 10 with sodium carbonate. The mixture is extracted 3 times with 15 mL DCM, the organic phase is dried on MgSO$_4$, the volatile constituents are eliminated in vacuo and the crude product (50 mg) is further reacted directly. For this purpose 50 mg (0.08 mmol, 1 eq) of the product are placed in 1 mL DMA, 13 µL formaldehyde (37% in water, 0.16 mmol, 2 eq) are added and the mixture is stirred for 20 min at RT. 5 µL glacial acetic acid are added dropwise, then 92 mg (0.43 mmol, 5 eq) sodium trisacetoxyborohydride are added batchwise and the mixture is stirred overnight at RT. It is combined with 20 mL water, 10 mL saturated aqueous NaHCO$_3$ solution is slowly added, the mixture is extracted 3 times with 10 mL DCM and dried on MgSO$_4$. Then RP gel is added, the volatile constituents are eliminated in vacuo and the product is purified by column chromatography through an RP phase and isolated (water/MeCN 82/18 (+0.2% HCOOH in each case) to 60/40 in 15 min). Corresponding product fractions are combined, mixed with concentrated hydrochloric acid, freed from the solvent by freeze-drying and 7 mg of compound 6 are obtained as the hydrochloride.

Example 12

4-{4-[(1R*,2S*)-2-((R)-2-hydroxy-1-methyl-ethyl-carbamoyl)-cyclopentylamino]-5-trifluoromethyl-pyrimidin-2-ylamino}-N-methyl-N-(1-methyl-piperidin-4-yl)-benzamide 80 mg (0.15 mmol, 1 eq) B-4-c are dissolved in 3 mL THF and combined with 264 µL (1.54 mmol, 10 eq) Hünig base. 69 mg (0.22 mmol, 1.5 eq) TBTU are added to this solution and it is stirred for 40 min. at RT. The suspension is combined with a few drops of DMF, whereupon all the undissolved constituents go into solution. Then 17 mg (0.23 mmol, 1.5 eq)

D-alaninol are added and the mixture is stirred for 16 h at RT. Then the reaction mixture is combined with 10 mL RP gel and all the volatile constituents are eliminated in vacuo. It is purified by chromatography through an RP-phase (MeCN/water 15/85+(0.2% HCOOH in each case) to 30/70 in 15 min). After the combining of the product fractions, the addition of hydrochloric acid (4 M in dioxane) and freeze-drying, 85 mg of the hydrochloride of 12 is obtained.

Examples 13-83, 85-108, 125, 126 and 127 are prepared analogously using the corresponding carboxylic acid derivatives B-4 and amine components, while O-(7-azabenzotriazol-1-yl)-N,N,N'N'-tetramethyluronium hexafluorophosphate may optionally be used instead of TBTU as coupling reagent.

Examples 128-130 are prepared according to general Synthesis scheme A, the synthesis sequence starting with the reaction of A-1a with benzyl 4-amino-3-methoxy-benzoate.

Example 110

(±)-4-[4-((1R*,2S*)-2-acetylamino-cyclohexylamino)-5-trifluoromethyl-pyrimidin-2-ylamino]-N-methyl-N-(1-methyl-piperidin-4-yl)-benzamide 50 mg (0.1 mmol, 1 eq) D-1a (Example 109) are dissolved in 0.5 mL NMP, then 17 µL (0.12 mmol, 1.2 eq) triethylamine are added and 9 µL (0.12 mmol, 1.2 eq) acetyl chloride are added dropwise to this solution. The reaction mixture is stirred for 16 h at RT, combined with RP gel and all the volatile constituents are eliminated in vacuo. It is purified by chromatography through an RP phase. 30 mg of compound 110 are obtained.

Examples 112-114 are prepared analogously starting from D-1a and the corresponding carboxylic acid chlorides. Examples 120-123 are prepared analogously starting from D-1b (Example 124) by acylation under the conditions described for Example 110. This method of synthesis is also used for synthesising the compounds III and 115, while in this case the reaction is carried out with the corresponding sulphonic acid chlorides. In the case of Example 116, a urea derivative, D-1a is reacted with N,N-dimethylcarbamoyl chloride under the conditions described for Example 110.

Example 117

117 is prepared analogously to the preparation of B-4-a starting from B-3a and 3-endo-aminobicyclo(2,2,1)-hept-5-en-2-endo-carboxylic acid using 1 butanol as solvent.

Example 118

118 is prepared analogously to the preparation of B-4-a starting from B-3a and 2-adamantanamine-hydrochloride.

Example 119

This is synthesised analogously to Example 12 using Example 117 as educt. After the amide coupling has taken place the unsaturated intermediate compound is hydrogenated in THF with stirring at RT by reaction with formic acid (11 eq) in the presence of catalytic amounts of Pd/C and in this way Example 119 is obtained.

Example 132

2-ethoxy-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide 46 mg (0.09 mmol, 1 eq) C-2a are dissolved in 1.2 mL DMF and then 81 µL (0.47 mmol, 5 eq) Hünig base and 42 mg (0.13 mmol, 1.4 eq) TBTU are added. The mixture is stirred for 5 min at RT and then 21 µL (0.14 mmol, 1.5 eq) 1-methyl-4-(methylamino)-piperidine are added dropwise. The reaction mixture is stirred for 2 h at RT and then purified directly by chromatography through an RP phase. (Water/MeCN (+0.2% HCOOH in each case) from 83/17 to 65/35% in 10 min). After the combining of the product fractions, the addition of 500 µL hydrochloric acid (4 M in dioxane) and freeze-drying, 47 mg of the hydrochloride of 132 is obtained.

Examples 131 and 133-135 are prepared analogously by amide coupling from the corresponding acid derivatives C-2, which are obtained from C-1a and the correspondingly substituted 4-aminobenzoic acids by nucleophilic aromatic substitution (described by way of example for the synthesis of $C_{1-2}$a).

Example 136

(±)-4-[4-((1R*,2S*)-2-isopropylcarbamoyl-cyclobutylamino)-5-trifluoromethyl-pyrimidin-2-ylamino]-N-methyl-N-(1-methyl-piperidin-4-yl)-benzamide 150 mg (0.35 mmol, 1 eq) B-3a are dissolved in 1.3 mL EtOH and 150 µL (0.88 mmol, 2.5 eq) Hünig base are added. After the addition of 100 mg (0.42 mmol, 1.2 eq) (±)-cis-2-aminocyclobutanecarboxylic acid isopropylamide the reaction mixture is heated to 70° C. and stirred for 16 h at this temperature. The reaction mixture is then combined with 10 mL RP gel and all the volatile constituents are eliminated in vacuo. It is purified by chromatography through an RP phase (MeCN/water from 10/90 to 30/70 in 15 min). After the combining of the product fractions, the addition of 100 µL dioxanic hydrochloric acid (4 M) and freeze-drying, 86 mg of the hydrochloride of 136 is obtained.

Example 139

(±)-4-[5-bromo-4-[(1R*,2S*)-2-cyclopropylcarbamoyl]-cyclopentylamino)-pyrimidin-2-ylamino]-N-methyl-N-(1-methyl-piperidin-4-yl)-benzamide 55 mg (0.10 mmol, 1 eq) E-7b are dissolved in 1 mL DMF, 88 µL (0.5 mmol, 5 eq) Hünig base and 46 mg (0.14 mmol, 1.4 eq) TBTU are added. The reaction mixture is stirred for 10 min at RT and then 11 mg (0.15 mmol, 1.5 eq) cyclopropylamine are added dropwise. The mixture is stirred for 2 days at RT, the reaction mixture is filtered through basic aluminium oxide, then combined with RP gel, the volatile constituents are eliminated in vacuo and the product is purified by column chromatography through an RP phase and isolated (water/MeCN (+0.2% HCOOH in each case) from 88/12% to 75/25 in 10 min). Corresponding product fractions are combined, mixed with 100 µL dioxanic hydrochloric acid (4 M), freed from the solvent by freeze-drying and 25 mg of the compound 139 are obtained as the hydrochloride.

Examples 137, 138, 140-144 and 146 are prepared analogously, while in the case of 142, 143 and 146 the chiral starting compound E-7a is used.

Example 145/147

145 and 147 are synthesised analogously to the preparation of Example 1 by amide coupling of C-2d and C-2e, resp., with 1-methyl-4-(methylamino)-piperidine.

Examples 1-147
| Ex. No. | structure | method of synthesis | HPLC RT [min] | MS (ESI⁺) [M + H]⁺ | UV$_{max}$ [nm] |
|---|---|---|---|---|---|
| 1 | 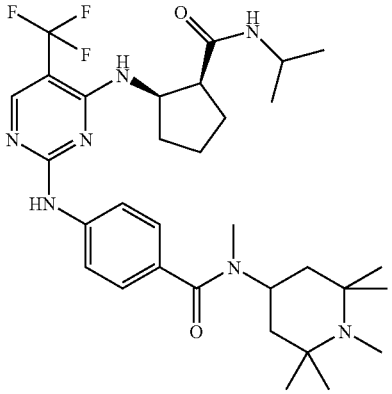 [SMILES: CC(C)NC(=O)[C@H]1CCC[C@H]1Nc1nc(Nc2ccc(C(=O)N(C)C3CC(C)(C)N(C)C(C)(C)C3)cc2)ncc1C(F)(F)F] | A | 1.52 | 618 | 278 |
| 2 | 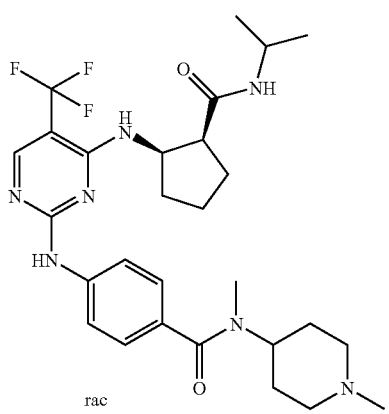 [SMILES: CC(C)NC(=O)[C@H]1CCC[C@H]1Nc1nc(Nc2ccc(C(=O)N(C)C3CCN(C)CC3)cc2)ncc1C(F)(F)F] | A | 1.42 | 562 | 278 |
| 3 | 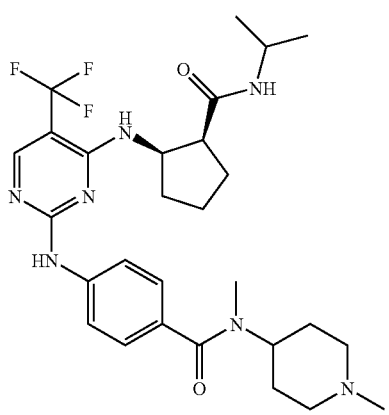 [SMILES: CC(C)NC(=O)[C@H]1CCC[C@H]1Nc1nc(Nc2ccc(C(=O)N(C)C3CCN(C)CC3)cc2)ncc1C(F)(F)F] | A | 1.41 | 562 | 278 |

-continued

| Ex. No. | structure | method of synthesis | HPLC RT [min] | MS (ESI+) [M + H]+ | UV_max [nm] |
| --- | --- | --- | --- | --- | --- |
| 4 | 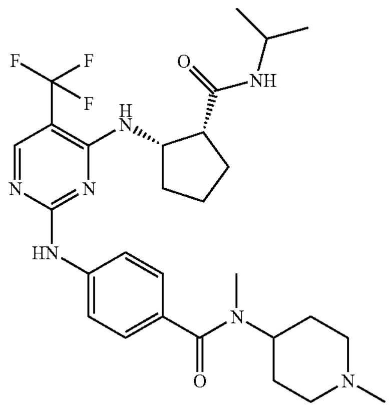 [SMILES: CC(C)NC(=O)[C@@H]1CCC[C@@H]1Nc1nc(Nc2ccc(C(=O)N(C)C3CCN(C)CC3)cc2)ncc1C(F)(F)F] | A | 1.45 | 562 | 278 |
| 5 | 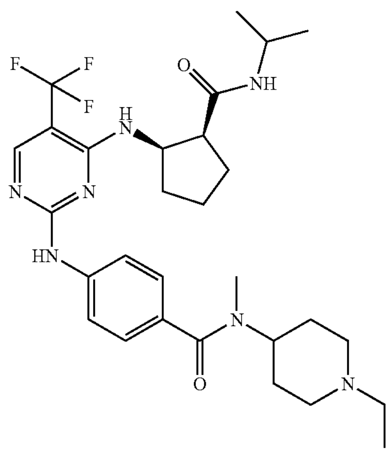 [SMILES: CCN1CCC(N(C)C(=O)c2ccc(Nc3ncc(C(F)(F)F)c(N[C@@H]4CCC[C@@H]4C(=O)NC(C)C)n3)cc2)CC1] | A | 1.44 | 576 | 2178 |
| 6 | 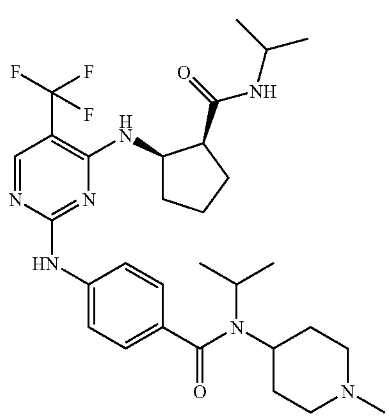 [SMILES: CC(C)NC(=O)[C@H]1CCC[C@H]1Nc1nc(Nc2ccc(C(=O)N(C(C)C)C3CCN(C)CC3)cc2)ncc1C(F)(F)F] | A | 1.58 | 590 | 274 |

-continued
| Ex. No. | structure | method of synthesis | HPLC RT [min] | MS (ESI+) [M + H]+ | UV_max [nm] |
|---|---|---|---|---|---|
| 7 | 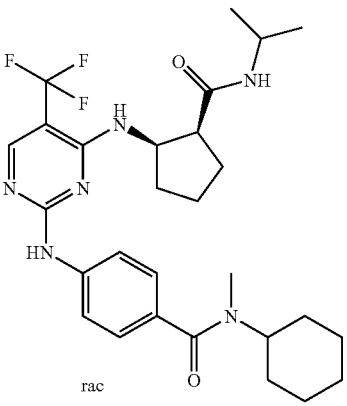 [SMILES: CC(C)NC(=O)[C@H]1CCC[C@H]1Nc1nc(Nc2ccc(C(=O)N(C)C3CCCCC3)cc2)ncc1C(F)(F)F] rac | A | 2.17 | 547 | 277 |
| 8 | 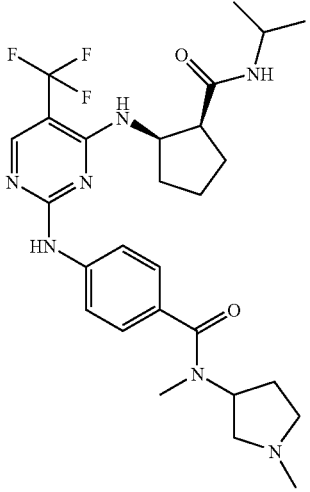 [SMILES: CC(C)NC(=O)[C@H]1CCC[C@H]1Nc1nc(Nc2ccc(C(=O)N(C)C3CCN(C)C3)cc2)ncc1C(F)(F)F] | A | 1.46 | 548 | 278 |
| 9 | 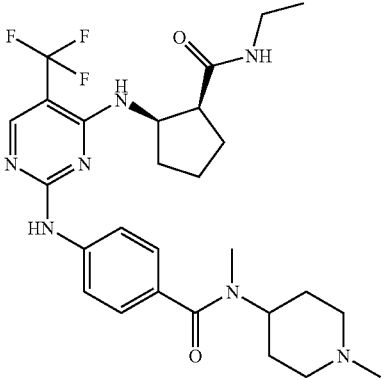 [SMILES: CCNC(=O)[C@H]1CCC[C@H]1Nc1nc(Nc2ccc(C(=O)N(C)C3CCN(C)CC3)cc2)ncc1C(F)(F)F] | A | 1.36 | 548 | 276 |

-continued

| Ex. No. | structure | method of synthesis | HPLC RT [min] | MS (ESI+) [M + H]+ | UV_max [nm] |
|---|---|---|---|---|---|
| 10 | 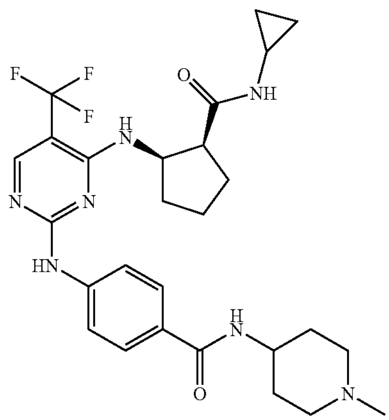 [SMILES: CN1CCC(NC(=O)c2ccc(Nc3ncc(C(F)(F)F)c(N[C@@H]4CCC[C@@H]4C(=O)NC4CC4)n3)cc2)CC1] | A | | 546 | 284 |
| 12 | 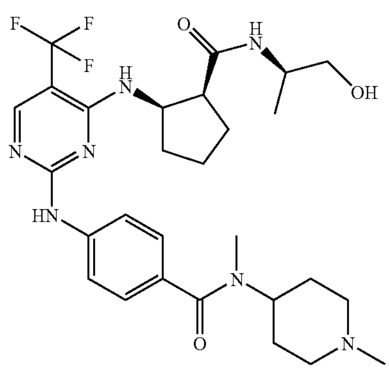 [SMILES: C[C@H](CO)NC(=O)[C@H]1CCC[C@H]1Nc1nc(Nc2ccc(C(=O)N(C)C3CCN(C)CC3)cc2)ncc1C(F)(F)F] | B | 1.26 | 578 | 274 |
| 13 | rac | B | 1.51 | 576 | 278 |

| Ex. No. | structure | method of synthesis | HPLC RT [min] | MS (ESI⁺) [M + H]⁺ | UV$_{max}$ [nm] |
|---|---|---|---|---|---|
| 14 | 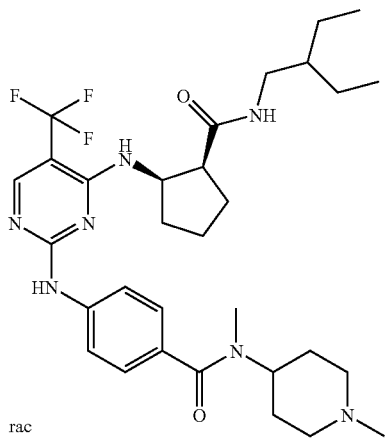 [SMILES: CCC(CC)CNC(=O)[C@H]1CCC[C@H]1Nc1nc(Nc2ccc(C(=O)N(C)C3CCN(C)CC3)cc2)ncc1C(F)(F)F] rac | B | 1.68 | 604 | 278 |
| 15 | 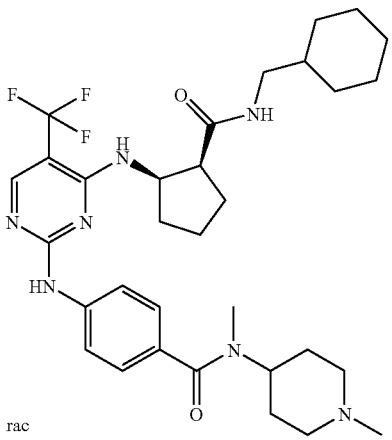 [SMILES: CN1CCC(N(C)C(=O)c2ccc(Nc3ncc(C(F)(F)F)c(N[C@@H]4CCC[C@@H]4C(=O)NCC4CCCCC4)n3)cc2)CC1] rac | B | 1.68 | 616 | 278 |
| 16 | 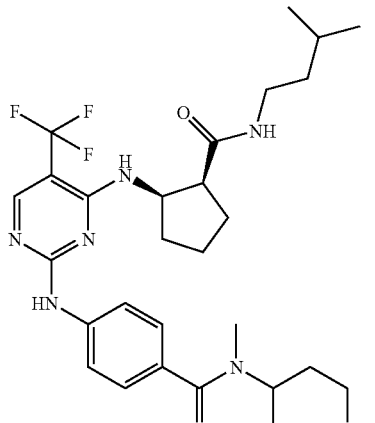 rac | B | 1.60 | 590 | 278 |

-continued

| Ex. No. | structure | method of synthesis | HPLC RT [min] | MS (ESI⁺) [M + H]⁺ | UV$_{max}$ [nm] |
|---|---|---|---|---|---|
| 17 | 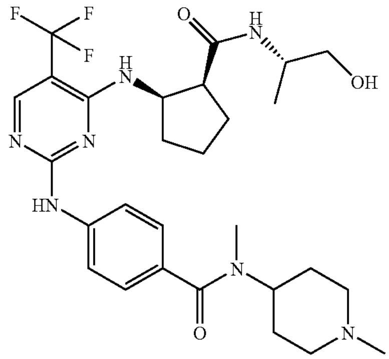 [SMILES: C[C@@H](CO)NC(=O)[C@H]1CCC[C@H]1Nc1nc(Nc2ccc(C(=O)N(C)C3CCN(C)CC3)cc2)ncc1C(F)(F)F] | B | | 578 | 274 |
| 18 | rac | B | 1.52 | 616 | 278 |
| 19 | rac | B | 1.37 | 560 | 278 |

-continued
| Ex. No. | structure | method of synthesis | HPLC RT [min] | MS (ESI+) [M + H]+ | UV max [nm] |
|---|---|---|---|---|---|
| 20 | 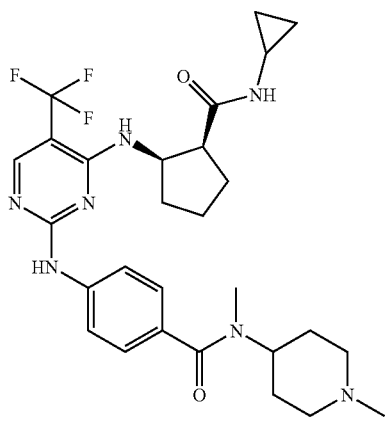 | B | 1.36 | 560 | 278 |
| 21 | 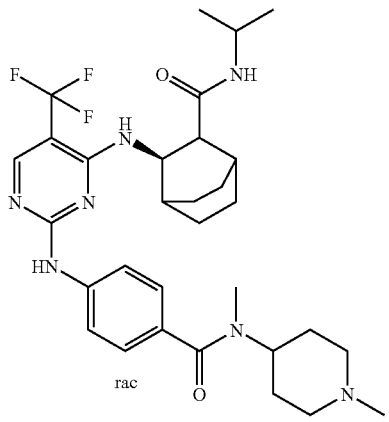 [SMILES: CC(C)NC(=O)C1C2CCC(CC2)[C@H]1Nc1nc(Nc2ccc(C(=O)N(C)C3CCN(C)CC3)cc2)ncc1C(F)(F)F] | B | 1.59 | 602 | 278 |
| 22 | 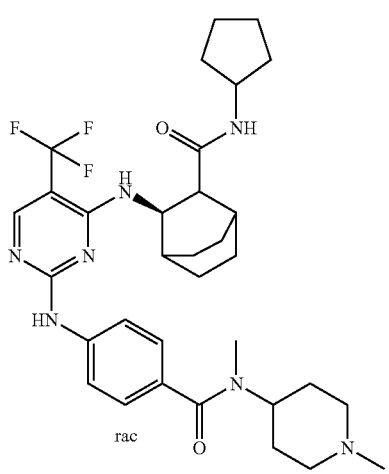 [SMILES: CN1CCC(N(C)C(=O)c2ccc(Nc3ncc(C(F)(F)F)c(N[C@@H]4C5CCC(CC5)C4C(=O)NC4CCCC4)n3)cc2)CC1] | B | 1.69 | 628 | 278 |

-continued

| Ex. No. | structure | method of synthesis | HPLC RT [min] | MS (ESI+) [M + H]+ | UV$_{max}$ [nm] |
|---|---|---|---|---|---|
| 23 | 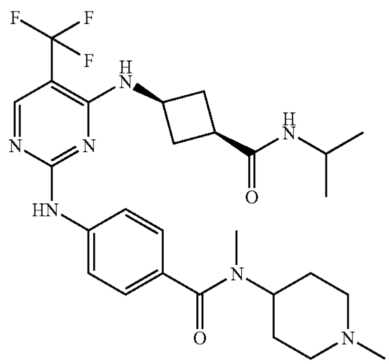 [SMILES: CC(C)NC(=O)[C@H]1C[C@@H](Nc2nc(Nc3ccc(C(=O)N(C)C4CCN(C)CC4)cc3)ncc2C(F)(F)F)C1] | B | | 548 | 278 |
| 24 | 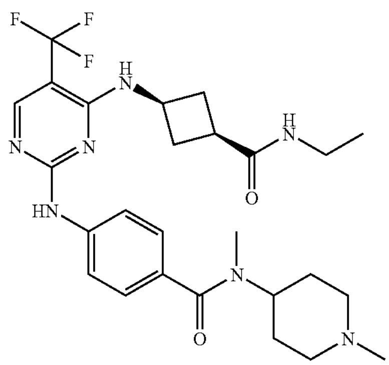 [SMILES: CCNC(=O)[C@H]1C[C@@H](Nc2nc(Nc3ccc(C(=O)N(C)C4CCN(C)CC4)cc3)ncc2C(F)(F)F)C1] | B | | 534 | 274 |
| 25 | 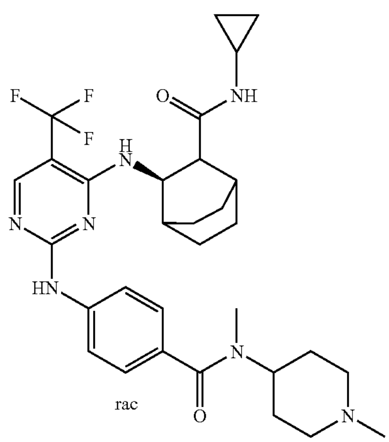 [SMILES: CN1CCC(N(C)C(=O)c2ccc(Nc3ncc(C(F)(F)F)c(N[C@@H]4C5CCC(CC5)C4C(=O)NC4CC4)n3)cc2)CC1] | B | 1.54 | 600 | 278 |
| 26 | 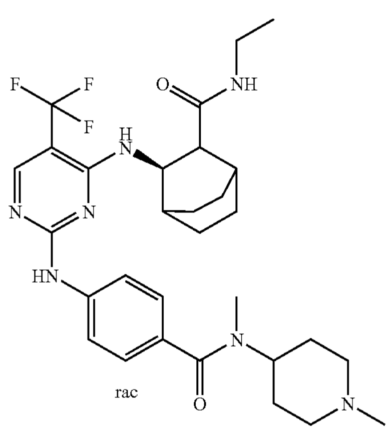 [SMILES: CCNC(=O)C1C2CCC(CC2)[C@H]1Nc1nc(Nc2ccc(C(=O)N(C)C3CCN(C)CC3)cc2)ncc1C(F)(F)F] | B | 1.53 | 588 | 278 |

| Ex. No. | structure | method of synthesis | HPLC RT [min] | MS (ESI+) [M + H]+ | UVmax [nm] |
|---|---|---|---|---|---|
| 27 | 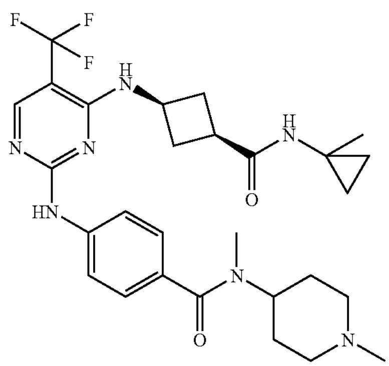 [SMILES: CN1CCC(N(C)C(=O)c2ccc(Nc3ncc(C(F)(F)F)c(N[C@H]4C[C@@H](C(=O)NC5(C)CC5)C4)n3)cc2)CC1] | B | 1.33 | 560 | 278 |
| 28 | 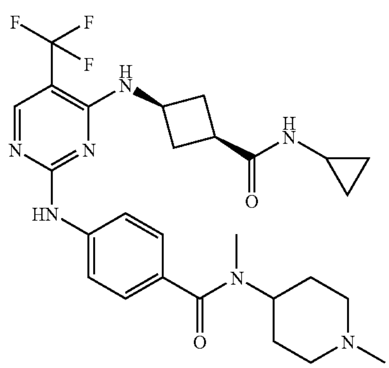 [SMILES: CN1CCC(N(C)C(=O)c2ccc(Nc3ncc(C(F)(F)F)c(N[C@H]4C[C@@H](C(=O)NC5CC5)C4)n3)cc2)CC1] | B | 1.43 | 546 | 274 |
| 29 | 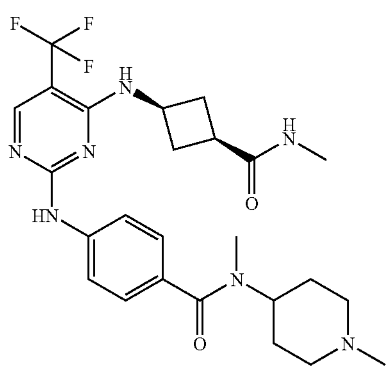 [SMILES: CNC(=O)[C@H]1C[C@@H](Nc2nc(Nc3ccc(C(=O)N(C)C4CCN(C)CC4)cc3)ncc2C(F)(F)F)C1] | B | 1.05 | 520 | 274 |
| 30 | 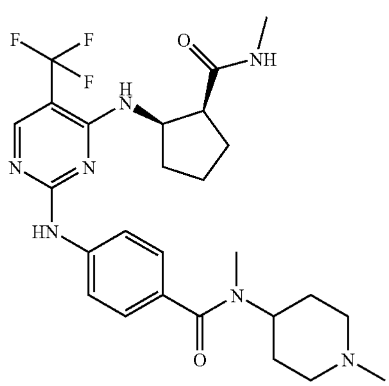 [SMILES: CNC(=O)[C@H]1CCC[C@H]1Nc1nc(Nc2ccc(C(=O)N(C)C3CCN(C)CC3)cc2)ncc1C(F)(F)F] | B | | 534 | |

| Ex. No. | structure | method of synthesis | HPLC RT [min] | MS (ESI+) [M + H]+ | UVmax [nm] |
|---|---|---|---|---|---|
| 31 | 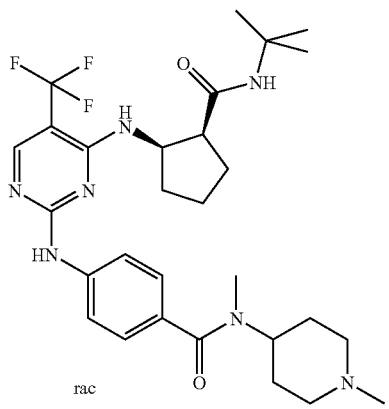 [SMILES: CN1CCC(N(C)C(=O)c2ccc(Nc3ncc(C(F)(F)F)c(N[C@@H]4CCC[C@@H]4C(=O)NC(C)(C)C)n3)cc2)CC1] rac | B | | 576 | 278 |
| 32 | 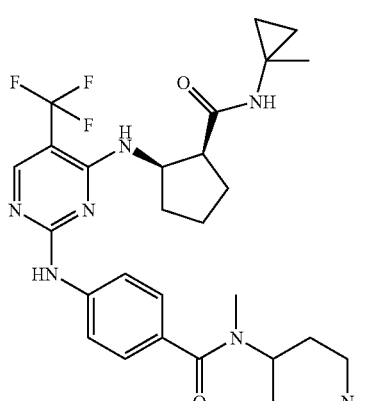 rac | B | | 574 | 278 |
| 33 | 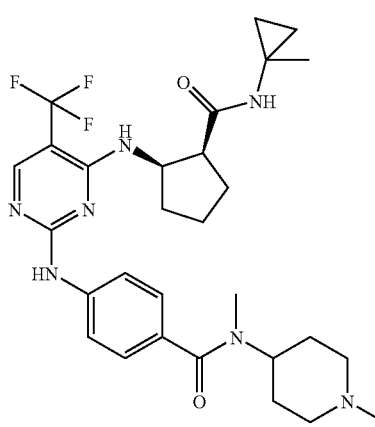 | B | 1.38 | 574 | 278 |

| Ex. No. | structure | method of synthesis | HPLC RT [min] | MS (ESI+) [M + H]+ | UV_max [nm] |
|---|---|---|---|---|---|
| 34 | 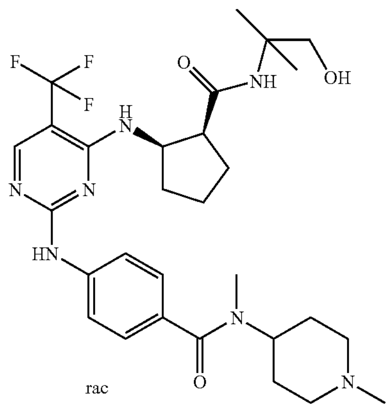 [SMILES: CN1CCC(N(C)C(=O)c2ccc(Nc3ncc(C(F)(F)F)c(N[C@@H]4CCC[C@@H]4C(=O)NC(C)(C)CO)n3)cc2)CC1] | B | | 592 | 274 |
| 35 | 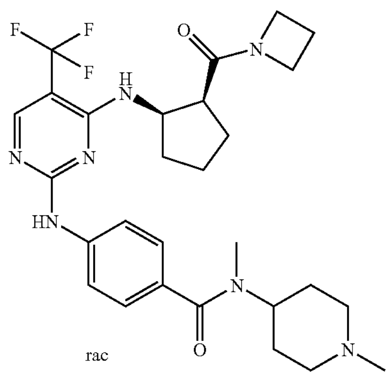 [SMILES: CN1CCC(N(C)C(=O)c2ccc(Nc3ncc(C(F)(F)F)c(N[C@@H]4CCC[C@@H]4C(=O)N4CCC4)n3)cc2)CC1] | B | 1.33 | 560 | 274 |
| 36 | 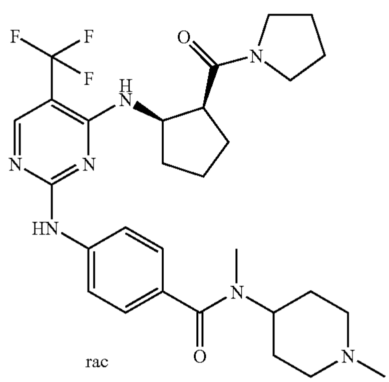 [SMILES: CN1CCC(N(C)C(=O)c2ccc(Nc3ncc(C(F)(F)F)c(N[C@@H]4CCC[C@@H]4C(=O)N4CCCC4)n3)cc2)CC1] | B | 1.41 | 574 | 278 |
| 37 | 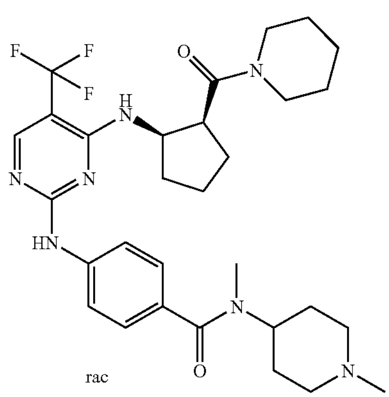 [SMILES: CN1CCC(N(C)C(=O)c2ccc(Nc3ncc(C(F)(F)F)c(N[C@@H]4CCC[C@@H]4C(=O)N4CCCCC4)n3)cc2)CC1] | B | 1.52 | 588 | 278 |

-continued
| Ex. No. | structure | method of synthesis | HPLC RT [min] | MS (ESI⁺) [M + H]⁺ | UV$_{max}$ [nm] |
|---|---|---|---|---|---|
| 38 | 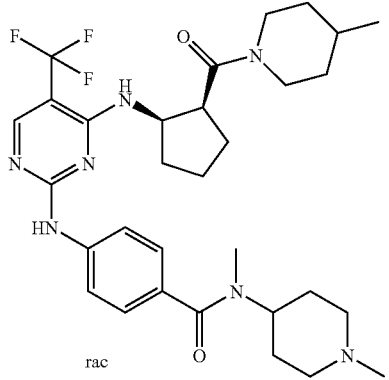 [SMILES: CC1CCN(C(=O)[C@H]2CCC[C@H]2Nc2nc(Nc3ccc(C(=O)N(C)C4CCN(C)CC4)cc3)ncc2C(F)(F)F)CC1] rac | B | 1.62 | 602 | 278 |
| 39 | 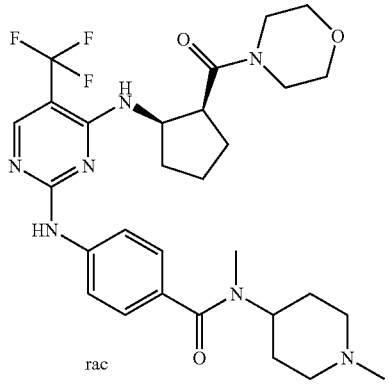 [SMILES: CN1CCC(N(C)C(=O)c2ccc(Nc3ncc(C(F)(F)F)c(N[C@@H]4CCC[C@@H]4C(=O)N4CCOCC4)n3)cc2)CC1] rac | B | 1.38 | 590 | 278 |
| 40 | 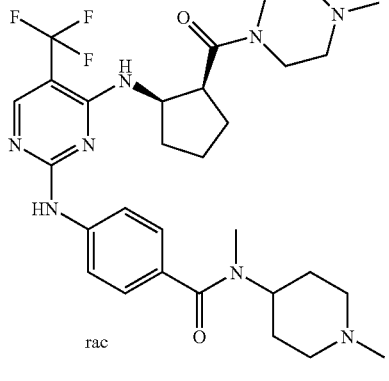 rac | B | 1.17 | 603 | 274 |
| 41 | 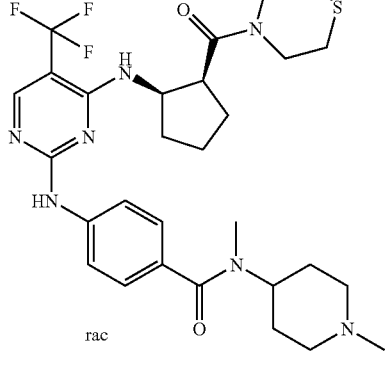 rac | B | 1.49 | 606 | 279 |

-continued
| Ex. No. | structure | method of synthesis | HPLC RT [min] | MS (ESI⁺) [M + H]⁺ | UV$_{max}$ [nm] |
|---|---|---|---|---|---|
| 42 | 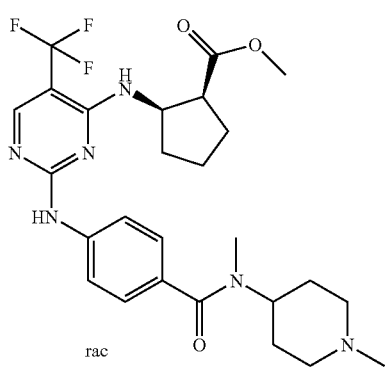 [SMILES: COC(=O)[C@H]1CCC[C@H]1Nc1nc(Nc2ccc(C(=O)N(C)C3CCN(C)CC3)cc2)ncc1C(F)(F)F] rac | B | 1.44 | 535 | 279 |
| 43 | 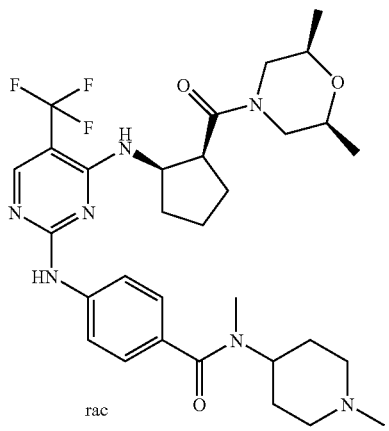 [SMILES: C[C@@H]1CN(C(=O)[C@H]2CCC[C@H]2Nc2nc(Nc3ccc(C(=O)N(C)C4CCN(C)CC4)cc3)ncc2C(F)(F)F)C[C@H](C)O1] rac | B | 1.48 | 618 | 278 |
| 44 | 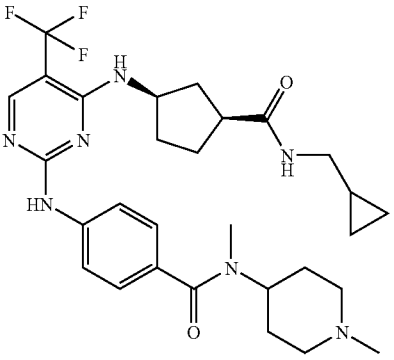 [SMILES: CN1CCC(N(C)C(=O)c2ccc(Nc3ncc(C(F)(F)F)c(N[C@@H]4CC[C@H](C(=O)NCC5CC5)C4)n3)cc2)CC1] | B | 1.36 | 574 | 274 |
| 45 | 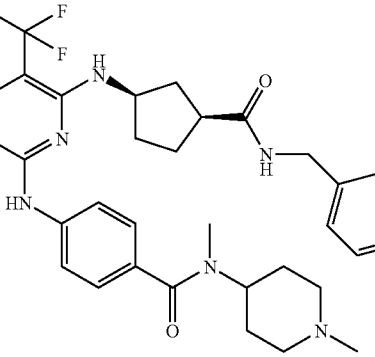 | B | 1.57 | 610 | 278 |

| Ex. No. | structure | method of synthesis | HPLC RT [min] | MS (ESI⁺) [M + H]⁺ | UV$_{max}$ [nm] |
|---|---|---|---|---|---|
| 46 | 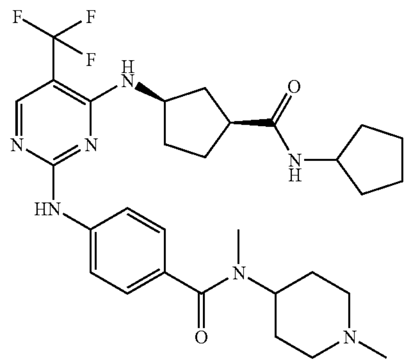 [SMILES: CN1CCC(N(C)C(=O)c2ccc(Nc3ncc(C(F)(F)F)c(N[C@@H]4CC[C@H](C(=O)NC5CCCC5)C4)n3)cc2)CC1] | B | 1.51 | 587 | 274 |
| 47 | 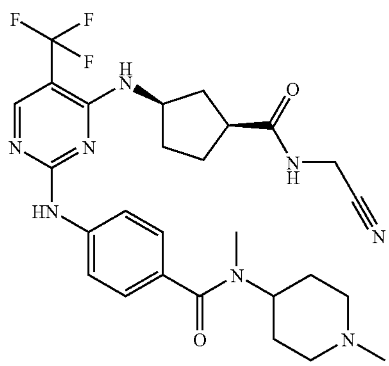 [SMILES: CN1CCC(N(C)C(=O)c2ccc(Nc3ncc(C(F)(F)F)c(N[C@@H]4CC[C@H](C(=O)NCC#N)C4)n3)cc2)CC1] | B | 1.28 | 559 | 274 |
| 48 | 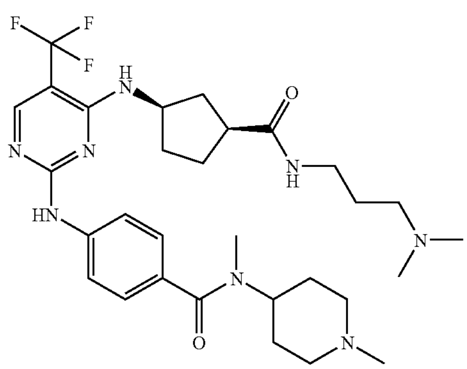 [SMILES: CN(C)CCCNC(=O)[C@H]1CC[C@@H](Nc2nc(Nc3ccc(C(=O)N(C)C4CCN(C)CC4)cc3)ncc2C(F)(F)F)C1] | B | | 605 | 274 |
| 49 | 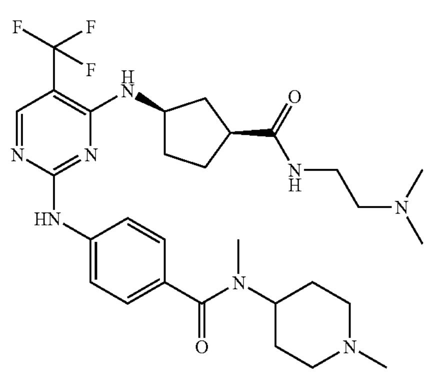 [SMILES: CN(C)CCNC(=O)[C@H]1CC[C@@H](Nc2nc(Nc3ccc(C(=O)N(C)C4CCN(C)CC4)cc3)ncc2C(F)(F)F)C1] | B | | 591 | 270 |

-continued

| Ex. No. | structure | method of synthesis | HPLC RT [min] | MS (ESI+) [M + H]+ | UV_max [nm] |
|---|---|---|---|---|---|
| 50 | 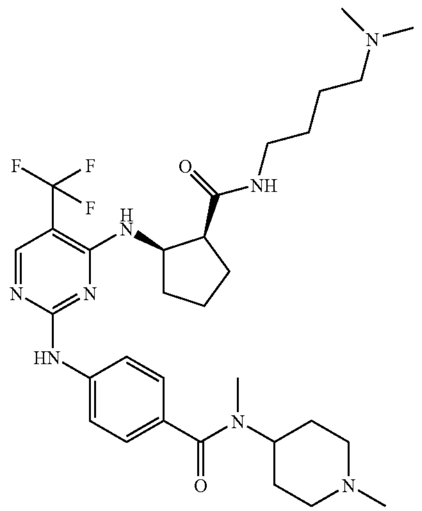 [SMILES: CN(C)CCCCNC(=O)[C@H]1CCC[C@H]1Nc1nc(Nc2ccc(C(=O)N(C)C3CCN(C)CC3)cc2)ncc1C(F)(F)F] | B | | 619 | 278 |
| 51 | 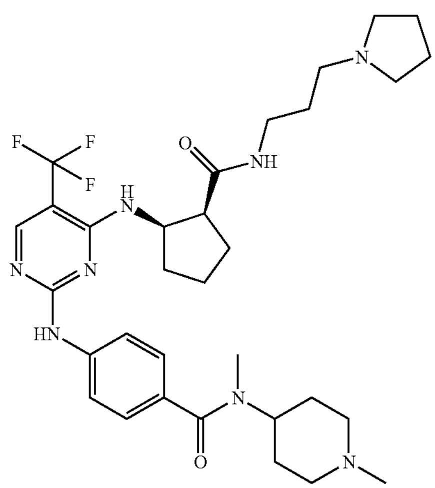 [SMILES: CN1CCC(N(C)C(=O)c2ccc(Nc3ncc(C(F)(F)F)c(N[C@@H]4CCC[C@@H]4C(=O)NCCCN4CCCC4)n3)cc2)CC1] | B | | 631 | |
| 52 | 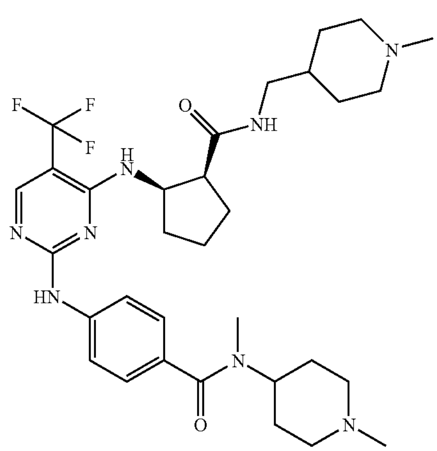 [SMILES: CN1CCC(CNC(=O)[C@H]2CCC[C@H]2Nc2nc(Nc3ccc(C(=O)N(C)C4CCN(C)CC4)cc3)ncc2C(F)(F)F)CC1] | B | | 631 | |

| Ex. No. | structure | method of synthesis | HPLC RT [min] | MS (ESI⁺) [M + H]⁺ | UV$_{max}$ [nm] |
|---|---|---|---|---|---|
| 53 | 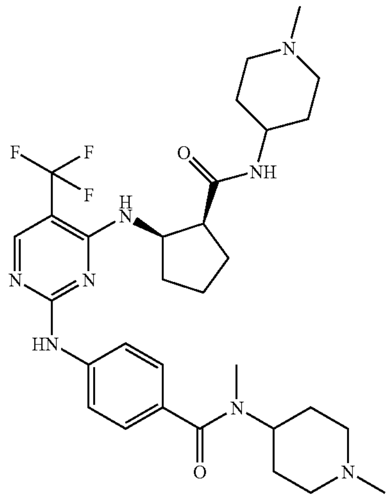 [SMILES: CN1CCC(NC(=O)[C@H]2CCC[C@H]2Nc2nc(Nc3ccc(C(=O)N(C)C4CCN(C)CC4)cc3)ncc2C(F)(F)F)CC1] | B | | 617 | |
| 54 | 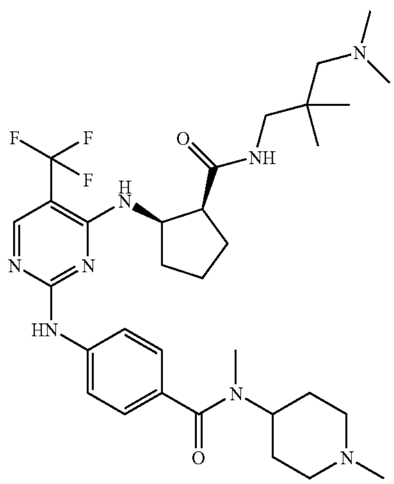 [SMILES: CN(C)CC(C)(C)CNC(=O)[C@H]1CCC[C@H]1Nc1nc(Nc2ccc(C(=O)N(C)C3CCN(C)CC3)cc2)ncc1C(F)(F)F] | B | | 633 | 271 |
| 55 | 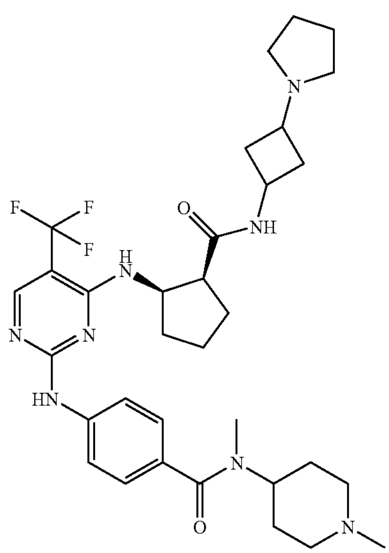 [SMILES: CN1CCC(N(C)C(=O)c2ccc(Nc3ncc(C(F)(F)F)c(N[C@@H]4CCC[C@@H]4C(=O)NC4CC(N5CCCC5)C4)n3)cc2)CC1] | B | | 643 | 276 |

-continued

| Ex. No. | structure | method of synthesis | HPLC RT [min] | MS (ESI+) [M + H]+ | UV_max [nm] |
|---|---|---|---|---|---|
| 56 | 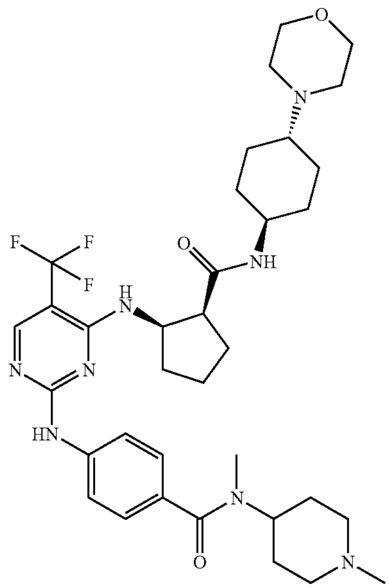 [SMILES: CN1CCC(N(C)C(=O)c2ccc(Nc3ncc(C(F)(F)F)c(N[C@@H]4CCC[C@@H]4C(=O)N[C@H]4CC[C@H](N5CCOCC5)CC4)n3)cc2)CC1] | B | | 687 | 275 |
| 57 | 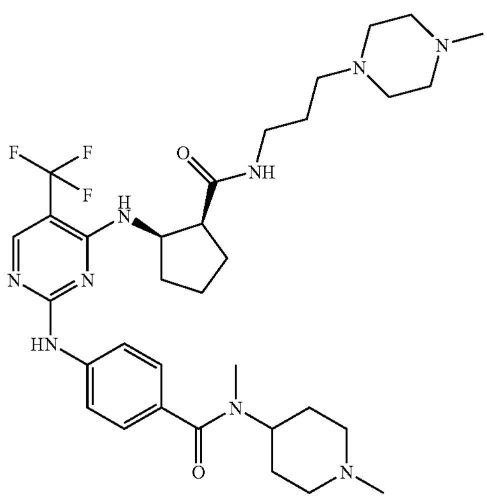 [SMILES: CN1CCC(N(C)C(=O)c2ccc(Nc3ncc(C(F)(F)F)c(N[C@@H]4CCC[C@@H]4C(=O)NCCCN4CCN(C)CC4)n3)cc2)CC1] | B | | 660 | 275 |
| 58 | (rac) | B | 1.34 | 549 | 278 |

-continued
| Ex. No. | structure | method of synthesis | HPLC RT [min] | MS (ESI⁺) [M + H]⁺ | UV$_{max}$ [nm] |
| --- | --- | --- | --- | --- | --- |
| 59 | 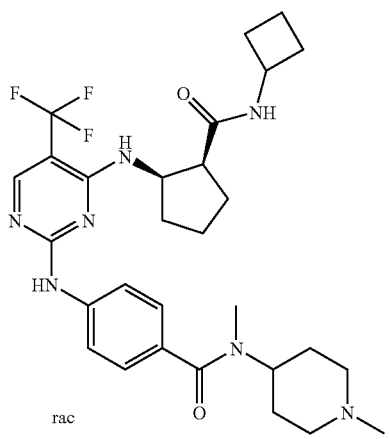 [SMILES: CN1CCC(N(C)C(=O)c2ccc(Nc3ncc(C(F)(F)F)c(N[C@@H]4CCC[C@@H]4C(=O)NC4CCC4)n3)cc2)CC1] rac | B | 1.47 | 574 | 278 |
| 60 | 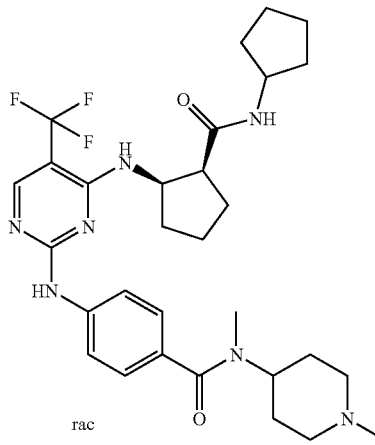 rac | B | 1.53 | 588 | 278 |
| 61 | 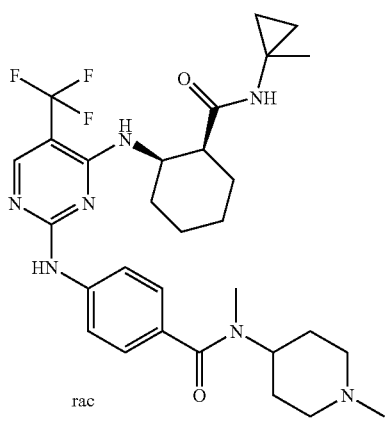 rac | B | 1.51 | 588 | 250 |

| Ex. No. | structure | method of synthesis | HPLC RT [min] | MS (ESI+) [M + H]+ | UVmax [nm] |
|---|---|---|---|---|---|
| 62 | 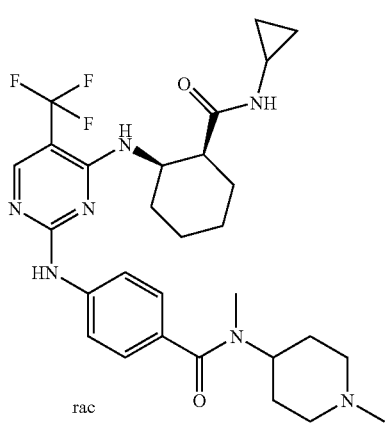 [SMILES: CN1CCC(N(C)C(=O)c2ccc(Nc3ncc(C(F)(F)F)c(N[C@@H]4CCCC[C@@H]4C(=O)NC4CC4)n3)cc2)CC1] rac | B | 1.45 | 574 | 278 |
| 63 | 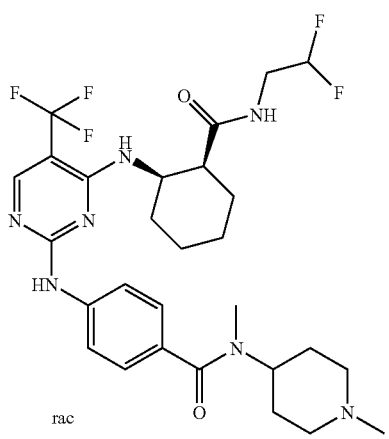 rac | B | 1.51 | 598 | 278 |
| 64 | 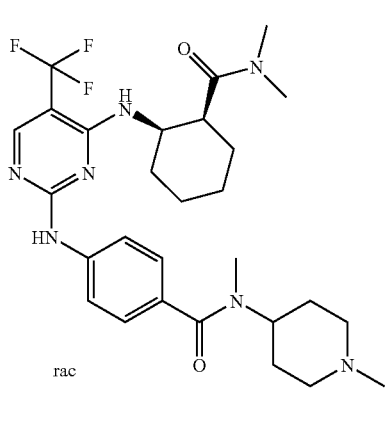 [SMILES: CN1CCC(N(C)C(=O)c2ccc(Nc3ncc(C(F)(F)F)c(N[C@@H]4CCCC[C@@H]4C(=O)N(C)C)n3)cc2)CC1] rac | B | 1.43 | 562 | 278 |

| Ex. No. | structure | method of synthesis | HPLC RT [min] | MS (ESI+) [M + H]+ | UV max [nm] |
|---|---|---|---|---|---|
| 65 | 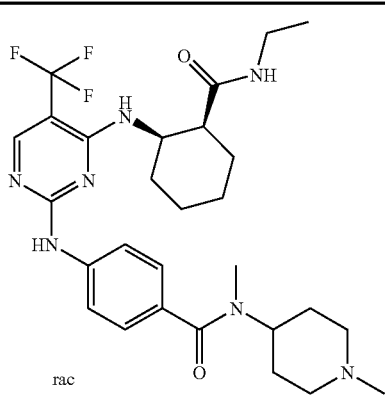 rac | B | 1.45 | 562 | 274 |
| 66 | 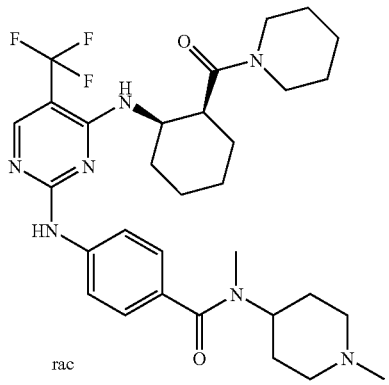 [SMILES: CN1CCC(N(C)C(=O)c2ccc(Nc3ncc(C(F)(F)F)c(N[C@@H]4CCCC[C@@H]4C(=O)N4CCCCC4)n3)cc2)CC1] rac | B | 1.59 | 602 | 278 |
| 67 | 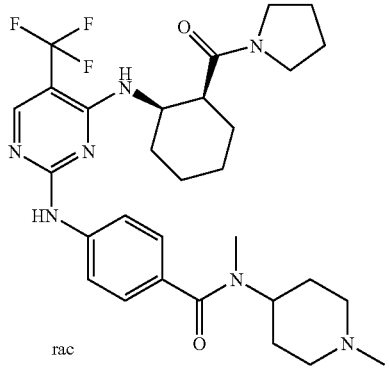 [SMILES: CN1CCC(N(C)C(=O)c2ccc(Nc3ncc(C(F)(F)F)c(N[C@@H]4CCCC[C@@H]4C(=O)N4CCCC4)n3)cc2)CC1] rac | B | 1.49 | 588 | 278 |
| 68 | 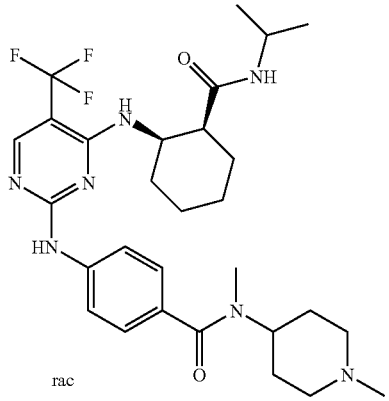 [SMILES: CC(C)NC(=O)[C@H]1CCCC[C@H]1Nc1nc(Nc2ccc(C(=O)N(C)C3CCN(C)CC3)cc2)ncc1C(F)(F)F] rac | B | 1.52 | 576 | 278 |

-continued
| Ex. No. | structure | method of synthesis | HPLC RT [min] | MS (ESI⁺) [M + H]⁺ | UV$_{max}$ [nm] |
|---|---|---|---|---|---|
| 69 | 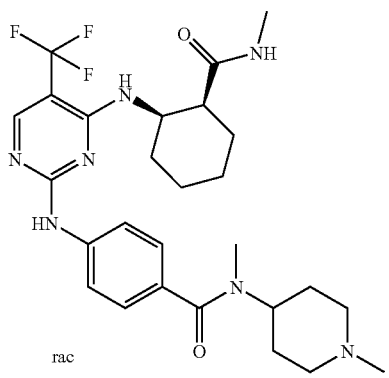 [SMILES: CNC(=O)[C@H]1CCCC[C@H]1Nc1nc(Nc2ccc(C(=O)N(C)C3CCN(C)CC3)cc2)ncc1C(F)(F)F] rac | B | 1.39 | 548 | 274 |
| 70 | 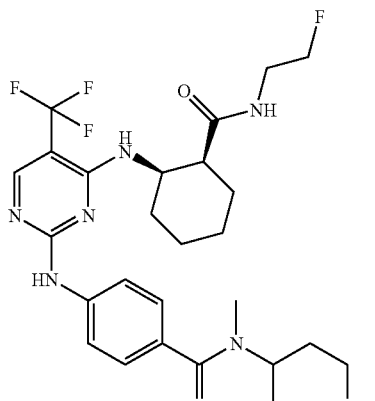 rac | B | 1.40 | 580 | 278 |
| 71 | 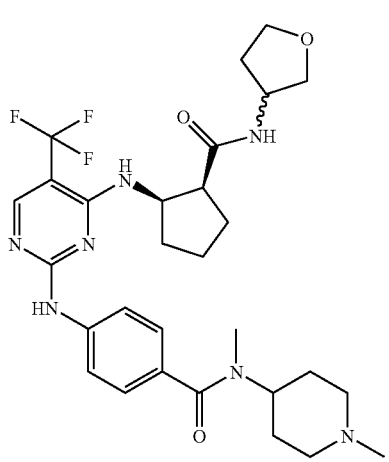 [SMILES: CN1CCC(N(C)C(=O)c2ccc(Nc3ncc(C(F)(F)F)c(N[C@@H]4CCC[C@@H]4C(=O)NC4CCOC4)n3)cc2)CC1] | B | 1.33 | 590 | 274 |

-continued

| Ex. No. | structure | method of synthesis | HPLC RT [min] | MS (ESI⁺) [M + H]⁺ | UV$_{max}$ [nm] |
|---|---|---|---|---|---|
| 72 | 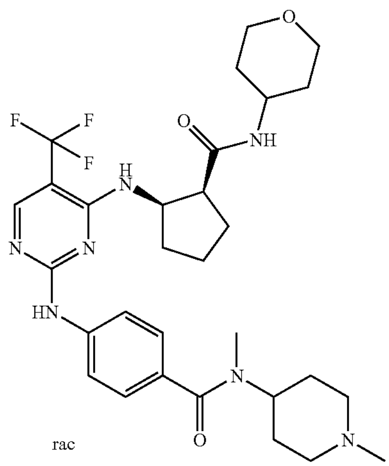 [SMILES: CN1CCC(N(C)C(=O)c2ccc(Nc3ncc(C(F)(F)F)c(N[C@@H]4CCC[C@@H]4C(=O)NC4CCOCC4)n3)cc2)CC1] | B | | 604 | 278 |
| 73 | 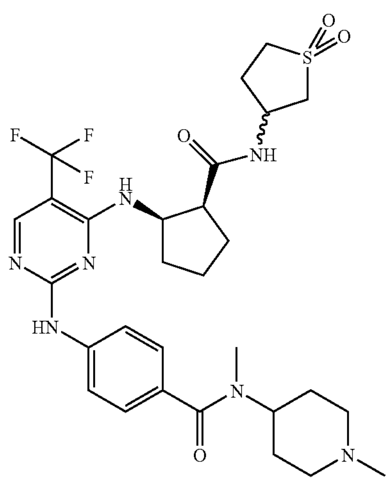 [SMILES: CN1CCC(N(C)C(=O)c2ccc(Nc3ncc(C(F)(F)F)c(N[C@@H]4CCC[C@@H]4C(=O)NC4CCS(=O)(=O)C4)n3)cc2)CC1] | B | | 638 | 278 |
| 74 | 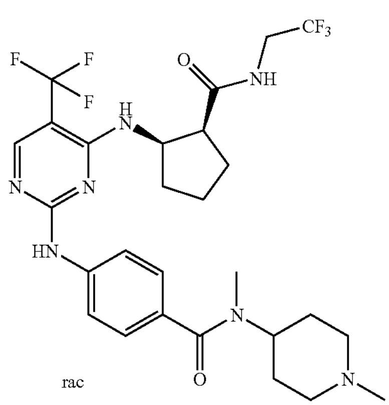 [SMILES: CN1CCC(N(C)C(=O)c2ccc(Nc3ncc(C(F)(F)F)c(N[C@@H]4CCC[C@@H]4C(=O)NCC(F)(F)F)n3)cc2)CC1] | B | 1.49 | 602 | 278 |

-continued
| Ex. No. | structure | method of synthesis | HPLC RT [min] | MS (ESI+) [M + H]+ | UV_max [nm] |
|---|---|---|---|---|---|
| 75 | 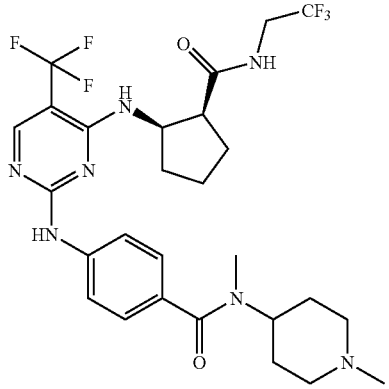 [SMILES: CN1CCC(N(C)C(=O)c2ccc(Nc3ncc(C(F)(F)F)c(N[C@@H]4CCC[C@@H]4C(=O)NCC(F)(F)F)n3)cc2)CC1] | B | 1.49 | 602 | 278 |
| 76 | 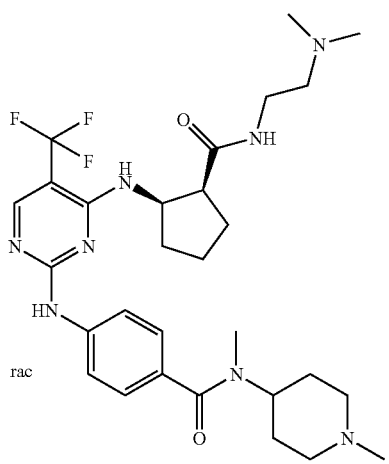 [SMILES: CN(C)CCNC(=O)[C@H]1CCC[C@H]1Nc1nc(Nc2ccc(C(=O)N(C)C3CCN(C)CC3)cc2)ncc1C(F)(F)F] | B |  | 591 | 274 |
| 77 | 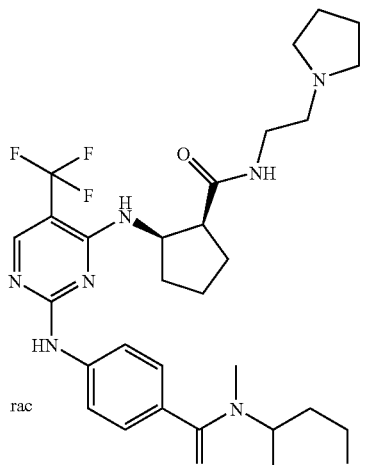 | B |  | 617 | 278 |

| Ex. No. | structure | method of synthesis | HPLC RT [min] | MS (ESI⁺) [M + H]⁺ | UV$_{max}$ [nm] |
|---|---|---|---|---|---|
| 78 | 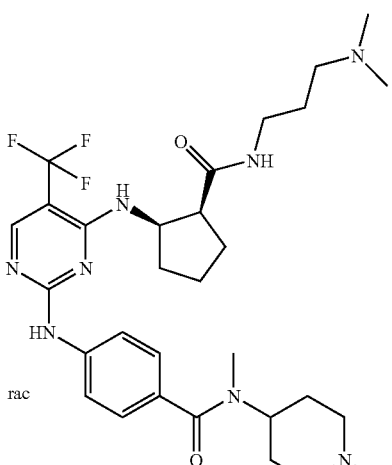 rac | B | | 605 | 278 |
| 79 | 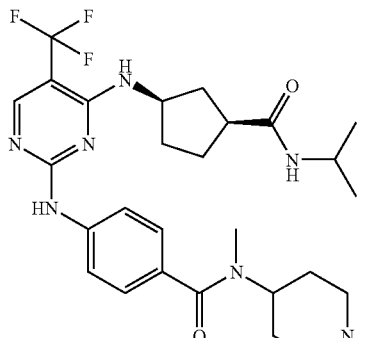 | B | 1.40 | 562 | 274 |
| 80 | 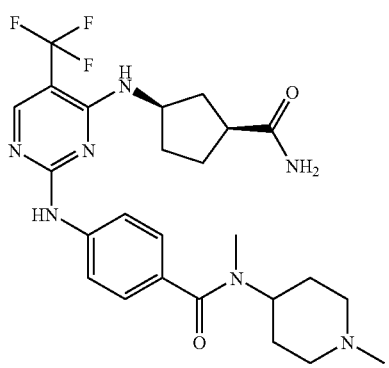 [SMILES: CN1CCC(N(C)C(=O)c2ccc(Nc3ncc(C(F)(F)F)c(N[C@@H]4CC[C@H](C(N)=O)C4)n3)cc2)CC1] | B | | 520 | 270 |
| 81 | 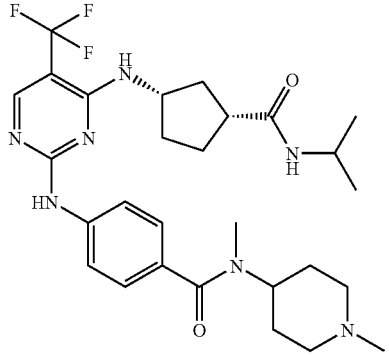 [SMILES: CC(C)NC(=O)[C@@H]1CC[C@H](Nc2nc(Nc3ccc(C(=O)N(C)C4CCN(C)CC4)cc3)ncc2C(F)(F)F)C1] | B | 1.37 | 562 | 274 |

| Ex. No. | structure | method of synthesis | HPLC RT [min] | MS (ESI+) [M + H]+ | UVmax [nm] |
|---|---|---|---|---|---|
| 82 | 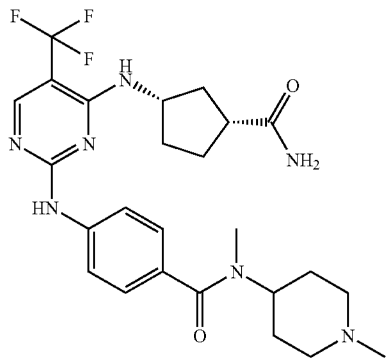 [SMILES: CN1CCC(N(C)C(=O)c2ccc(Nc3ncc(C(F)(F)F)c(N[C@H]4CC[C@@H](C(N)=O)C4)n3)cc2)CC1] | B | | 520 | 270 |
| 83 | 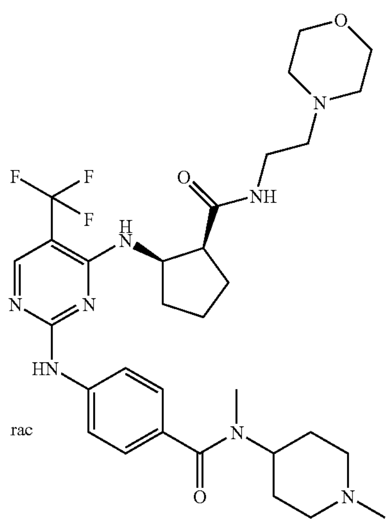 [SMILES: CN1CCC(N(C)C(=O)c2ccc(Nc3ncc(C(F)(F)F)c(N[C@@H]4CCC[C@@H]4C(=O)NCCN4CCOCC4)n3)cc2)CC1] | B | | 633 | 298 |
| 84 | 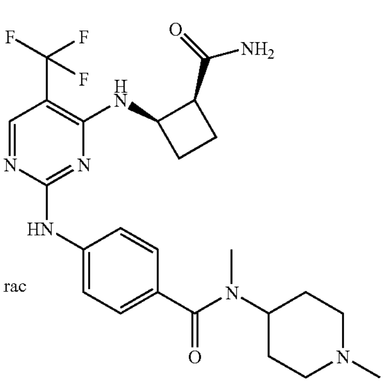 [SMILES: CN1CCC(N(C)C(=O)c2ccc(Nc3ncc(C(F)(F)F)c(N[C@@H]4CC[C@@H]4C(N)=O)n3)cc2)CC1] | A | | 506 | 274 |
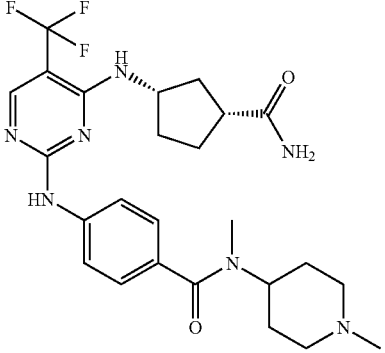

| Ex. No. | structure | method of synthesis | HPLC RT [min] | MS (ESI⁺) [M + H]⁺ | UV$_{max}$ [nm] |
|---|---|---|---|---|---|
| 85 | rac | B | 1.20 | 532 | 298 |
| 86 | rac | B |  | 535 | 278 |
| 87 | 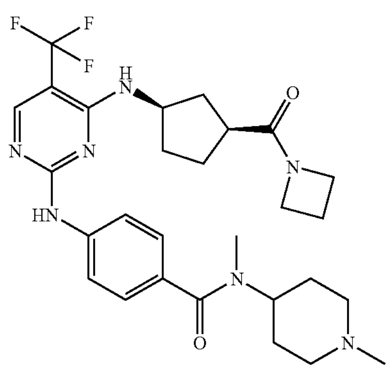 [SMILES: CN1CCC(N(C)C(=O)c2ccc(Nc3ncc(C(F)(F)F)c(N[C@@H]4CC[C@H](C(=O)N5CCC5)C4)n3)cc2)CC1] | B |  | 560 |  |
| 88 | 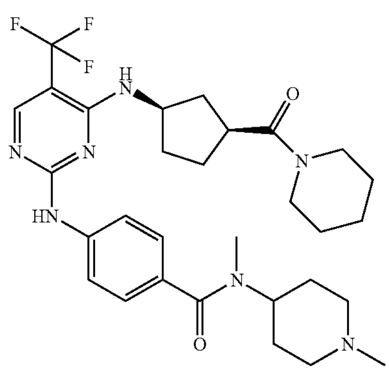 [SMILES: CN1CCC(N(C)C(=O)c2ccc(Nc3ncc(C(F)(F)F)c(N[C@@H]4CC[C@H](C(=O)N5CCCCC5)C4)n3)cc2)CC1] | B | 1.49 | 588 | 274 |

-continued

| Ex. No. | structure | method of synthesis | HPLC RT [min] | MS (ESI⁺) [M + H]⁺ | UV$_{max}$ [nm] |
|---|---|---|---|---|---|
| 89 | 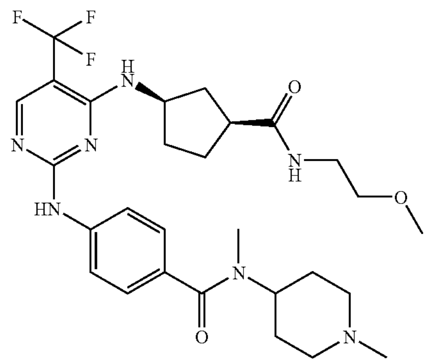 [SMILES: COCCNC(=O)[C@H]1CC[C@@H](Nc2nc(Nc3ccc(C(=O)N(C)C4CCN(C)CC4)cc3)ncc2C(F)(F)F)C1] | B | 1.29 | 578 | 274 |
| 90 | 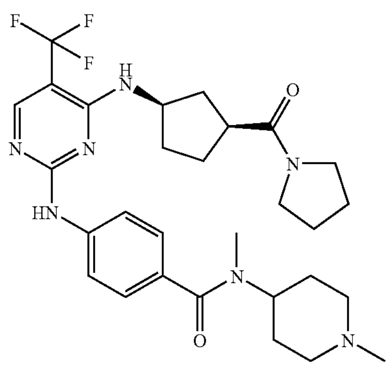 [SMILES: CN1CCC(N(C)C(=O)c2ccc(Nc3ncc(C(F)(F)F)c(N[C@@H]4CC[C@H](C(=O)N5CCCC5)C4)n3)cc2)CC1] | B | 1.33 | 574 | 278 |
| 91 | 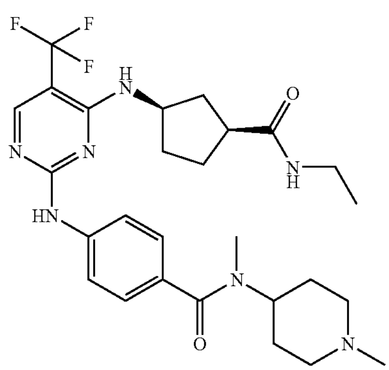 | B | | 548 | 274 |
| 92 (B-4c) | 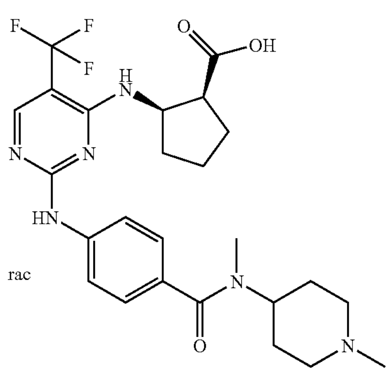 [SMILES: CN1CCC(N(C)C(=O)c2ccc(Nc3ncc(C(F)(F)F)c(N[C@@H]4CCC[C@@H]4C(=O)O)n3)cc2)CC1] | B | 1.30 | 521 | 278 |

| Ex. No. | structure | method of synthesis | HPLC RT [min] | MS (ESI+) [M + H]+ | UVmax [nm] |
|---|---|---|---|---|---|
| 93 | 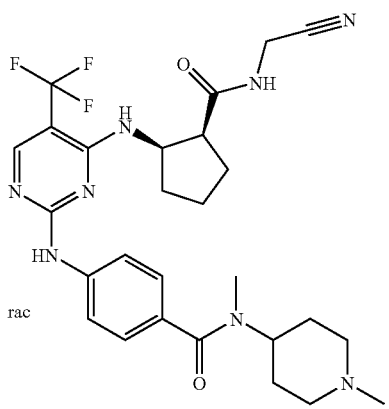 [SMILES: CN1CCC(N(C)C(=O)c2ccc(Nc3ncc(C(F)(F)F)c(N[C@@H]4CCC[C@@H]4C(=O)NCC#N)n3)cc2)CC1] | B | 1.31 | 559 | 278 |
| 94 | 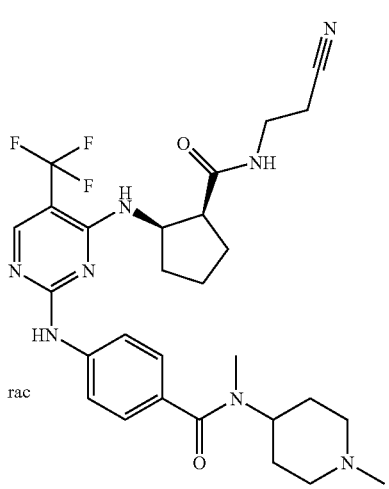 [SMILES: CN1CCC(N(C)C(=O)c2ccc(Nc3ncc(C(F)(F)F)c(N[C@@H]4CCC[C@@H]4C(=O)NCCC#N)n3)cc2)CC1] | B | 1.33 | 573 | 278 |
| 95 | 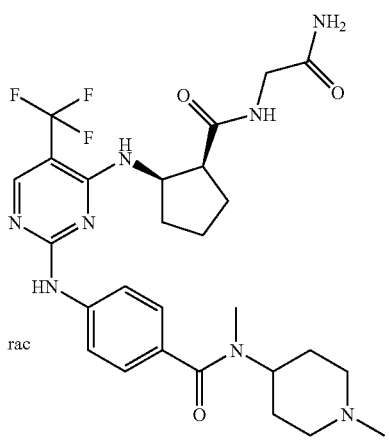 [SMILES: CN1CCC(N(C)C(=O)c2ccc(Nc3ncc(C(F)(F)F)c(N[C@@H]4CCC[C@@H]4C(=O)NCC(N)=O)n3)cc2)CC1] | B | | 577 | 298 |

| Ex. No. | structure | method of synthesis | HPLC RT [min] | MS (ESI+) [M + H]+ | UVmax [nm] |
|---|---|---|---|---|---|
| 96 | 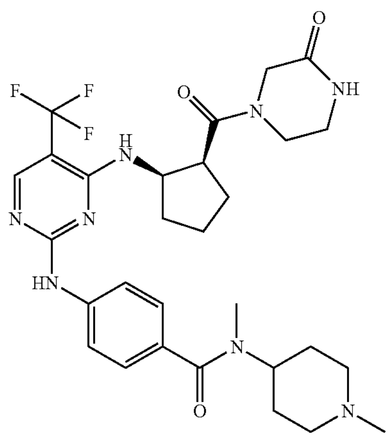 [SMILES: CN1CCC(N(C)C(=O)c2ccc(Nc3ncc(C(F)(F)F)c(N[C@@H]4CCC[C@@H]4C(=O)N4CCNC(=O)C4)n3)cc2)CC1] | B | | 603 | 298 |
| 97 | 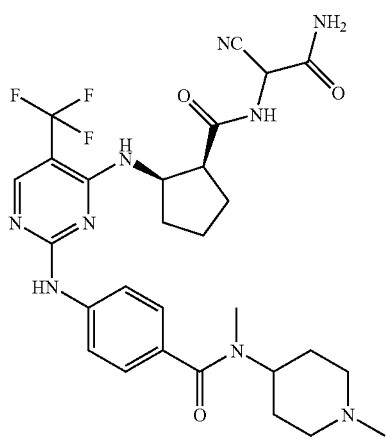 | B | 1.28 | 602 | 298 |
| 98 | 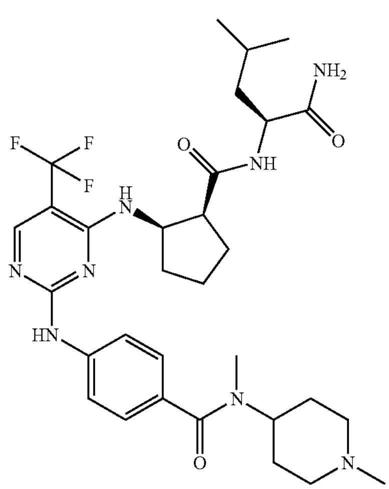 [SMILES: CC(C)C[C@H](NC(=O)[C@H]1CCC[C@H]1Nc1nc(Nc2ccc(C(=O)N(C)C3CCN(C)CC3)cc2)ncc1C(F)(F)F)C(N)=O] | B | 1.46 | 633 | 298 |

| Ex. No. | structure | method of synthesis | HPLC RT [min] | MS (ESI+) [M + H]+ | UVmax [nm] |
|---|---|---|---|---|---|
| 99 | 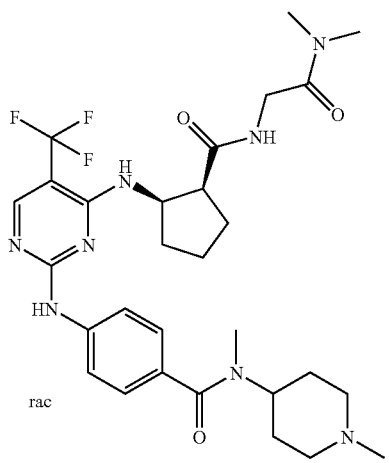 [SMILES: CN1CCC(N(C)C(=O)c2ccc(Nc3ncc(C(F)(F)F)c(N[C@@H]4CCC[C@@H]4C(=O)NCC(=O)N(C)C)n3)cc2)CC1] rac | B | 1.32 | 605 | 298 |
| 100 | 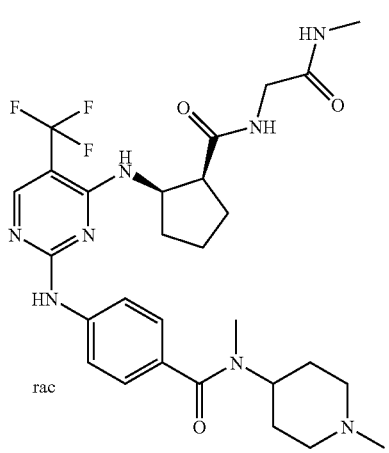 [SMILES: CNC(=O)CNC(=O)[C@H]1CCC[C@H]1Nc1nc(Nc2ccc(C(=O)N(C)C3CCN(C)CC3)cc2)ncc1C(F)(F)F] rac | B | 1.22 | 591 | 298 |
| 101 | 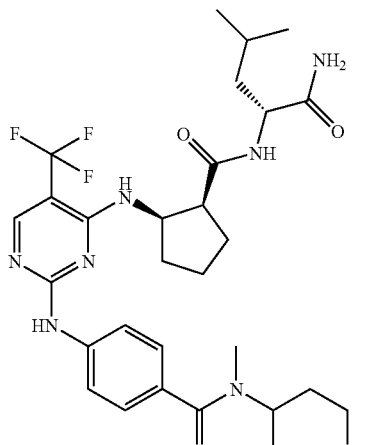 | B | 1.46 | 633 | 298 |

-continued
| Ex. No. | structure | method of synthesis | HPLC RT [min] | MS (ESI⁺) [M + H]⁺ | UV$_{max}$ [nm] |
|---|---|---|---|---|---|
| 102 | 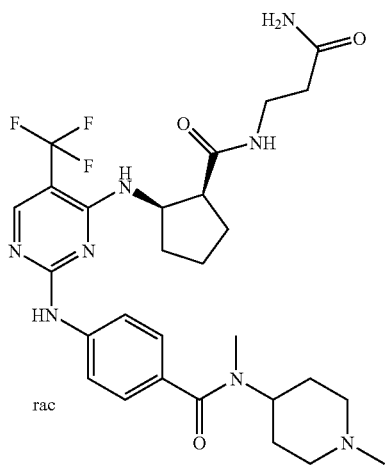 [SMILES: CN1CCC(N(C)C(=O)c2ccc(Nc3ncc(C(F)(F)F)c(N[C@@H]4CCC[C@@H]4C(=O)NCCC(N)=O)n3)cc2)CC1] rac | B | 1.21 | 591 | 298 |
| 103 | 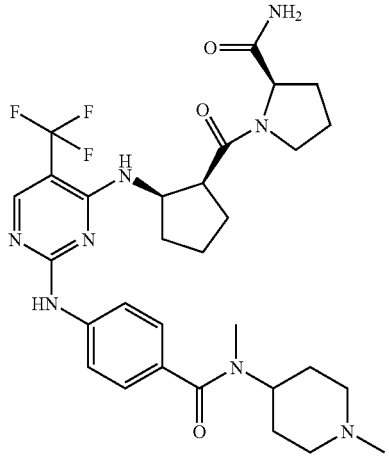 [SMILES: CN1CCC(N(C)C(=O)c2ccc(Nc3ncc(C(F)(F)F)c(N[C@@H]4CCC[C@@H]4C(=O)N4CCC[C@@H]4C(N)=O)n3)cc2)CC1] | B | | 617 | 298 |
| 104 | 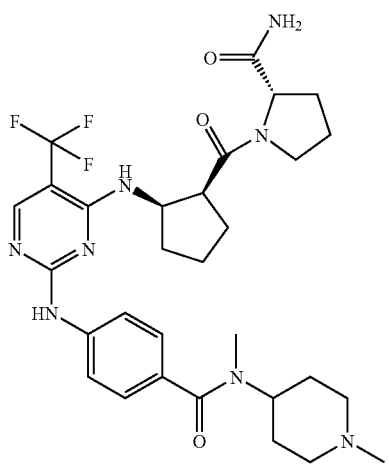 [SMILES: CN1CCC(N(C)C(=O)c2ccc(Nc3ncc(C(F)(F)F)c(N[C@@H]4CCC[C@@H]4C(=O)N4CCC[C@H]4C(N)=O)n3)cc2)CC1] | B | | 617 | 298 |

-continued

| Ex. No. | structure | method of synthesis | HPLC RT [min] | MS (ESI⁺) [M + H]⁺ | UV$_{max}$ [nm] |
|---|---|---|---|---|---|
| 105 | 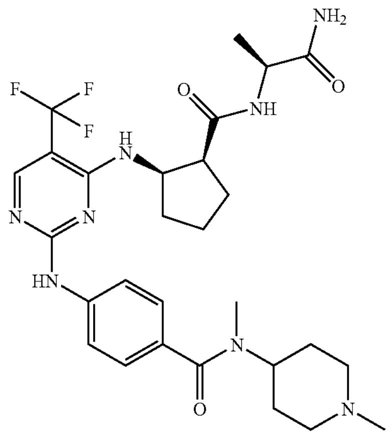 [SMILES: C[C@H](NC(=O)[C@H]1CCC[C@H]1Nc1nc(Nc2ccc(C(=O)N(C)C3CCN(C)CC3)cc2)ncc1C(F)(F)F)C(N)=O] | B | | 591 | 298 |
| 106 | 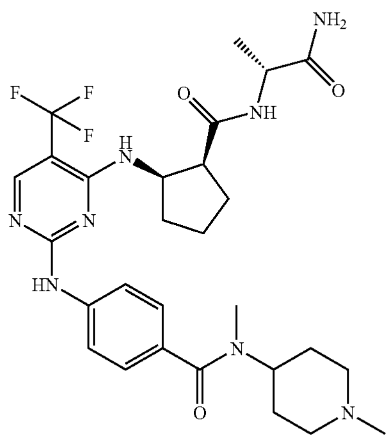 [SMILES: C[C@@H](NC(=O)[C@H]1CCC[C@H]1Nc1nc(Nc2ccc(C(=O)N(C)C3CCN(C)CC3)cc2)ncc1C(F)(F)F)C(N)=O] | B | | 591 | 298 |
| 107 | 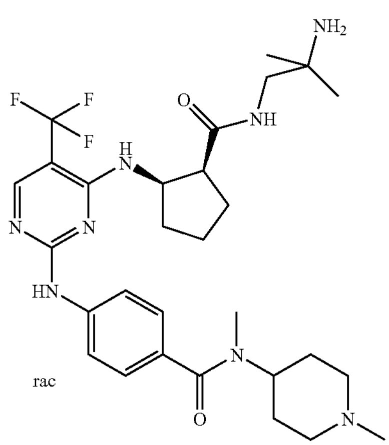 [SMILES: CN1CCC(N(C)C(=O)c2ccc(Nc3ncc(C(F)(F)F)c(N[C@@H]4CCC[C@@H]4C(=O)NCC(C)(C)N)n3)cc2)CC1] | B | | 591 | 302 |

| Ex. No. | structure | method of synthesis | HPLC RT [min] | MS (ESI⁺) [M + H]⁺ | UV$_{max}$ [nm] |
|---|---|---|---|---|---|
| 108 | 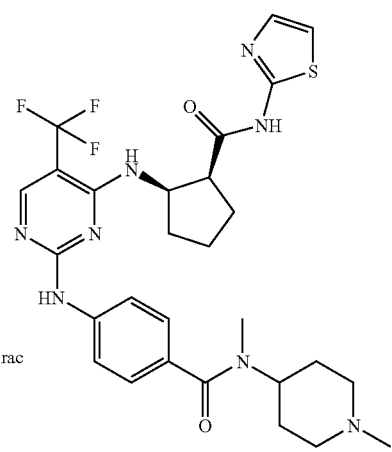 [SMILES: CN1CCC(N(C)C(=O)c2ccc(Nc3ncc(C(F)(F)F)c(N[C@@H]4CCC[C@@H]4C(=O)Nc4nccs4)n3)cc2)CC1] rac | B | 1.53 | 603 | 278 |
| 109 (D-1a) | 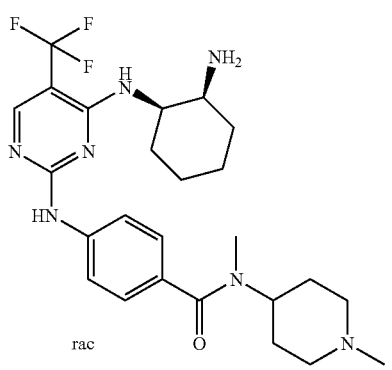 [SMILES: CN1CCC(N(C)C(=O)c2ccc(Nc3ncc(C(F)(F)F)c(N[C@@H]4CCCC[C@@H]4N)n3)cc2)CC1] rac | D | | 506 | 280 |
| 110 | 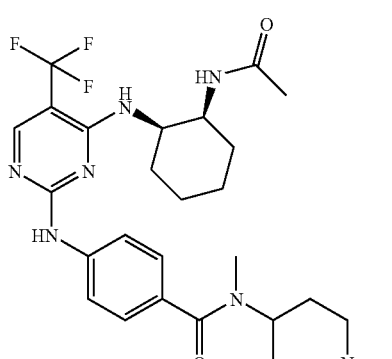 rac | D | | | 272 |
| 111 | 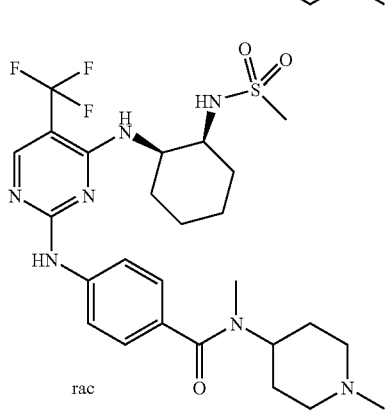 rac | D | 1.35 | 584 | 274 |

-continued
| Ex. No. | structure | method of synthesis | HPLC RT [min] | MS (ESI+) [M + H]+ | UV$_{max}$ [nm] |
|---|---|---|---|---|---|
| 112 | 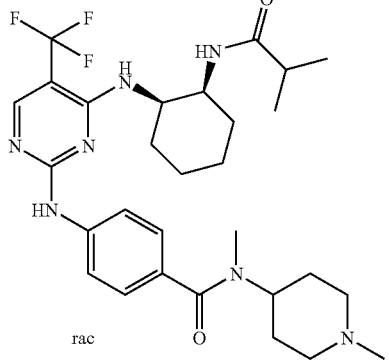 | D | 1.45 | 576 | 276 |
| 113 | 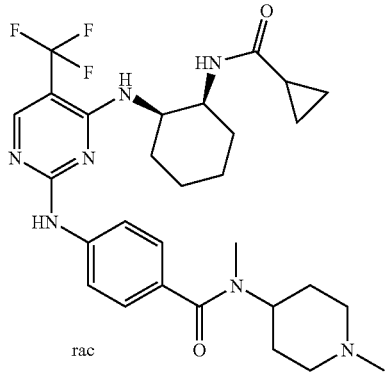 [SMILES: CN1CCC(N(C)C(=O)c2ccc(Nc3ncc(C(F)(F)F)c(N[C@@H]4CCCC[C@@H]4NC(=O)C4CC4)n3)cc2)CC1] | D | 1.43 | 574 | 275 |
| 114 | 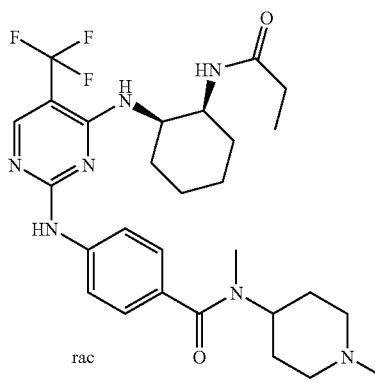 | D | 1.35 | 562 | 274 |
| 115 | 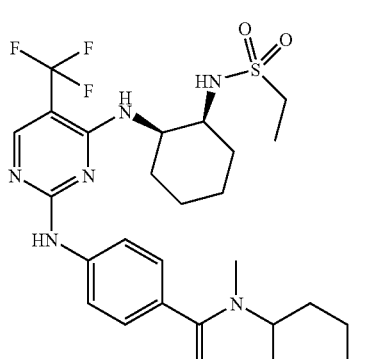 | D | 1.38 | 598 | 276 |

-continued
| Ex. No. | structure | method of synthesis | HPLC RT [min] | MS (ESI+) [M + H]+ | UVmax [nm] |
|---|---|---|---|---|---|
| 116 | 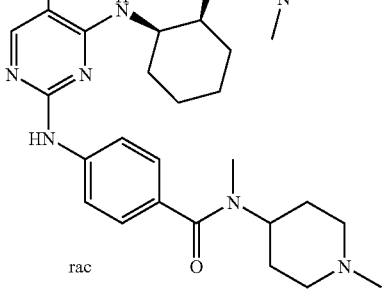 rac | D | 1.43 | 577 | 276 |
| 117 | 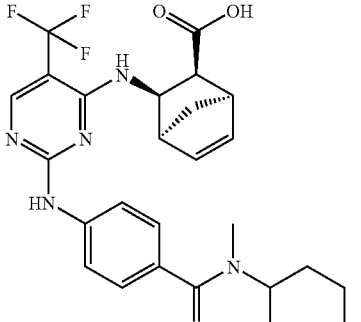 rac | B | 1.38 | 545 | 274 |
| 118 | 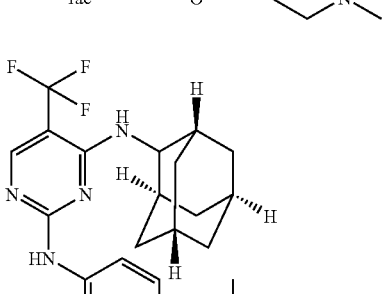 | B | 1.82 | 543 | 281 |
| 119 | 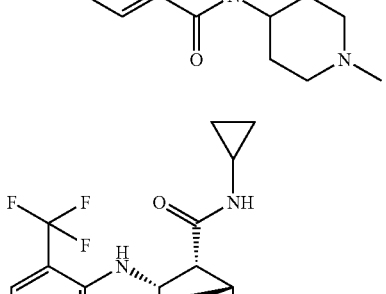 rac | B | 1.51 | 586 | 273 |

-continued
| Ex. No. | structure | method of synthesis | HPLC RT [min] | MS (ESI+) [M + H]+ | UV$_{max}$ [nm] |
|---|---|---|---|---|---|
| 120 | 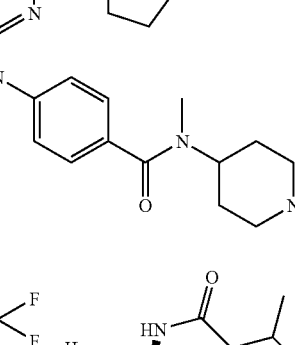 | D | 1.42 | 562 | 275 |
| 121 | 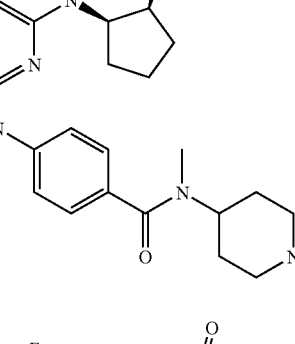 | D | 1.47 | 576 | 278 |
| 122 | 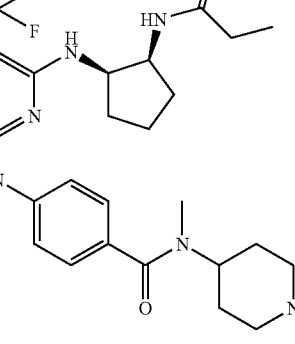 | D | 1.27 | 548 | 272 |
| 123 | 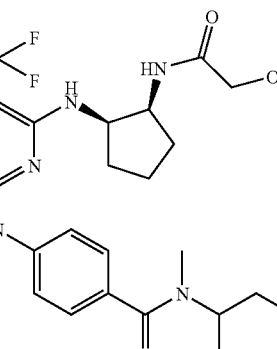 | D | 1.29 | 564 | 275 |

-continued

| Ex. No. | structure | method of synthesis | HPLC RT [min] | MS (ESI⁺) [M + H]⁺ | UV$_{max}$ [nm] |
|---|---|---|---|---|---|
| 124 (D-1a) | 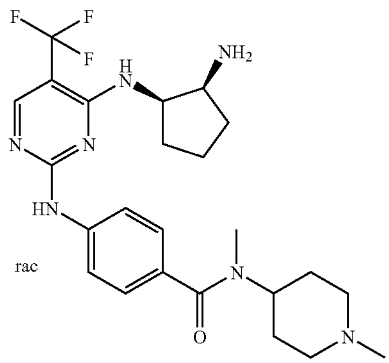 [SMILES: CN1CCC(N(C)C(=O)c2ccc(Nc3ncc(C(F)(F)F)c(N[C@@H]4CCC[C@@H]4N)n3)cc2)CC1] | D | | 492 | 277 |
| 125 | 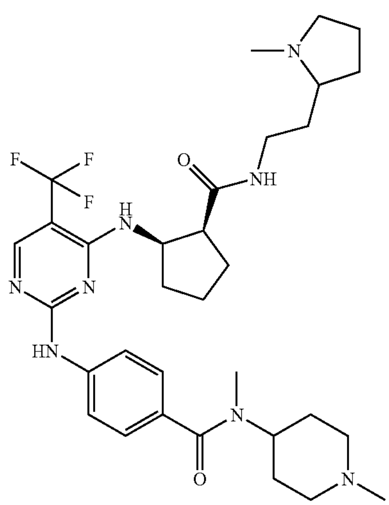 [SMILES: CN1CCC(N(C)C(=O)c2ccc(Nc3ncc(C(F)(F)F)c(N[C@@H]4CCC[C@@H]4C(=O)NCCC4CCCN4C)n3)cc2)CC1] | B | | 631 | 277 |
| 126 | 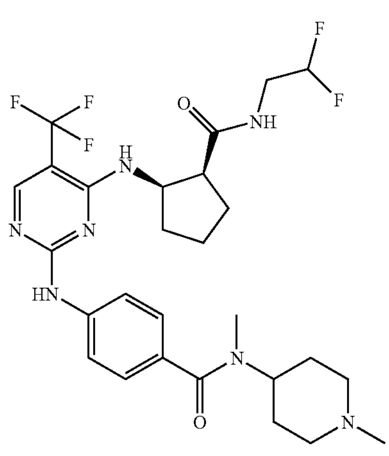 | B | 1.42 | 584 | 277 |

| Ex. No. | structure | method of synthesis | HPLC RT [min] | MS (ESI+) [M + H]+ | UV_max [nm] |
|---|---|---|---|---|---|
| 127 | 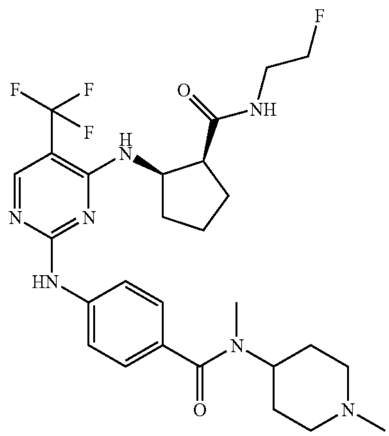 [SMILES: CN1CCC(N(C)C(=O)c2ccc(Nc3ncc(C(F)(F)F)c(N[C@@H]4CCC[C@@H]4C(=O)NCCF)n3)cc2)CC1] | B | 1.30 | 566 | 270 |
| 128 | 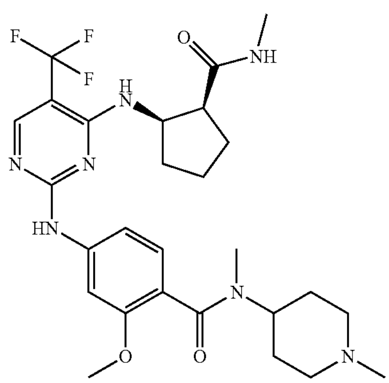 [SMILES: CNC(=O)[C@H]1CCC[C@H]1Nc1nc(Nc2ccc(C(=O)N(C)C3CCN(C)CC3)c(OC)c2)ncc1C(F)(F)F] | A | 1.52 | 564 | 270 |
| 129 | 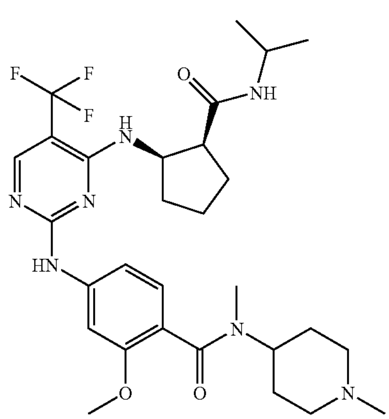 [SMILES: COc1cc(Nc2ncc(C(F)(F)F)c(N[C@@H]3CCC[C@@H]3C(=O)NC(C)C)n2)ccc1C(=O)N(C)C1CCN(C)CC1] | A | 1.70 | 592 | 274/300 |

| Ex. No. | structure | method of synthesis | HPLC RT [min] | MS (ESI⁺) [M + H]⁺ | UV$_{max}$ [nm] |
|---|---|---|---|---|---|
| 130 | 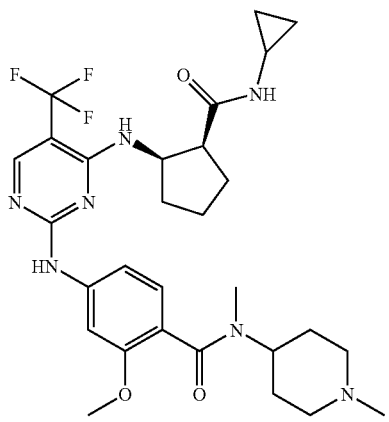 [SMILES: COc1cc(Nc2ncc(C(F)(F)F)c(N[C@@H]3CCC[C@@H]3C(=O)NC3CC3)n2)ccc1C(=O)N(C)C1CCN(C)CC1] | A | 1.59 | 590 | 272/300 |
| 131 | 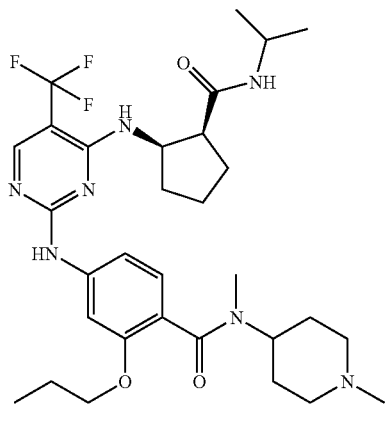 | C | 1.56 | 620 | 238 |
| 132 | 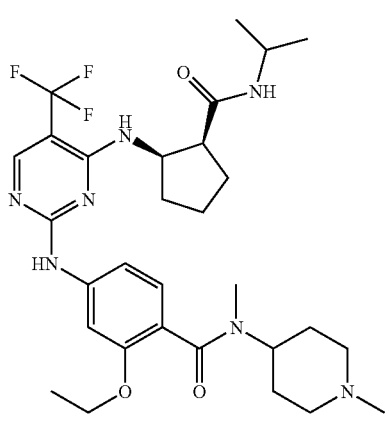 [SMILES: CCOc1cc(Nc2ncc(C(F)(F)F)c(N[C@@H]3CCC[C@@H]3C(=O)NC(C)C)n2)ccc1C(=O)N(C)C1CCN(C)CC1] | C | 1.42 | 606 | 226 |

-continued

| Ex. No. | structure | method of synthesis | HPLC RT [min] | MS (ESI+) [M + H]+ | UVmax [nm] |
|---|---|---|---|---|---|
| 133 | 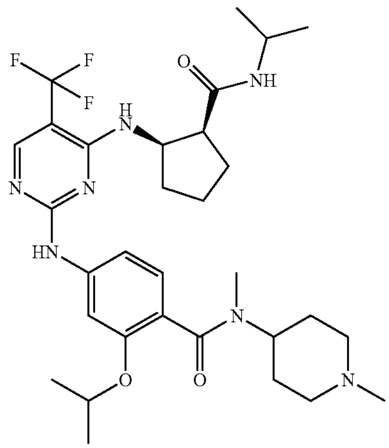 [SMILES: CC(C)NC(=O)[C@H]1CCC[C@H]1Nc1nc(Nc2ccc(C(=O)N(C)C3CCN(C)CC3)c(OC(C)C)c2)ncc1C(F)(F)F] | C | 1.53 | 620 | 226 |
| 134 | 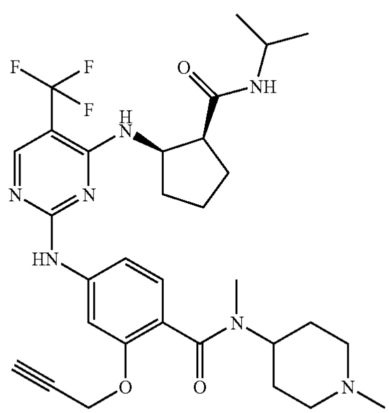 [SMILES: C#CCOc1cc(Nc2ncc(C(F)(F)F)c(N[C@@H]3CCC[C@@H]3C(=O)NC(C)C)n2)ccc1C(=O)N(C)C1CCN(C)CC1] | C | 1.48 | 616 | 230 |
| 135 | 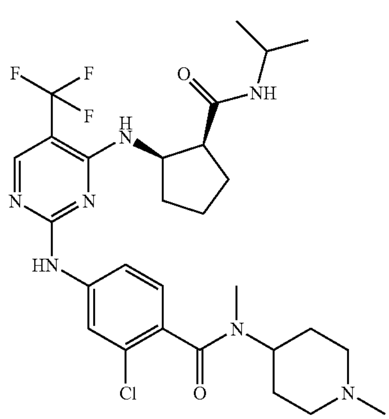 | C | 1.54 | 596 | 222/274 |

| Ex. No. | structure | method of synthesis | HPLC RT [min] | MS (ESI⁺) [M + H]⁺ | UV$_{max}$ [nm] |
|---|---|---|---|---|---|
| 136 | 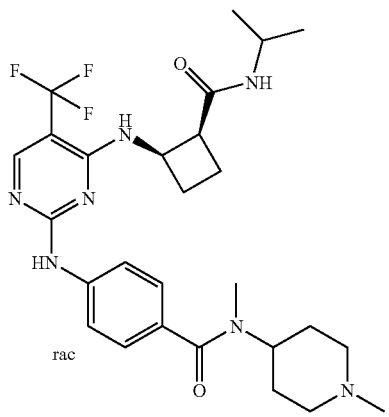 [SMILES: CC(C)NC(=O)[C@H]1CC[C@H]1Nc1nc(Nc2ccc(C(=O)N(C)C3CCN(C)CC3)cc2)ncc1C(F)(F)F] | D | 1.39 | 548 | 278 |
| 137 | 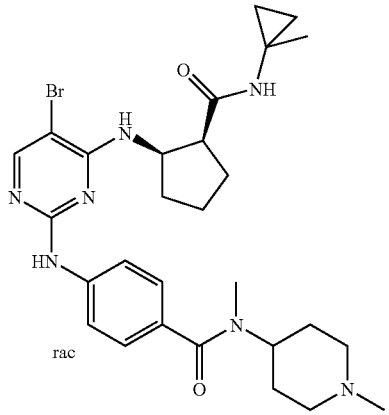 [SMILES: CN1CCC(N(C)C(=O)c2ccc(Nc3ncc(Br)c(N[C@@H]4CCC[C@@H]4C(=O)NC4(C)CC4)n3)cc2)CC1] | E | 1.22 | 584/586 | 278 |
| 138 | 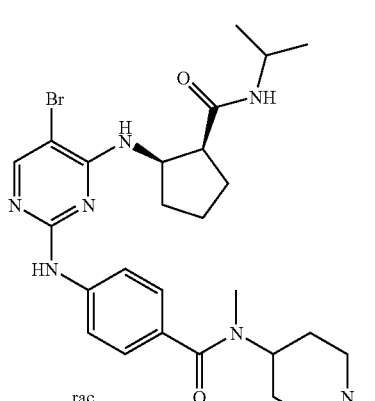 | E | 1.28 | 572/574 | 278 |

-continued
| Ex. No. | structure | method of synthesis | HPLC RT [min] | MS (ESI+) [M + H]+ | UVmax [nm] |
|---|---|---|---|---|---|
| 139 | 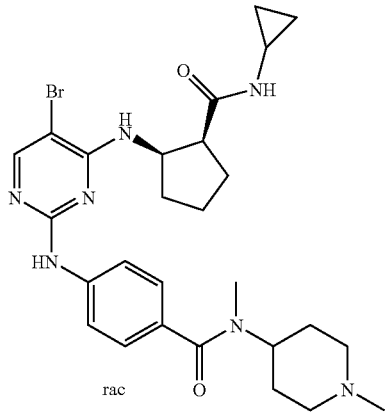 [SMILES: CN1CCC(N(C)C(=O)c2ccc(Nc3ncc(Br)c(N[C@@H]4CCC[C@@H]4C(=O)NC4CC4)n3)cc2)CC1] | E | | 570/572 | 274 |
| 140 | 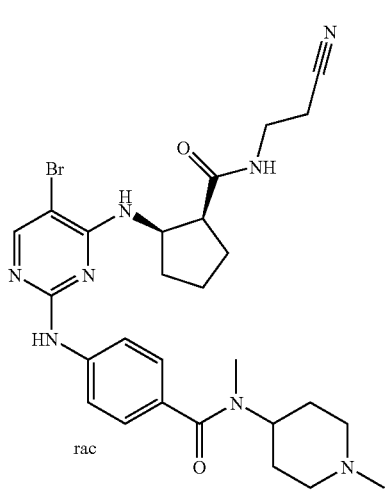 [SMILES: CN1CCC(N(C)C(=O)c2ccc(Nc3ncc(Br)c(N[C@@H]4CCC[C@@H]4C(=O)NCCC#N)n3)cc2)CC1] | E | | 583/585 | 275 |
| 141 | 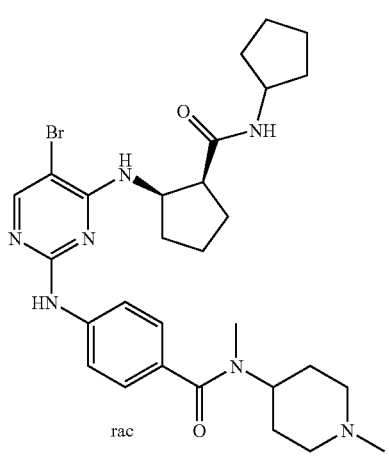 [SMILES: CN1CCC(N(C)C(=O)c2ccc(Nc3ncc(Br)c(N[C@@H]4CCC[C@@H]4C(=O)NC4CCCC4)n3)cc2)CC1] | E | 1.35 | 598/600 | 278 |

-continued

| Ex. No. | structure | method of synthesis | HPLC RT [min] | MS (ESI+) [M + H]+ | UVmax [nm] |
|---|---|---|---|---|---|
| 142 | 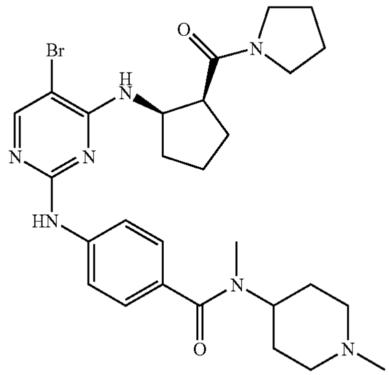 [SMILES: CN1CCC(N(C)C(=O)c2ccc(Nc3ncc(Br)c(N[C@@H]4CCC[C@@H]4C(=O)N4CCCC4)n3)cc2)CC1] | E | | 584/586 | 218/278 |
| 143 | 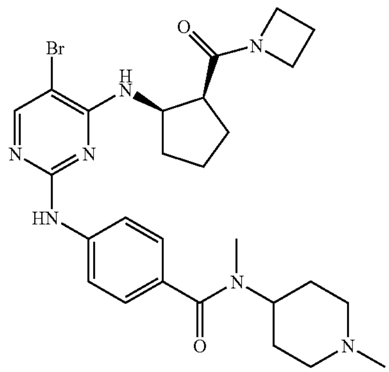 [SMILES: CN1CCC(N(C)C(=O)c2ccc(Nc3ncc(Br)c(N[C@@H]4CCC[C@@H]4C(=O)N4CCC4)n3)cc2)CC1] | E | | 570/572 | 214/276 |
| 144 | 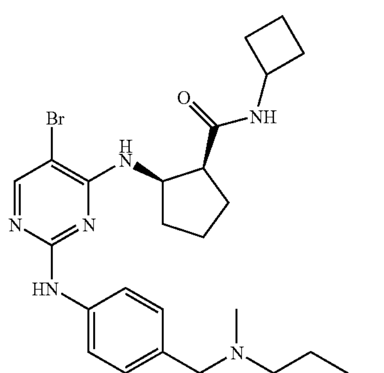 | E | 1.27 | 584/586 | 278 |
| 145 | 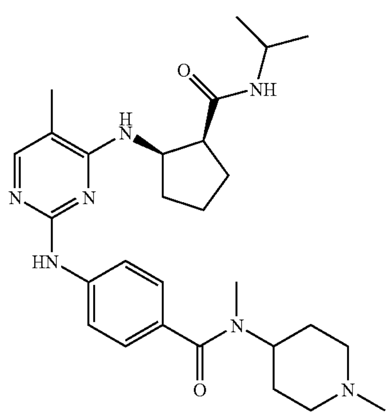 [SMILES: Cc1cnc(Nc2ccc(C(=O)N(C)C3CCN(C)CC3)cc2)nc1N[C@@H]1CCC[C@@H]1C(=O)NC(C)C] | C | 1.19 | 508 | 270 |

-continued

| Ex. No. | structure | method of synthesis | HPLC RT [min] | MS (ESI⁺) [M + H]⁺ | UV$_{max}$ [nm] |
|---|---|---|---|---|---|
| 146 | 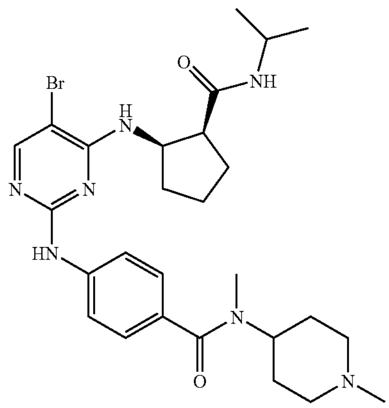 | E | | 572/574 | |
| 147 | 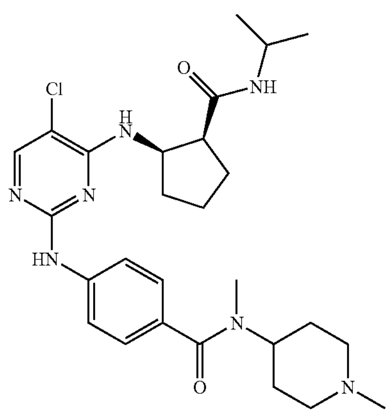 [SMILES: CC(C)NC(=O)[C@H]1CCC[C@H]1Nc1nc(Nc2ccc(C(=O)N(C)C3CCN(C)CC3)cc2)ncc1Br] | C | | 528/530 | |

The Examples describe the biological activity of the compounds according to the invention without restricting the invention to these Examples.

As demonstrated by DNA staining followed by FACS or Cellomics Array Scan analysis, the inhibition of proliferation brought about by the compounds according to the invention is mediated above all by errors in chromosome segregation. Because of the accumulation of faulty segregations, massive polyploidia occurs which may finally lead to inhibition of proliferation or even apoptosis. On the basis of their biological properties the compounds of general formula (I) according to the invention, their isomers and the physiologically acceptable salts thereof are suitable for treating diseases characterised by excessive or abnormal cell proliferation.

Example Aurora-B Kinase Assay

A radioactive enzyme inhibition assay was developed using $E.$ $coli$-expressed recombinant $Xenopus$ $laevis$ Aurora B wild-type protein equipped at the N-terminal position with a GST tag (amino acids 60-361) in a complex with $Xenopus$ $laevis$ INCENP (amino acids 790-847), which is obtained from bacteria and purified. In equivalent manner a $Xenopus$ $laevis$ Aurora B mutant (G96V) in a complex with $Xenopus$ $laevis$ INCENP$^{790-847}$ may also be used.

Expression and Purification

The coding sequence for Aurora-B$^{60-361}$ from $Xenopus$ $laevis$ is cloned into a modified version of pGEX-6T (Amersham Biotech) via BamHI and SalI cutting sites. The vector contains two cloning cassettes which are separated by a ribosomal binding site, allowing bi-cistronic expression. In this configuration $Xenopus$ $laevis$ Aurora B is expressed by the first cassette, and the $Xenopus$ $laevis$ INCENP$^{790-847}$ is expressed by the second cassette. The resulting vector is pAUB-IN$^{847}$.

First of all the $E.$ $coli$ strain BL21 (DE3) is co-transformed with pUBS520 helper plasmid and pAUB-IN$^{847}$, after which protein expression is induced using 0.3 mM IPTG at an OD$_{600}$ of 0.45-0.7. The expression is then continued for approx. 12-16 hours at 23-25° C. with agitation.

The bacteria are then removed by centrifuging and the pellet is lysed in lysis buffer (50 mM Tris/Cl pH 7.6, 300 mM NaCl, 1 mM DTT, 1 mM EDTA, 5% glycerol, Roche Complete Protease Inhibitor tablets) using ultrasound, using 20-30 mL lysis buffer per litre of $E.$ $coli$ culture. The lysed material is freed from debris by centrifugation (12000 rpm, 45-60 min, JA20 rotor). The supernatant is incubated with 300 μL of equilibrated GST Sepharose Fast Flow (Amersham Biosciences) per litre of $E.$ $coli$ culture for 4-5 h at 4° C. Then the column material is washed with 30 volumes of lysis buffer and then equilibrated with 30 volumes of cleavage buffer (50 mM Tris/Cl pH 7.6, 150 mM NaCl, 1 mM DTT, 1 mM EDTA). To cleave the GST tag from Aurora B, 10 units of Prescission Protease (Amersham Biosciences) are used per milligram of substrate and the mixture is incubated for 16 h at 4° C. The supernatant which contains the cleavage product is loaded onto a 6 mL Resource Q column (Amersham Biosciences) equilibrated with ion exchange buffer (50 mM Tris/

Cl pH 7.6, 150 mM NaCl, 1 mM DTT, 1 mM EDTA). The Aurora B/INCENP complex is caught as it flows through, then concentrated and loaded onto a Superdex 200 size exclusion chromatography (SEC) column equilibrated with SEC buffer (10 mM Tris/Cl pH 7.6, 150 mM NaCl, 1 mM DTT, 1 mM EDTA). Fractions which contain the AuroraB/INCENP complex are collected and concentrated using Vivaspin concentrators (molecular weight exclusion 3000-5000 Da) to a final concentration of 12 mg/mL. Aliquots (e.g. 240 ng/μL) for kinase assays are transferred from this stock solution into freezing buffer (50 mM Tris/Cl pH 8.0, 150 mM NaCl, 0.1 mM EDTA, 0.03% Brij-35, 10% glycerol, 1 mM DTT) and stored at −80° C.

Kinase Assay

Test substances are placed in a polypropylene dish (96 wells, Greiner #655 201), in order to cover a concentration frame of 10 μM-0.0001 μM. The final concentration of DMSO in the assay is 5%. 30 μL of protein mix (50 mM tris/Cl pH 7.5, 25 mM $MgCl_2$, 25 mM NaCl, 167 μM ATP, 10 ng *Xenopus laevis* Aurora B/INCENP complex in freezing buffer) are pipetted into the 10 μl of test substance provided in 25% DMSO and this is incubated for 15 min at RT. Then 10 μL of peptide mix (100 mM tris/Cl pH 7.5, 50 mM $MgCl_2$, 50 mM NaCl, 5 μM NaF, 5 μM DTT, 1 μCi gamma-P33-ATP [Amersham], 50 μM substrate peptide [biotin-EPLER-RLSLVPDS (SEQ ID NO:1) or multimers thereof, or biotin-EPLERRLSLVPKM (SEQ ID NO:2) or multimers thereof, or biotin-LRRSLGLRRSLGLRRSLGLRRSLG] (SEQ ID NO:3)) are added. The reaction is incubated for 75 min (ambient temperature) and stopped by the addition of 180 μL of 6.4% trichloroacetic acid and incubated for 20 min on ice. A multiscreen filtration plate (Millipore, MAIP NOB10) is equilibrated first of all with 100 μL 70% ethanol and then with 180 μL trichloroacetic acid and the liquids are eliminated using a suitable suction apparatus. Then the stopped kinase reaction is applied. After 5 washing steps with 180 μL 1% trichloroacetic acid in each case the lower half of the dish is dried (10-20 min at 55° C.) and 25 μL scintillation cocktail (Microscint, Packard #6013611) is added. Incorporated gamma-phosphate is quantified using a Wallac 1450 Micro-beta Liquid Scintillation Counter. Samples without test substance or without substrate peptide are used as controls. $IC_{50}$ values are obtained using Graph Pad Prism software.

The anti-proliferative activity of the compounds according to the invention is determined in the proliferation test on cultivated human tumour cells and/or in a cell cycle analysis, for example on NCI-H460 tumour cells. In both test methods compounds 1-147 exhibit good to very good activity, i.e. for example an EC50 value in the NCI-H460 proliferation test of less than 5 μmol/L, generally less than 1 μmol/L.

Measurement of the Inhibition of Proliferation on Cultivated Human Tumour Cells

To measure proliferation on cultivated human tumour cells, cells of lung tumour cell line NCI-H460 (obtained from American Type Culture Collection (ATCC)) are cultivated in RPMI 1640 medium (Gibco) and 10% foetal calf serum (Gibco) and harvested in the log growth phase. Then the NCI-H460 cells are placed in 96-well flat-bottomed plates (Falcon) at a density of 1000 cells per well in RPMI 1640 medium and incubated overnight in an incubator (at 37° C. and 5% $CO_2$). The active substances are added to the cells in various concentrations (dissolved in DMSO; DMSO final concentration: 0.1%). After 72 hours incubation 20 μl AlamarBlue reagent (AccuMed International) is added to each well, and the cells are incubated for a further 5-7 hours. After incubation the colour change of the AlamarBlue reagent is determined in a Wallac Microbeta fluorescence spectrophotometer. $EC_{50}$ values are calculated using Standard Levenburg Marquard algorithms (GraphPadPrizm).

Cell cycle analyses are carried out for example using FACS analyses (Fluorescence Activated Cell Sorter) or by Cellomics Array Scan (CellCycle Analysis).

FACS Analysis

Propidium iodide (PI) binds stoichiometrically to double-stranded DNA, and is thus suitable for determining the proportion of cells in the G1, S, and G2/M phase of the cell cycle on the basis of the cellular DNA content. Cells in the G0 and G1 phase have a diploid DNA content (2N), whereas cells in the G2 or mitosis phase have a 4N DNA content.

For PI staining, for example, $1.75 \times 10^6$ NCI-H460 cells are seeded onto a 75 $cm^2$ cell culture flask, and after 24 h either 0.1% DMSO is added as control or the substance is added in various concentrations (in 0.1% DMSO). The cells are incubated for 42 h with the substance or with DMSO. Then the cells are detached with trypsin and centrifuged. The cell pellet is washed with buffered saline solution (PBS) and the cells are then fixed with 80% at −20° C. for at least 2 h. After another washing step with PBS the cells are permeabilised with Triton X-100 (Sigma; 0.25% in PBS) on ice for 5 min, and then incubated with a solution of propidium iodide (Sigma; 10 μg/ml) and RNAse (Serva; 1 mg/mL1) in the ratio 9:1 for at least 20 min in the dark.

The DNA measurement is carried out in a Becton Dickinson FACS Analyzer, with an argon laser (500 mW, emission 488 nm); data are obtained and evaluated using the DNA Cell Quest Programme (BD).

Cellomics Array Scan

NCI-H460 cells are seeded into 96-well flat-bottomed dishes (Falcon) in RPMI 1640 medium (Gibco) with 10% foetal calf serum (Gibco) in a density of 2000 cells per well and incubated overnight in an incubator (at 37° C. and 5% $CO_2$). The active substances are added to the cells in various concentrations (dissolved in DMSO; DMSO final concentration: 0.1%). After 42 h incubation the medium is suction filtered, the cells are fixed for 10 min with 4% formaldehyde solution and Triton X-100 (1:200 in PBS) at ambient temperature and simultaneously permeabilised, and then washed twice with a 0.3% BSA solution (Calbiochem). Then the DNA is stained by the addition of 50 μL/well of 4',6-diamidino-2-phenylindole (DAPI; Molecular Probes) in a final concentration of 300 nM for 1 h at ambient temperature, in the dark. The preparations are then carefully washed twice with PBS, the plates are stuck down with black adhesive film and analysed in the Cellomics ArrayScan using the CellCycle BioApplication programme and visualised and evaluated using Spotfire.

The substances of the present invention are Aurora kinase inhibitors. On the basis of their biological properties the compounds of general formula (I) according to the invention, their isomers and the physiologically acceptable salts thereof are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy).

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, giant cell tumour, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortinsone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib cetuximab (Erbitux®) and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions, —particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. EtOH or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) Tablets | per tablet |
|---|---|
| active substance according to formula (1) | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) Tablets | per tablet |
|---|---|
| active substance according to formula (1) | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance according to formula (1) | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

What is claimed is:

1. A compound of formula (1),

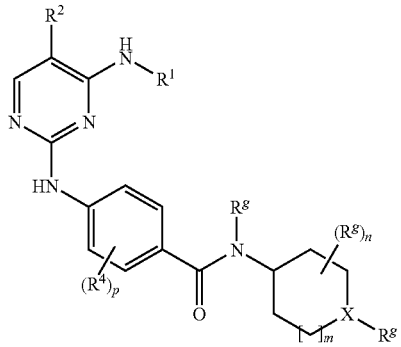

(1)

wherein

X denotes N or CH, and $R^1$ denotes $C_{3-10}$cycloalkyl, substituted by $R^3$ and optionally by one or more $R^4$, and $R^2$ denotes a group selected from among hydrogen, halogen, —CN, —NO$_2$, $C_{1-4}$alkyl, $C_{1-4}$haloalkyl, $C_{3-10}$cycloalkyl, $C_{4-16}$cycloalkylalkyl and $C_{7-16}$arylalkyl, and $R^3$ denotes a suitable group selected from among —C(O)$R^c$, —C(O)O$R^c$, —C(O)N$R^cR^c$, —S(O)$_2R^c$, —N(R$^f$)S(O)$_2R^c$, —N(R$^f$)C(O)$R^c$, —N(R$^f$)C(O)O$R^c$, and —N(R$^f$)C(O)N$R^cR^c$, and $R^4$ denotes a group selected from among $R^a$, $R^b$ and $R^a$ substituted by one or more identical or different $R^c$ and/or $R^b$, and each $R^a$ independently of one another is selected from among $C_{1-6}$alkyl, $C_{3-10}$cycloalkyl, $C_{4-16}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each $R^b$ denotes a suitable group and each is independently selected from among =O, —O$R^c$, $C_{1-3}$haloalkyloxy, —OCF$_3$, =S, —S$R^c$, =N$R^c$, =NO$R^c$, —N$R^cR^c$, halogen, —CF$_3$, —CN, —NC, —OCN, —SCN, —NO$_2$, —S(O)$R^c$, —S(O)$_2R^c$, —S(O)$_2$O$R^c$, —S(O)N$R^cR^c$, —S(O)$_2$N$R^cR^c$, —OS(O)$R^c$, —OS(O)$_2R^c$, —OS(O)$_2$O$R^c$, —OS(O)$_2$N$R^cR^c$, —C(O)$R^c$, —C(O)O$R^c$, —C(O)N$R^cR^c$, —CN(R$^f$)N$R^cR^c$, —CN(OH)$R^c$, —CN(OH)N$R^cR^c$, —OC(O)$R^c$, —OC(O)O$R^c$, —OC(O)N$R^cR^c$, —OCN(R$^f$)N$R^cR^c$, —N(R$^f$)C(O)$R^c$, —N(R$^f$)C(S)$R^c$, —N(R$^f$)S(O)$_2R^c$, —N(R$^f$)C(O)O$R^c$, —N(R$^f$)C(O)N$R^cR^c$, —[N(R$^f$)C(O)]$_2R^c$, —N[C(O)]$_2R^c$, —N[C(O)]$_2$O$R^c$, —[N(R$^f$)C(O)]$_2$O$R^c$ and —N(R$^f$)CN(R$^f$)N$R^cR^c$, and each R$^c$ independently of one another denotes hydrogen or a group optionally substituted by one or more identical or different R$^d$ and/or R$^e$ selected from among C$_{1-6}$alkyl, C$_{3-10}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each R$^d$ independently of one another denotes hydrogen or a group optionally substituted by one or more identical or different R$^e$ and/or R$^f$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each R$^e$ is a suitable group, each independently selected from among =O, —OR$^f$, C$_{1-3}$haloalkyloxy, —OCF$_3$, =S, —SR$^f$, =NR$^f$, =NOR$^f$, —NR$^f$R$^f$, halogen, —CF$_3$, —CN, —NC, —OCN, —SCN, —NO$_2$, —S(O)R$^f$, —S(O)$_2$R$^f$, —S(O)$_2$OR$^f$, —S(O)NR$^f$R$^f$, —S(O)$_2$NR$^f$R$^f$, —OS(O)R$^f$, —OS(O)$_2$R$^f$, —OS(O)$_2$OR$^f$, —OS(O)$_2$NR$^f$R$^f$, —C(O)R$^f$, —C(O)OR$^f$, —C(O)NR$^f$R$^f$, —CN(R$^g$)NR$^f$R$^f$, —CN(OH)R$^f$, —C(NOH)NR$^f$R$^f$, —OC(O)R$^f$, —OC(O)OR$^f$, —OC(O)NR$^f$R$^f$, —OCN(R$^g$)NR$^f$R$^f$, —N(R$^g$)C(O)R$^f$, —N(R$^g$)C(S)R$^f$, —N(R$^g$)S(O)$_2$R$^f$, —N(R$^d$)C(O)OR$^f$, —N(R$^g$)C(O)NR$^f$R$^f$, and —N(R$^g$)CN(R$^f$)NR$^f$R$^f$, and each R$^f$ independently of one another denotes hydrogen or a group optionally substituted by one or more identical or different R$^g$ selected from among C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkylalkyl, 5-12 membered heteroaryl and 6-18 membered heteroarylalkyl, and each R$^g$ independently of one another denotes hydrogen, C$_{1-6}$alkyl, C$_{3-8}$cycloalkyl, C$_{4-11}$cycloalkylalkyl, C$_{6-10}$aryl, C$_{7-16}$arylalkyl, 2-6 membered heteroalkyl, 3-8 membered heterocycloalkyl, 4-14 membered heterocycloalkyl, 5-12 membered heteroaryl and 6-18 membered heteroarylalkyl, and m denotes 0 or 1, and n denotes 0, 1, 2, 3 or 4, and p denotes 0, 1 or 2, optionally in the form of the tautomers, the racemates, the enantiomers, the diastereomers and the mixtures thereof, and optionally the pharmacologically acceptable acid addition salts thereof, with the proviso that the following compounds 4-[4-((1R,2S)-2-isopropylcarbamoyl-cyclopentylamino)-5-trifluoromethyl-pyrimidin-2-ylamino]-N-(1-methyl-piperidin-4-yl)-benzamide, 4-[4-((1R,2S)-2-isopropylcarbamoyl-cyclopentylamino)-5-trifluoromethyl-pyrimidin-2-ylamino]-N-piperidin-4-yl-benzamide, 2-fluoro-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide, 2-chloro-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide, 2-fluoro-4-[4-((1R,2S)-2-isopropylcarbamoyl-cyclopentylamino)-5-trifluoromethyl-pyrimidin-2-ylamino]-N-methyl-N-(1-methyl-piperidin-4-yl)-benzamide 4-[4-((1R,2S)-2-carbamoyl-cyclopentylamino)-5-methyl-pyrimidin-2-ylamino]-N-(1-methyl-piperidin-4-yl)-benzamide, 4-[4-((1R,2S)-2-carbamoyl-cyclopentylamino)-5-nitro-pyrimidin-2-ylamino]-N-(1-methyl-piperidin-4-yl)-benzamide, 4-[4-((1R,2S)-2-carbamoyl-cyclopentylamino)-5-fluoro-pyrimidin-2-ylamino]-N-(1-methyl-piperidin-4-yl)-benzamide, 4-[4-((1R,2S)-2-carbamoyl-cyclopentylamino)-5-chloro-pyrimidin-2-ylamino]-N-(1-methyl-piperidin-4-yl)-benzamide, 4-[4-((1R,2S)-2-carbamoyl-cyclopentylamino)-5-isopropyl-pyrimidin-2-ylamino]-N-(1-methyl-piperidin-4-yl)-benzamide, 4-[5-bromo-4-((1R,2S)-2-carbamoyl-cyclopentylamino)-pyrimidin-2-ylamino]-N-(1-methyl-piperidin-4-yl)-benzamide, 4-[4-((1R,2S)-2-carbamoyl-cyclopentylamino)-5-iodo-pyrimidin-2-ylamino]-N-(1-methyl-piperidin-4-yl)-benzamide, N-methyl-N-(1-methyl-piperidin-4-yl)-4-{4-[(1R,2S)-2-(pyrrolidine-1-carbonyl)-cyclopentylamino]-5-trifluoromethyl-pyrimidin-2-ylamino}-benzamide, 4-[4-((1R,2S)-2-cyclopentylcarbamoyl-cyclopentylamino)-5-trifluoromethyl-pyrimidin-2-ylamino]-N-methyl-N-(1-methyl-piperidin-4-yl)-benzamide, 4-{4-[(1R,2S)-2-(1,1-dioxo-tetrahydro-1λ$^6$-thiophen-3-ylcarbamoyl)-cyclopentylamino]-5-trifluoromethyl-pyrimidin-2-ylamino}-N-methyl-N-(1-methyl-piperidin-4-yl)-benzamide, N-methyl-N-(1-methyl-piperidin-4-yl)-4-{4-[(1R,2S)-2-(2,2,2-trifluoro-ethylcarbamoyl)-cyclopentylamino]-5-trifluoromethyl-pyrimidin-2-ylamino}-benzamide, N-methyl-4-{4-[(1R,2S)-2-(3-methyl-butylcarbamoyl)-cyclopentylamino]-5-trifluoromethyl-pyrimidin-2-ylamino}-N-(1-methyl-piperidin-4-yl)-benzamide, 4-{4-[(1R,2S)-2-(3-dimethylamino-propylcarbamoyl)-cyclopentylamino]-5-trifluoromethyl-pyrimidin-2-ylamino}-N-methyl-N-(1-methyl-piperidin-4-yl)-benzamide, 4-{4-[(1R,2S)-2-(azetidine-1-carbonyl)-cyclopentylamino]-5-trifluoromethyl-pyrimidin-2-ylamino}-N-methyl-N-(1-methyl-piperidin-4-yl)-benzamide, N-methyl-4-{4-[(1R,2S)-2-(4-methyl-piperidine-1-carbonyl)-cyclopentylamino]-5-trifluoromethyl-pyrimidin-2-ylamino}-N-(1-methyl-piperidin-4-yl)-benzamide, 4-[4-((1R,3S)-3-carbamoyl-cyclopentylamino)-5-trifluoromethyl-pyrimidin-2-ylamino]-N-methyl-N-(1-methyl-piperidin-4-yl)-benzamide, 4-[4-((1S,3R)-3-carbamoyl-cyclopentylamino)-5-trifluoromethyl-pyrimidin-2-ylamino]-N-methyl-N-(1-methyl-piperidin-4-yl)-benzamide, 4-[4-((1R,2S)-2-carbamoyl-cyclopentylamino)-5-cyano-pyrimidin-2-ylamino]-N-(1-methyl-piperidin-4-yl)-benzamide 4-[4-((1R,2S)-2-carbamoyl-cyclopentylamino)-5-phenylethynyl-pyrimidin-2-ylamino]-N-(1-methyl-piperidin-4-yl)-benzamide and 4-[4-((1R,2S)-2-carbamoyl-cyclopentylamino)-5-cyclopropyl-pyrimidin-2-ylamino]-N-(1-methyl-piperidin-4-yl)-benzamide are not included.

2. The compound according to claim 1, wherein X denotes N.

3. The compound according to claim 1, wherein m is equal to 1.

4. The compounds according to claim 1, wherein R$^2$ denotes a group selected from among halogen and C$_{1-4}$haloalkyl.

5. The compound according to claim 4, wherein R$^2$ denotes —CF$_3$.

6. The compound according to claim 1, wherein $R^1$ denotes $C_{4-6}$cycloalkyl.

7. The compound according to claim 6, wherein $R^1$ denotes cyclopentyl.

8. A composition of matter comprising a compound according to claim 1 and one or more pharmaceutically acceptable carries or excipients.

9. A pharmaceutical composition comprising a compound according of claim 1 and at least one other cytostatic or cytotoxic active substance different from said compound.

10. A compound according to claim 1 selected from among:

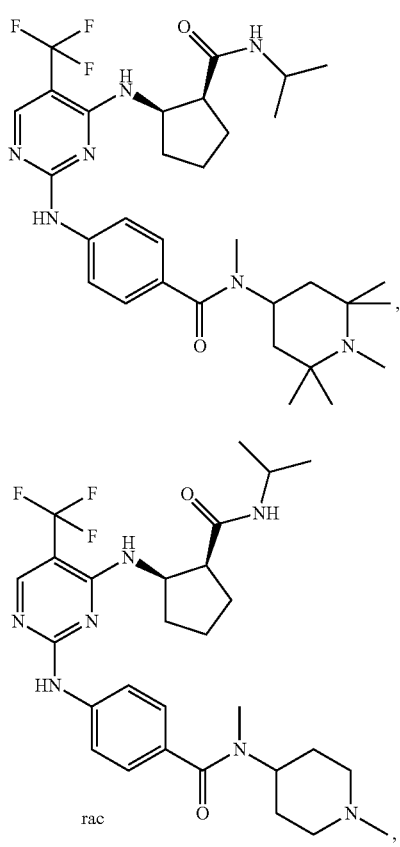

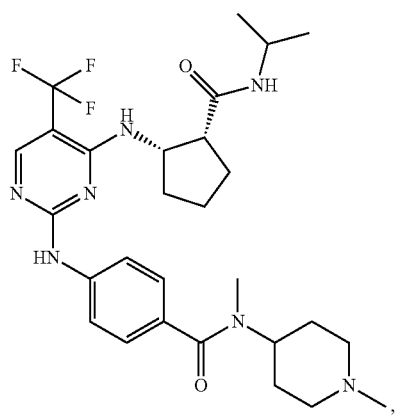

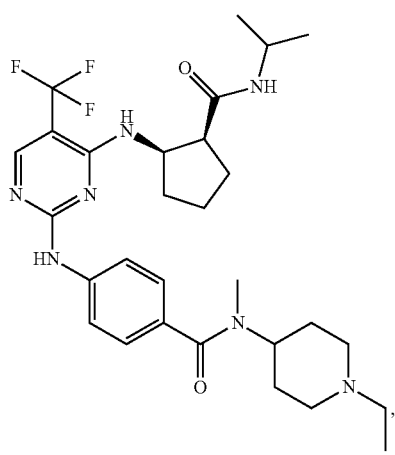

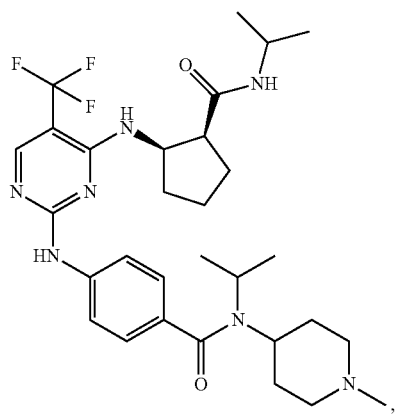

7
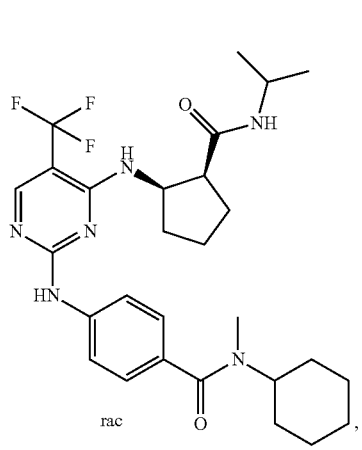
rac
8
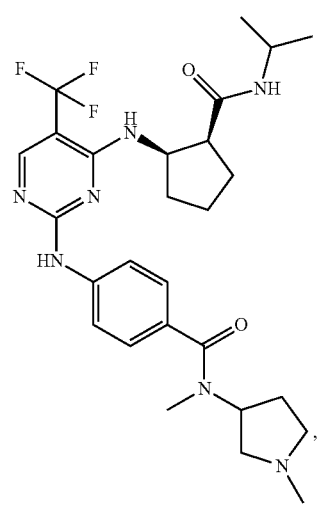
9
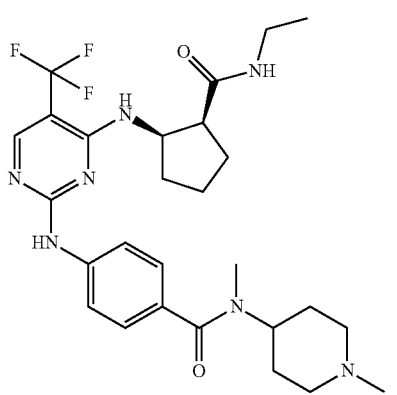
5
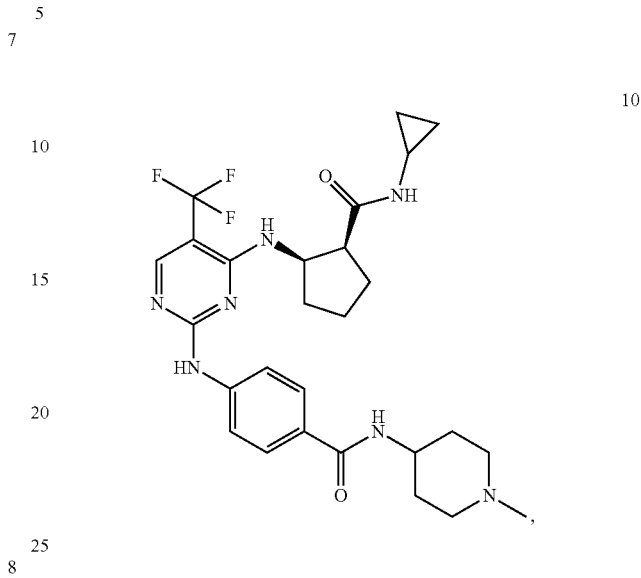
12
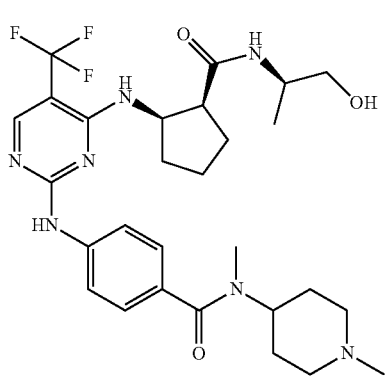
13
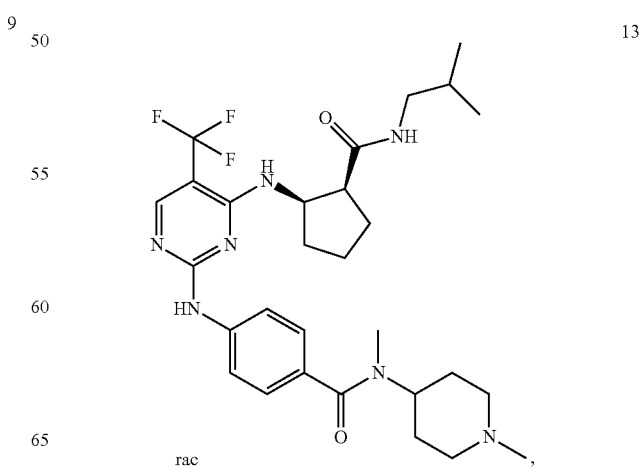
rac 14
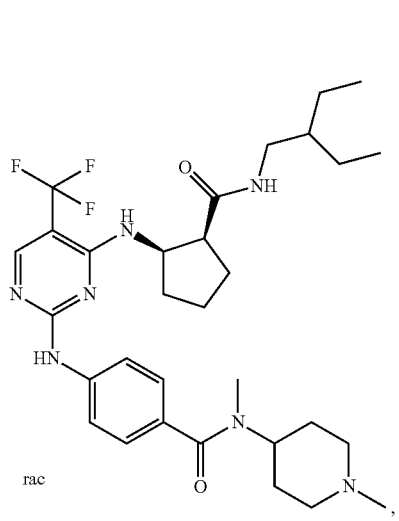
rac
15
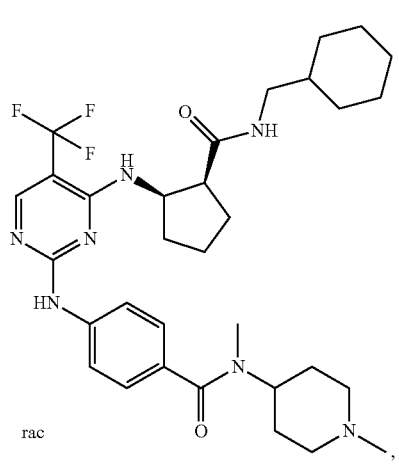
rac
17
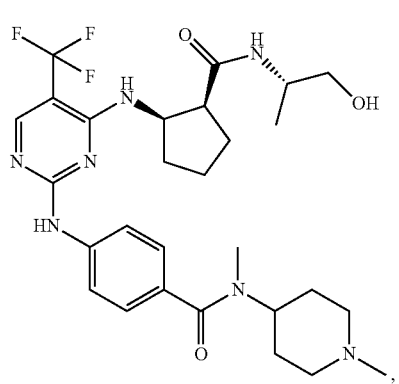
18
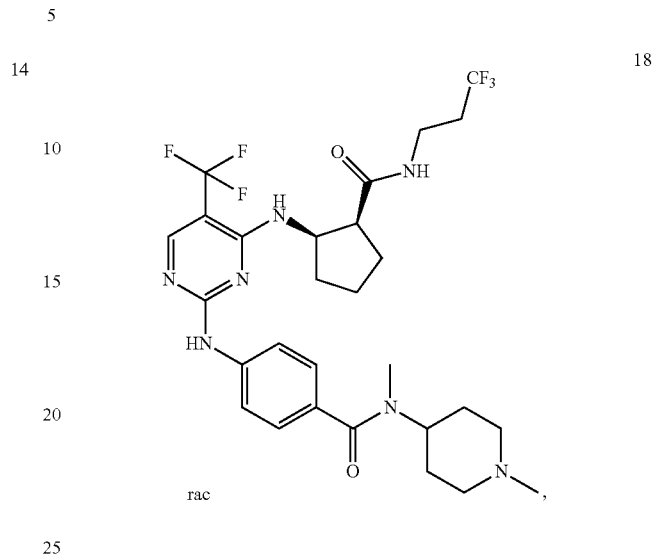
rac
19
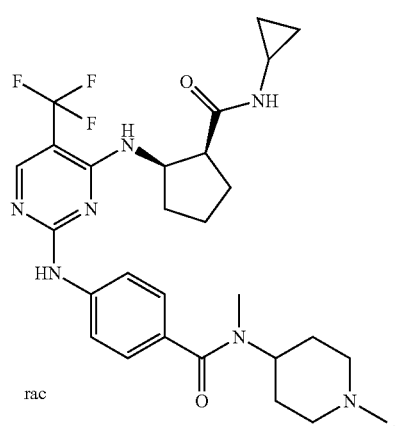
rac
20
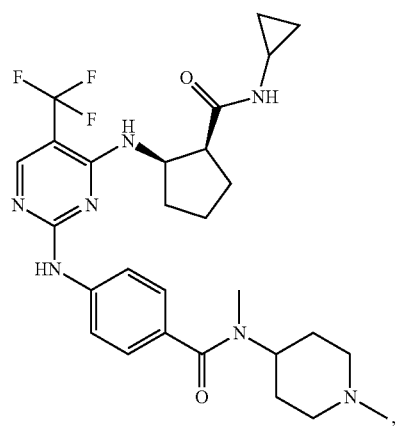

21 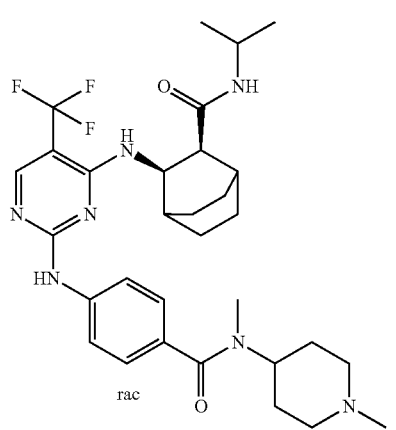
22 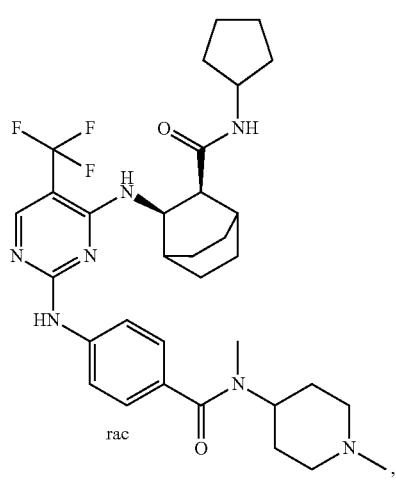
23 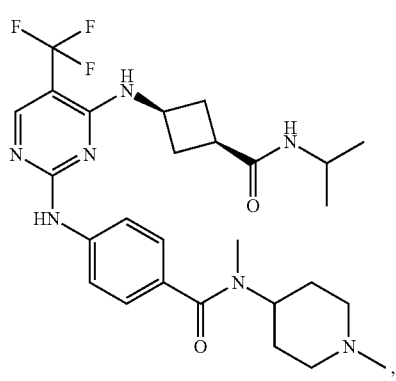
24 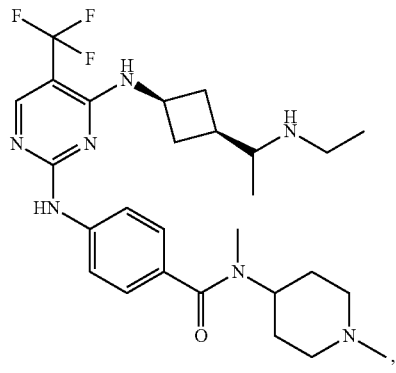
25 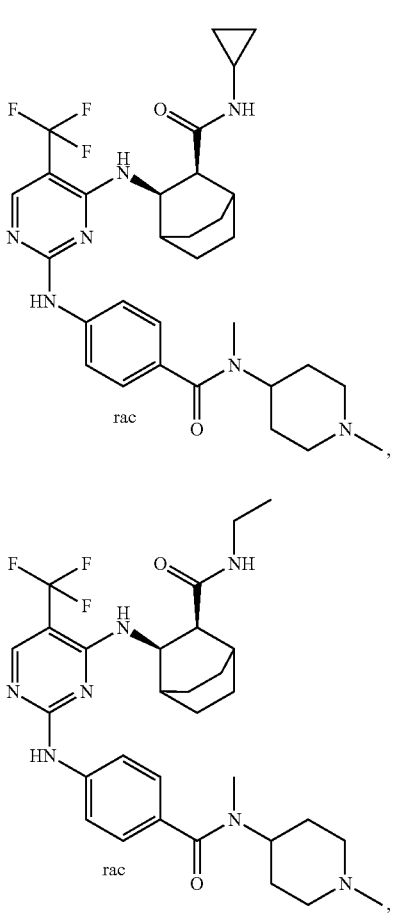
27 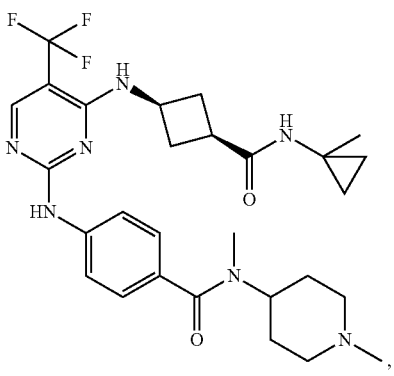
28 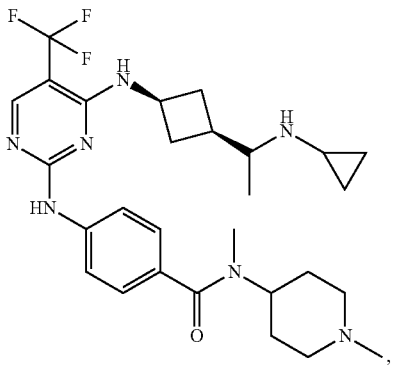

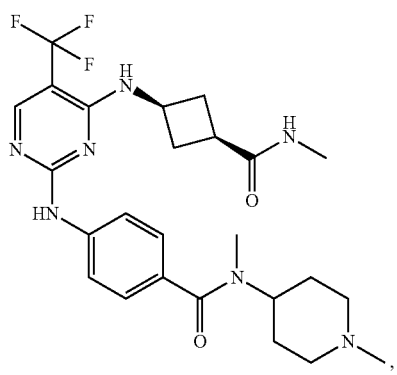
29
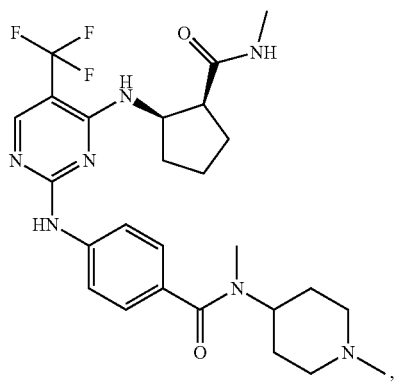
30
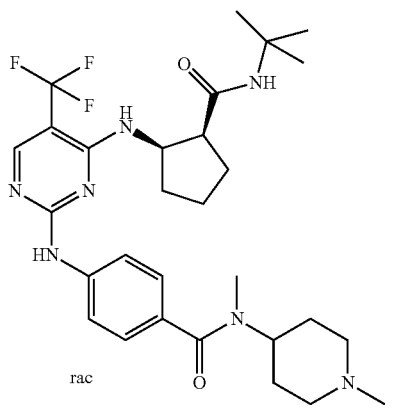
31
rac
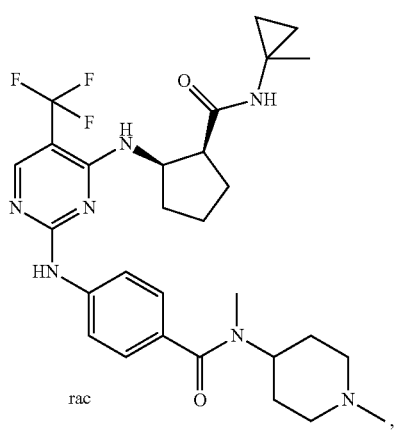
32
rac
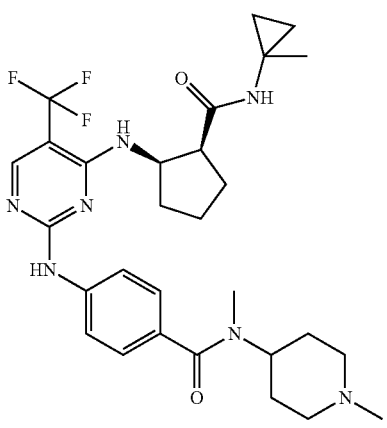
33
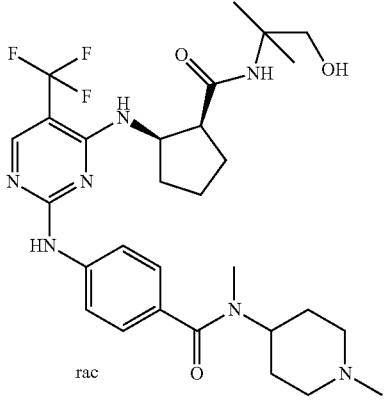
34
rac
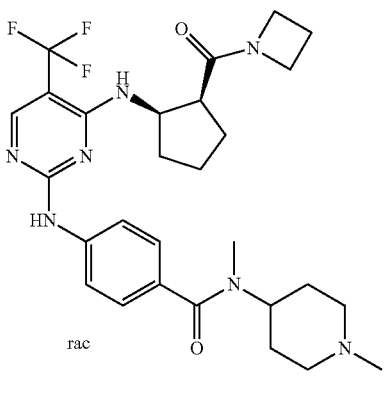
35
rac
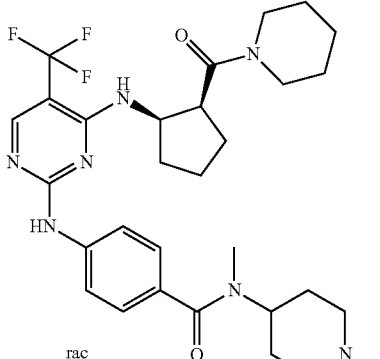
37
rac

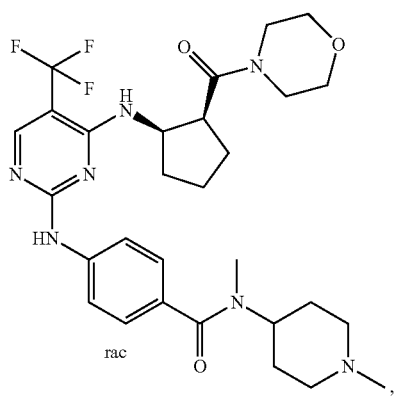
39
rac
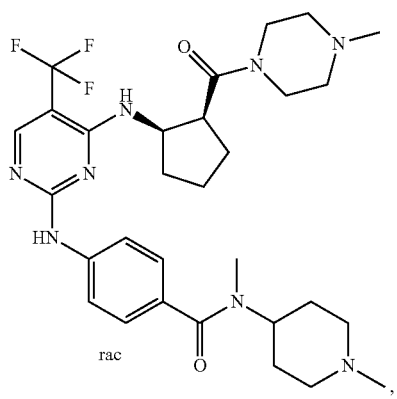
40
rac
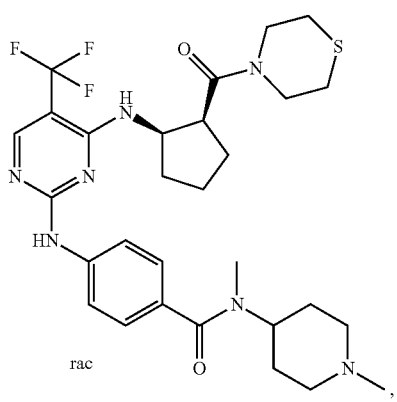
41
rac
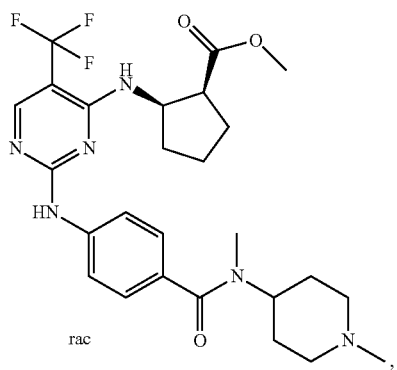
42
rac
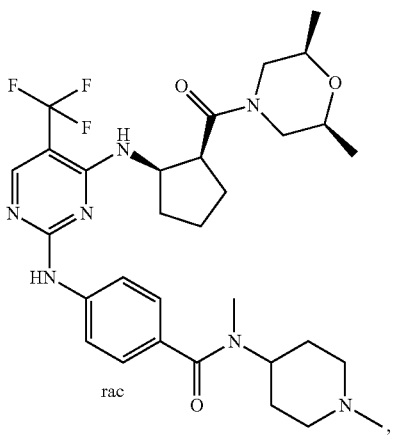
43
rac
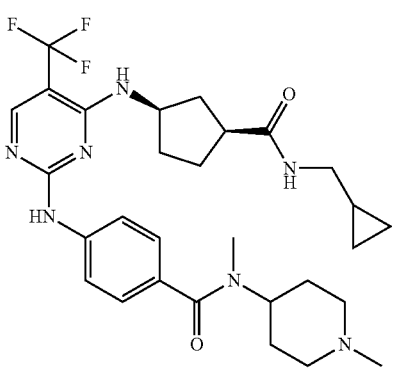
44
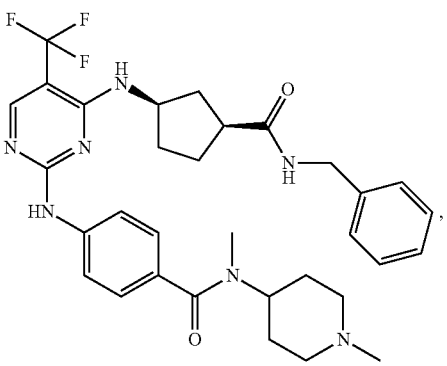
45
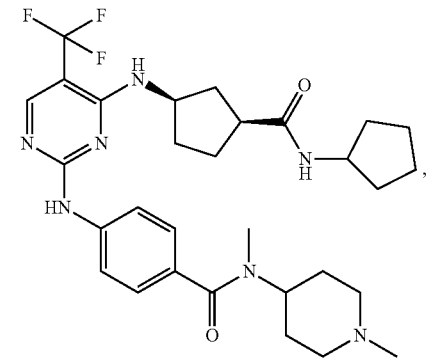
46

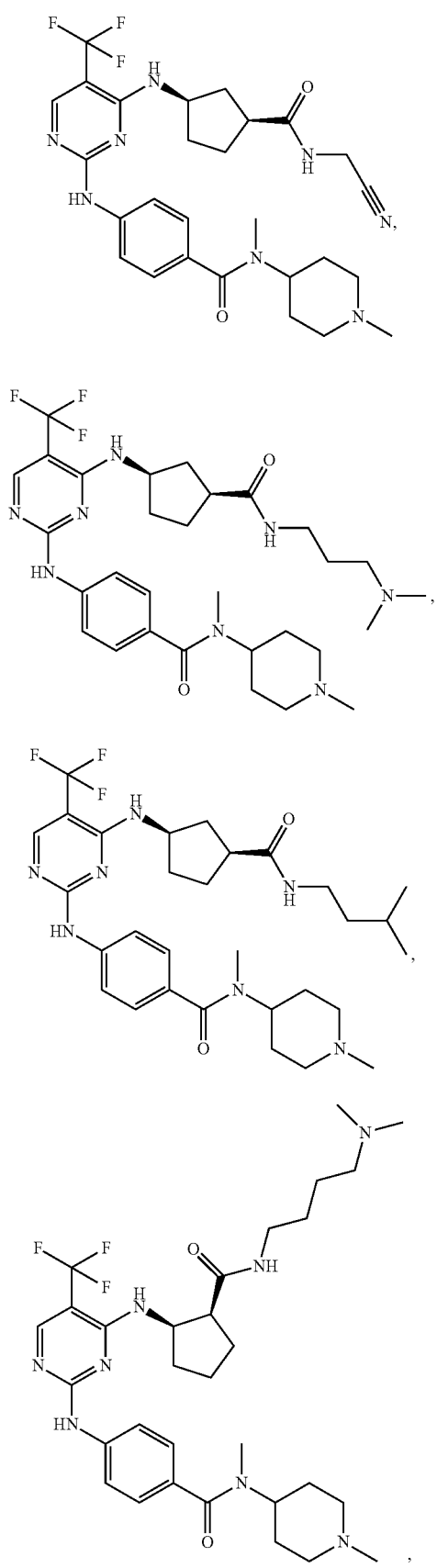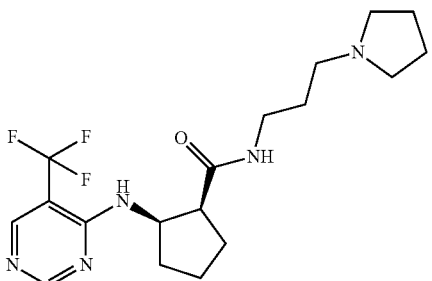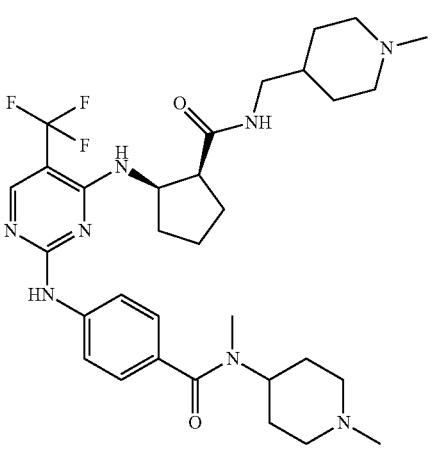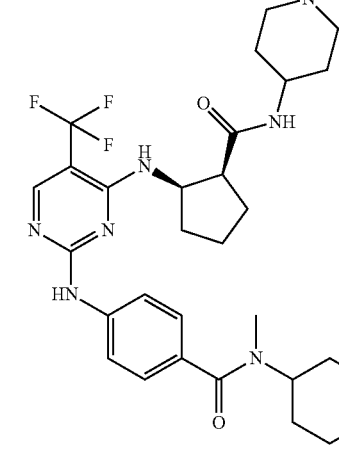

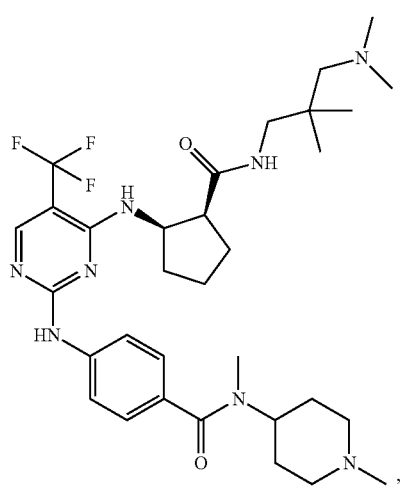
54
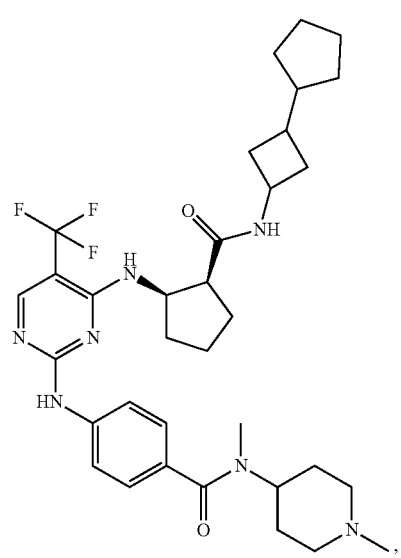
55
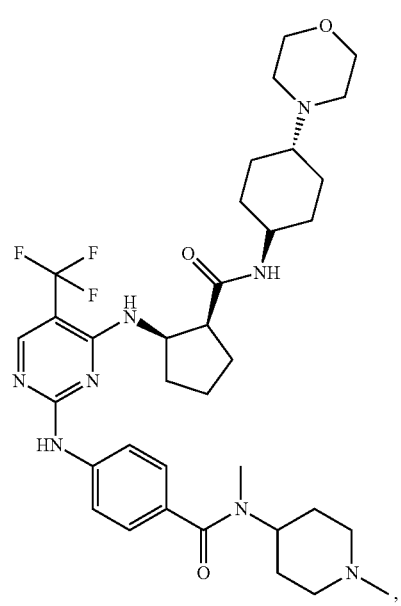
56
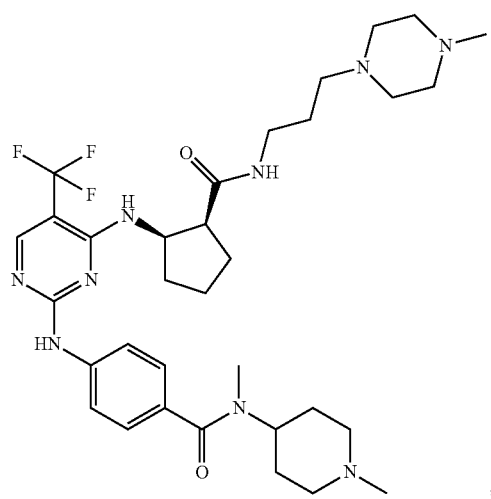
57
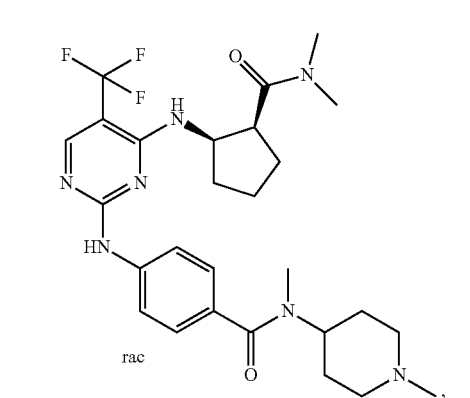
58
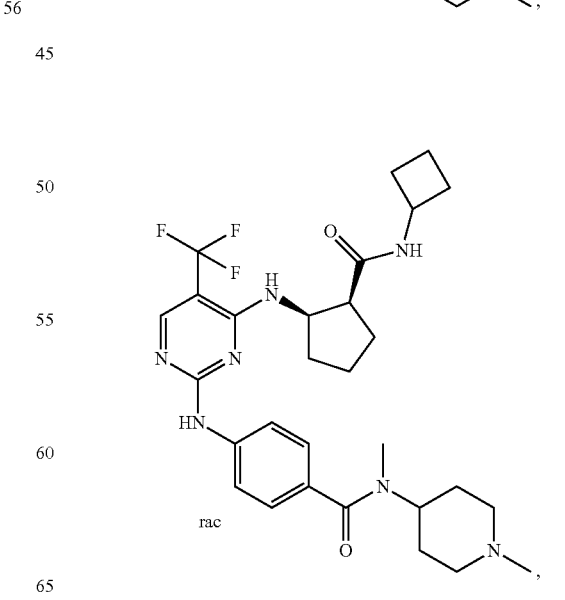
59

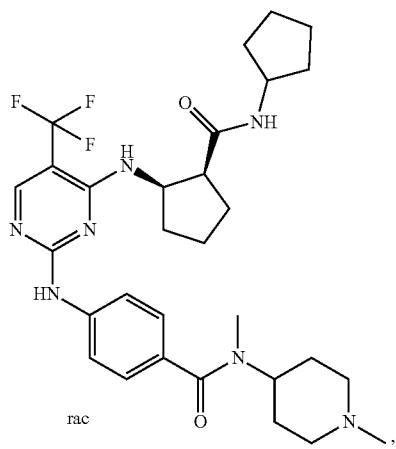
60
rac
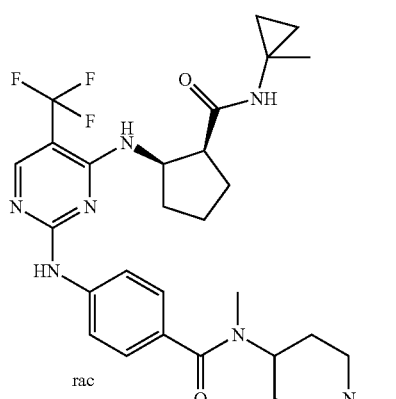
61
rac
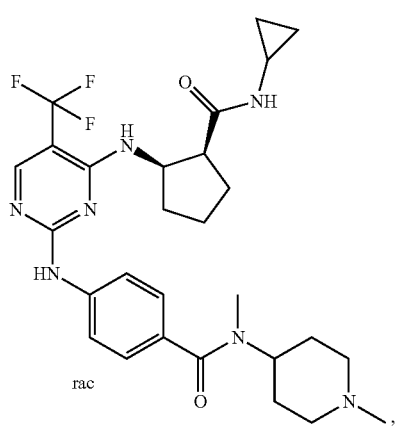
62
rac
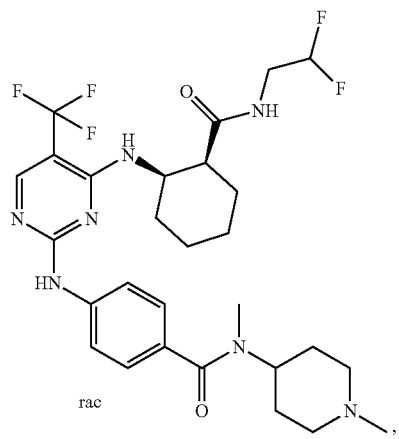
63
rac
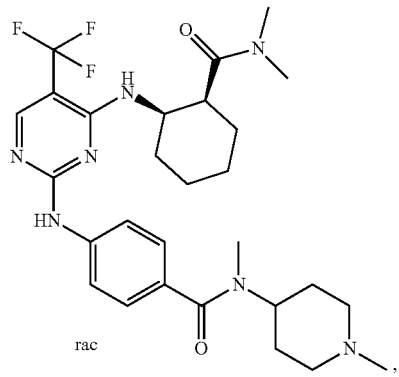
64
rac
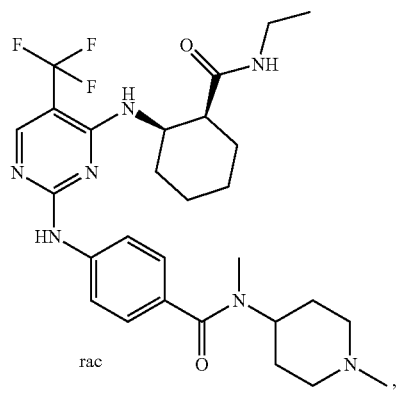
65
rac
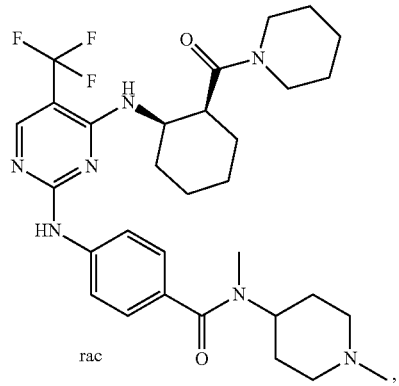
66
rac

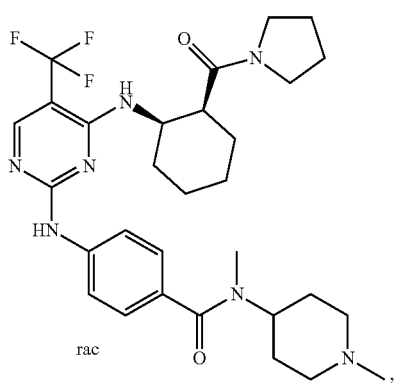
67
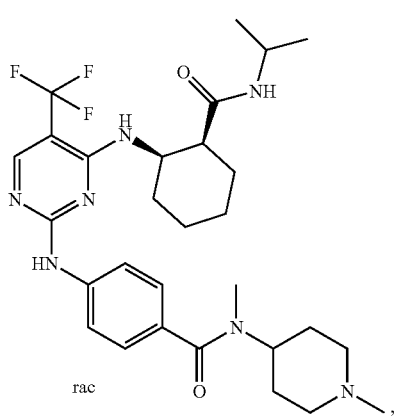
68
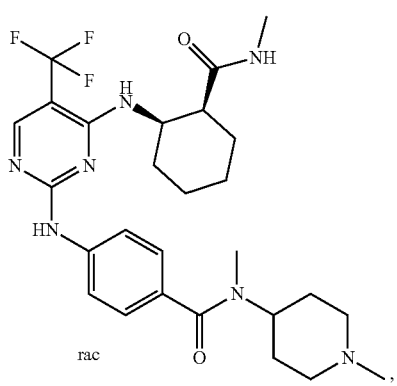
69
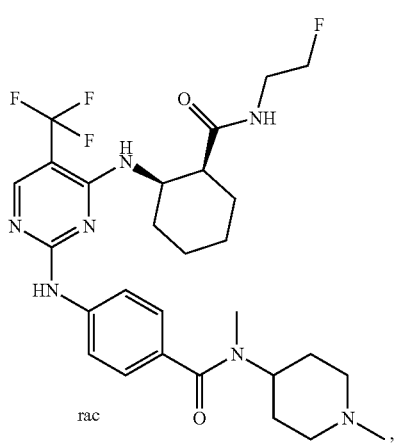
70
71
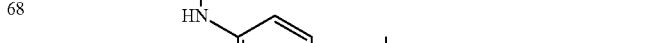
72
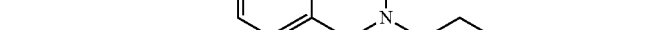
75

76 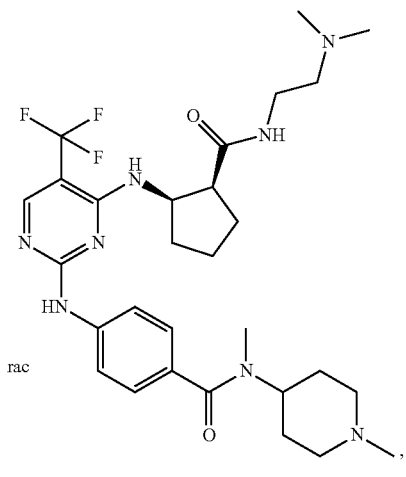 rac
77 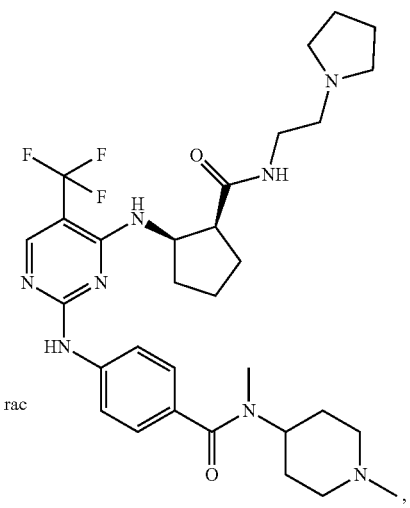 rac
79 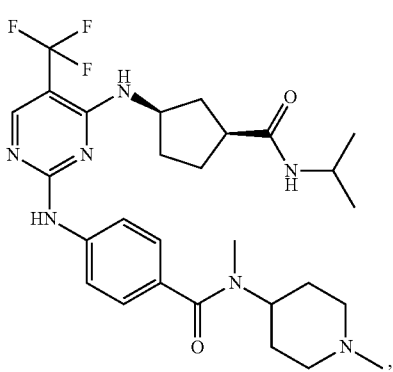
80 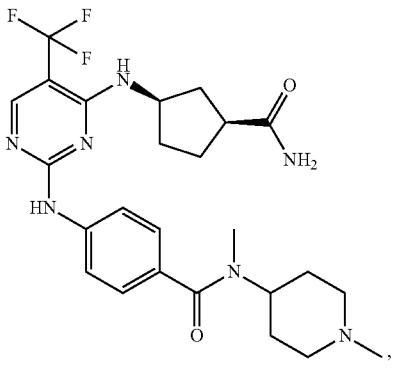
81 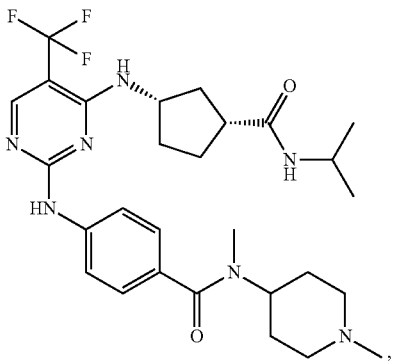
82 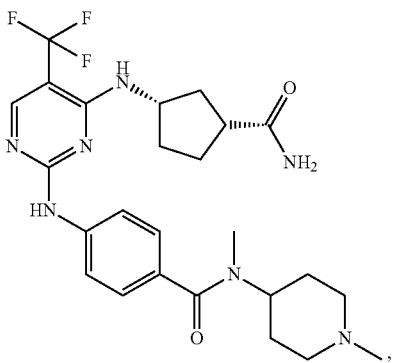
83 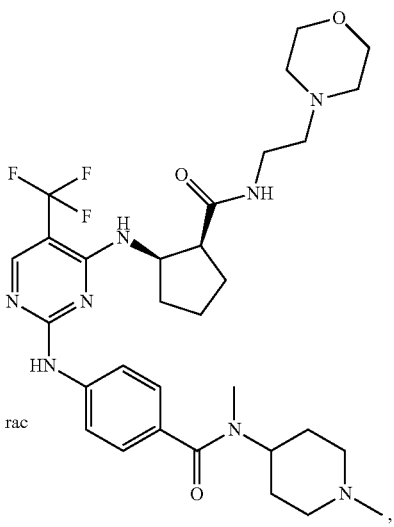 rac

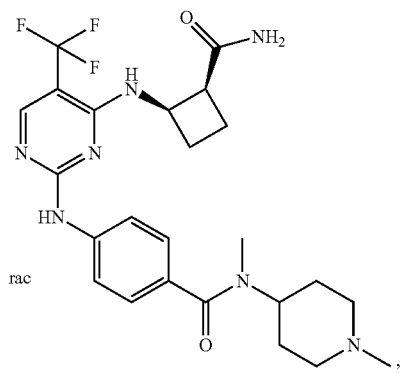
84
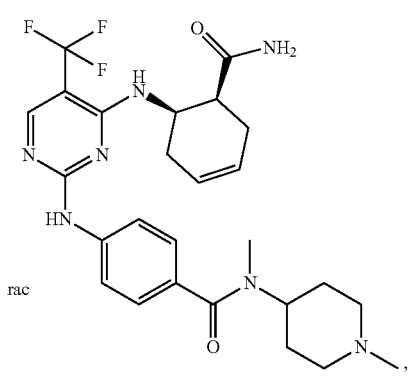
85
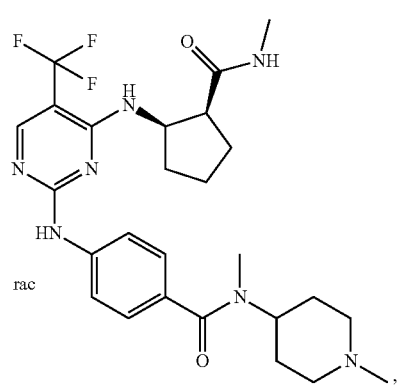
86
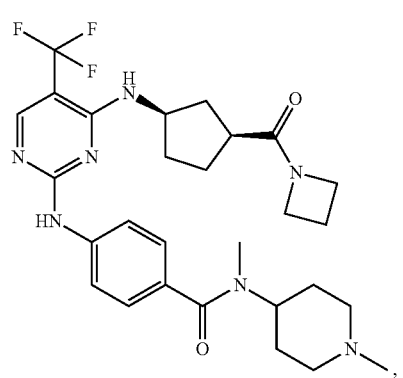
87
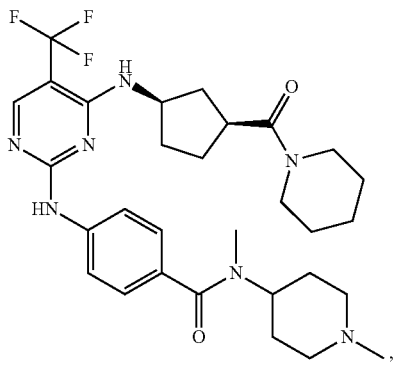
88
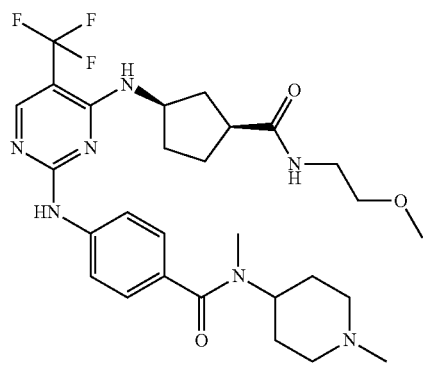
89
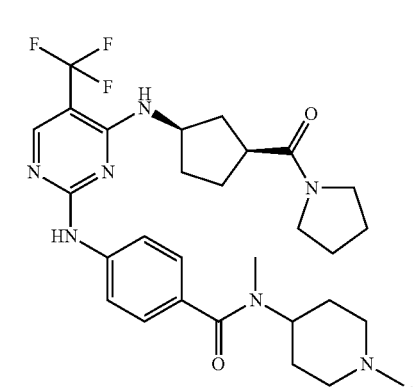
90
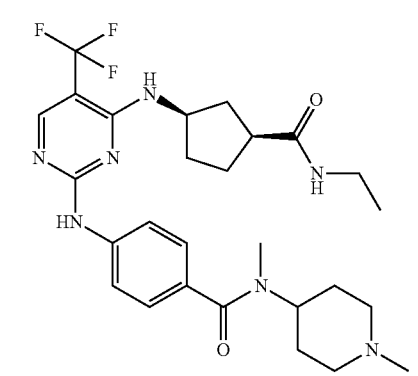
91

92 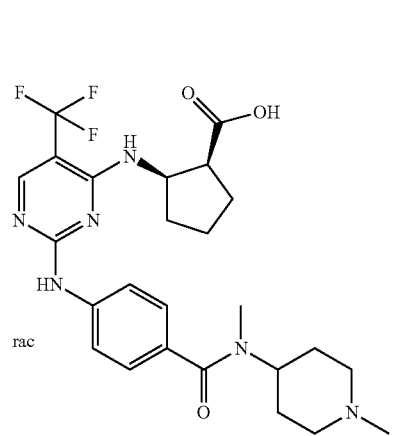
93 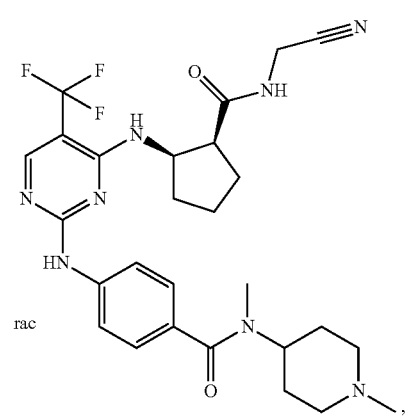
94 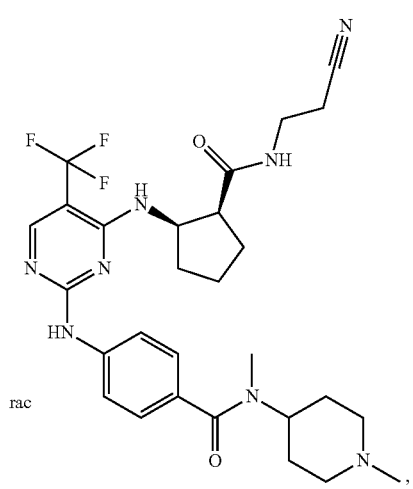
95 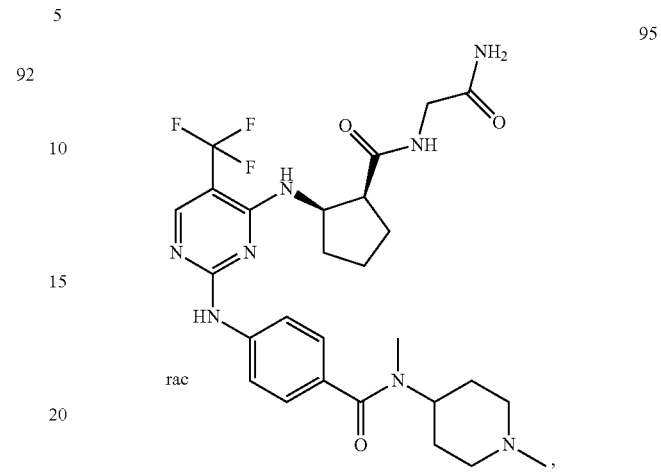
96 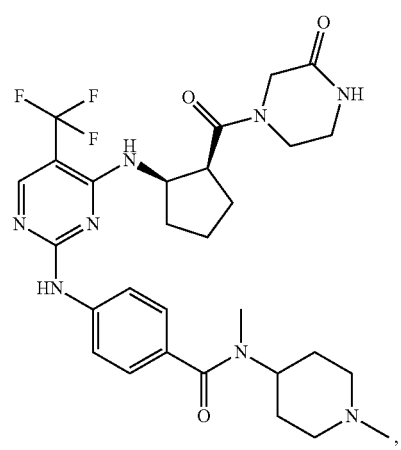
97 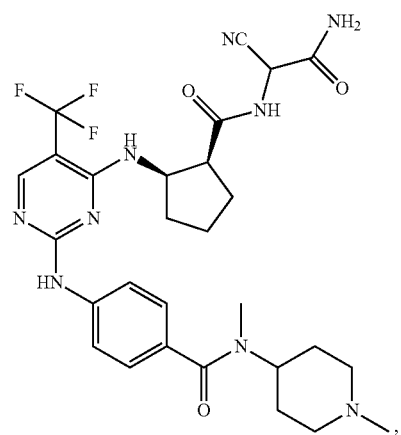

163
-continued
98
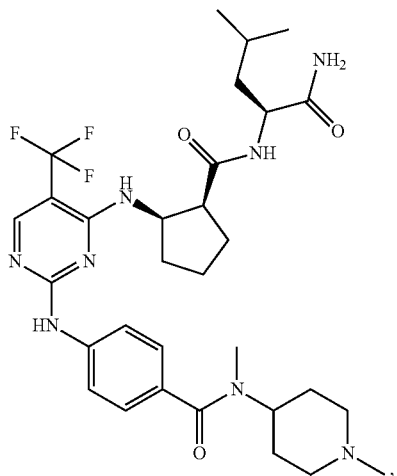
99
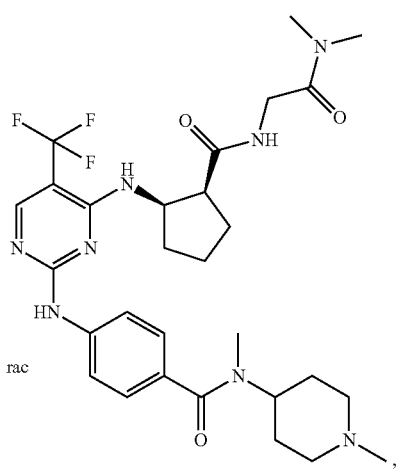
rac
100
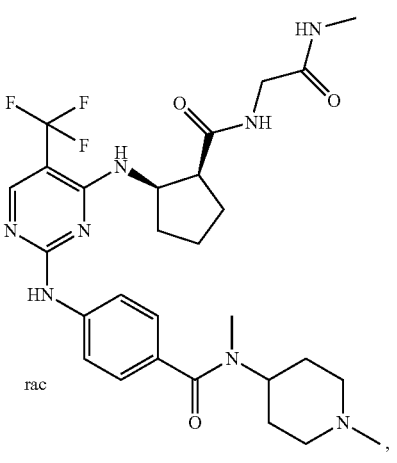
rac
164
-continued
101
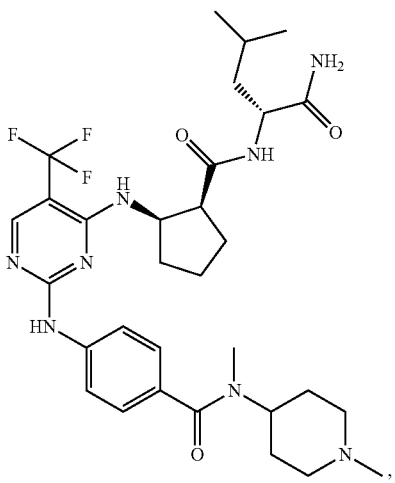
102
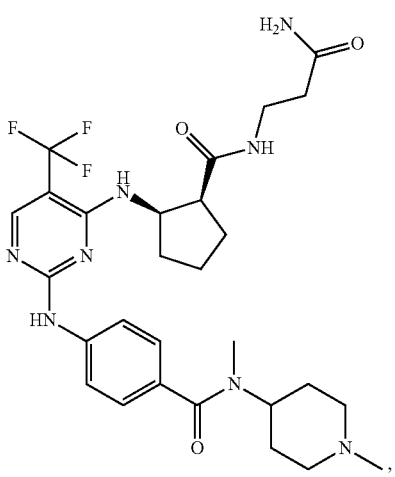
103
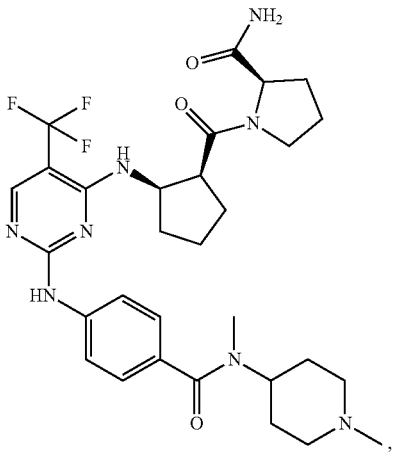

104 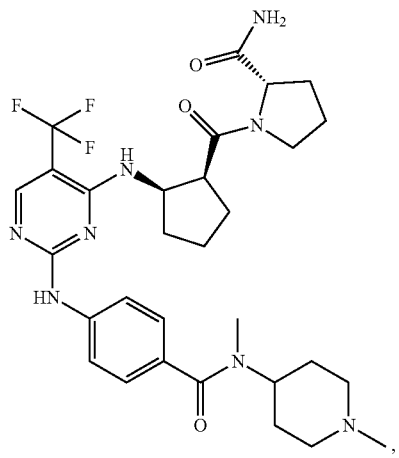
105 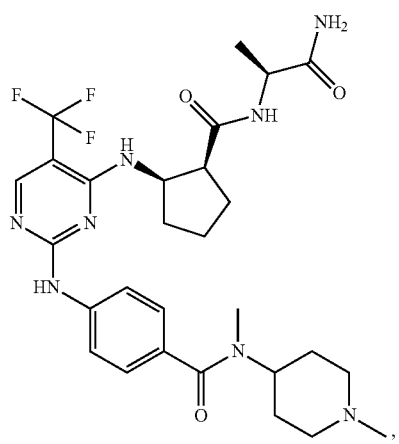
106 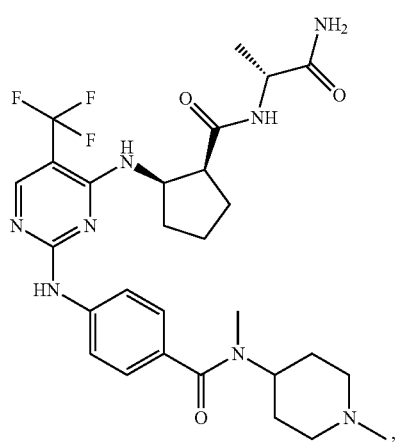
107 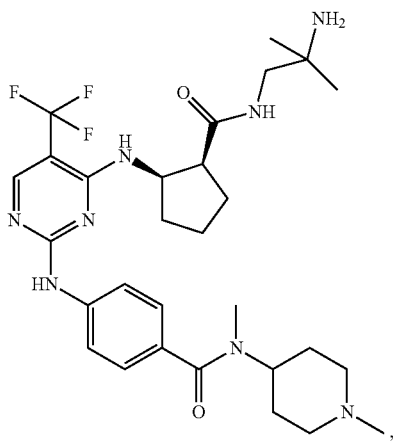
108 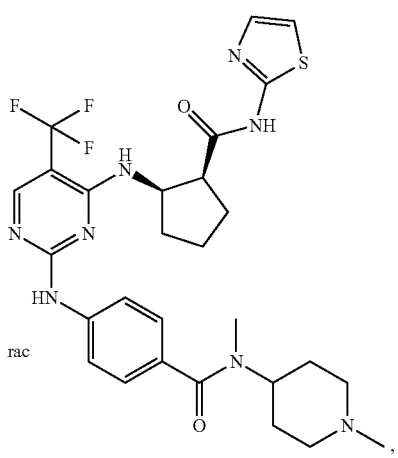
rac
109 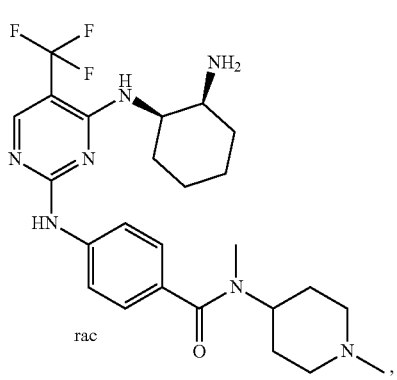
rac
110 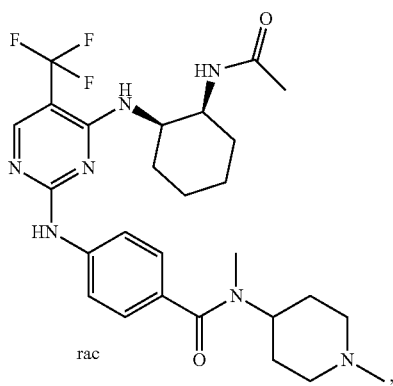
rac

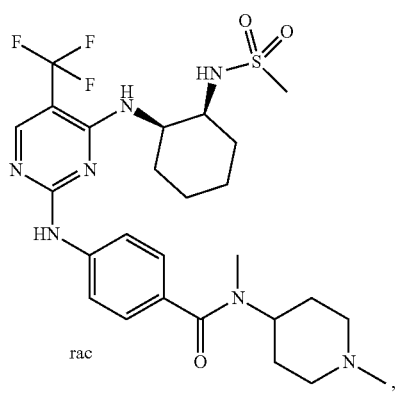
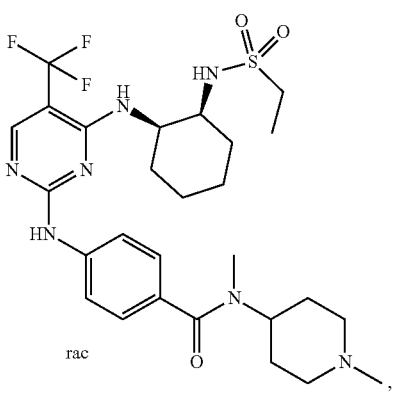
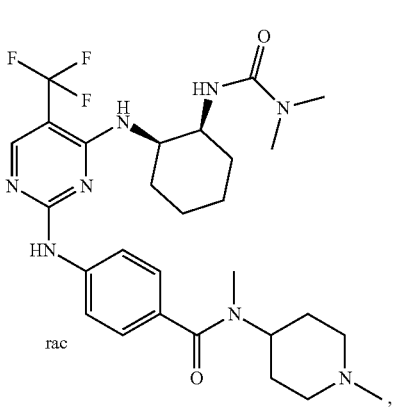
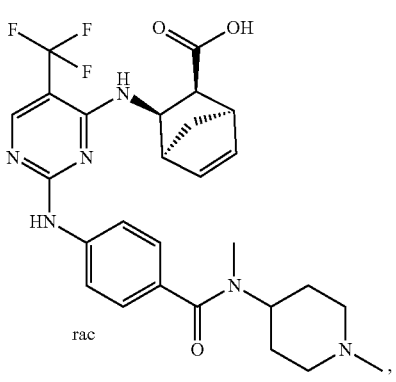
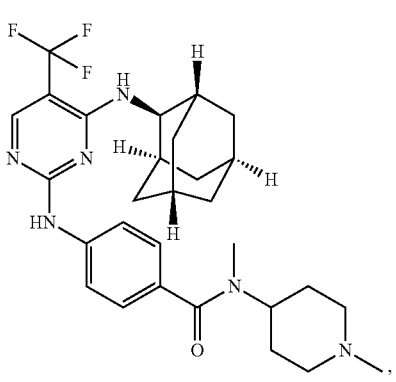

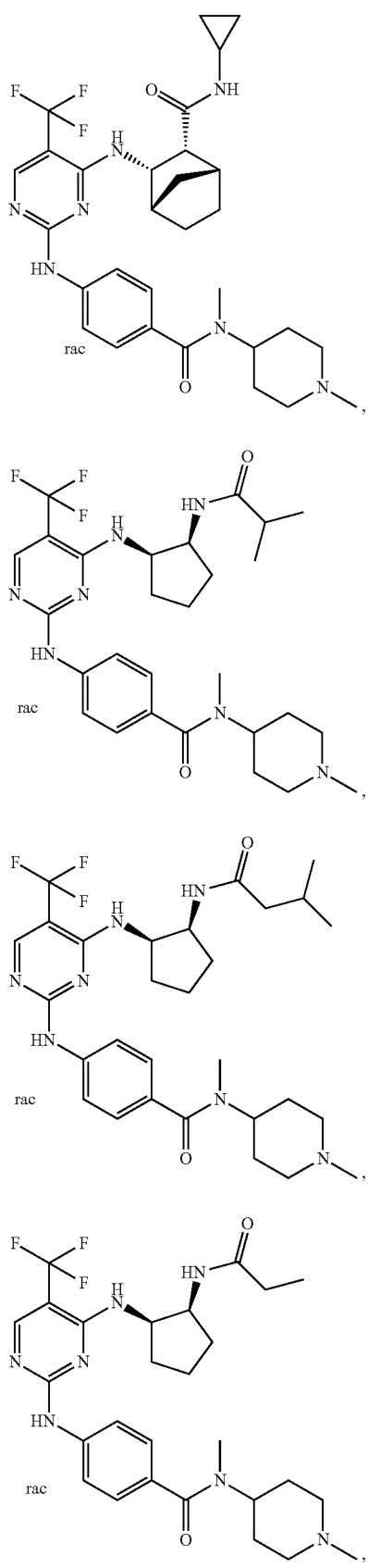
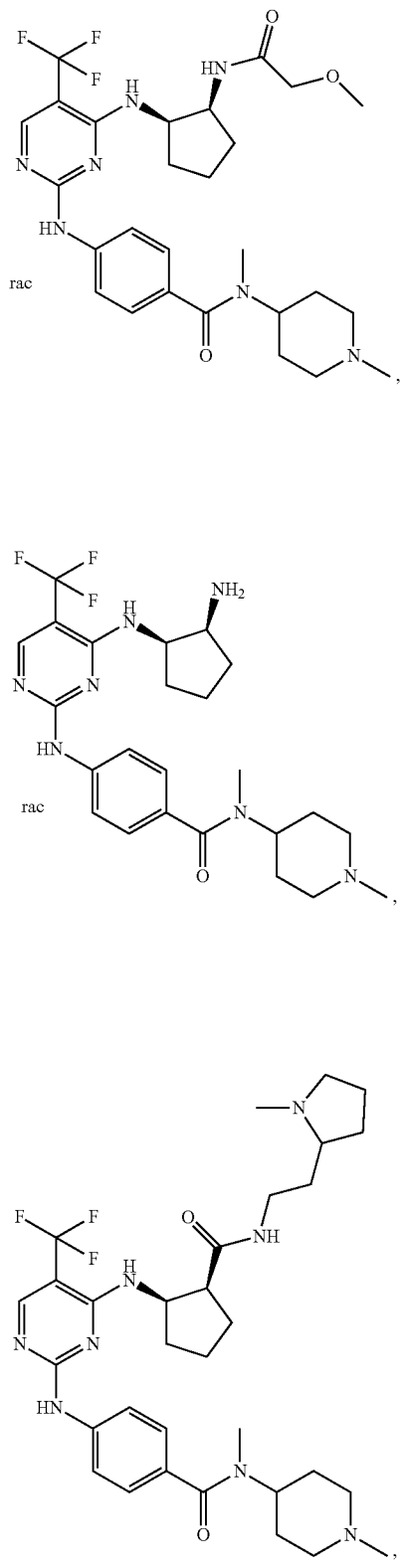

126
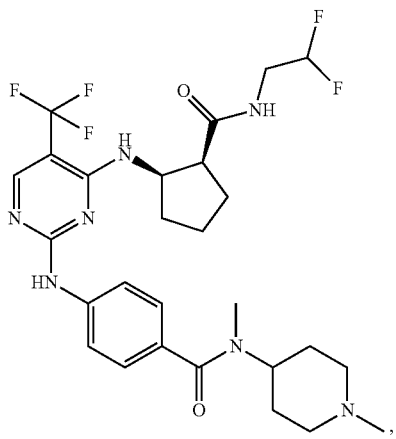
127
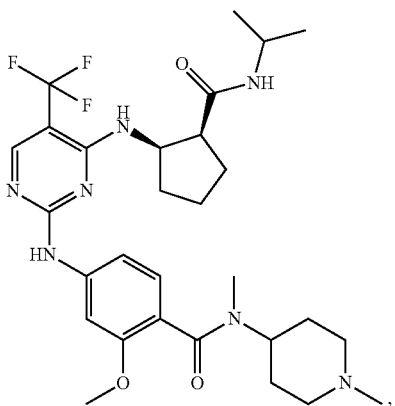
128
129
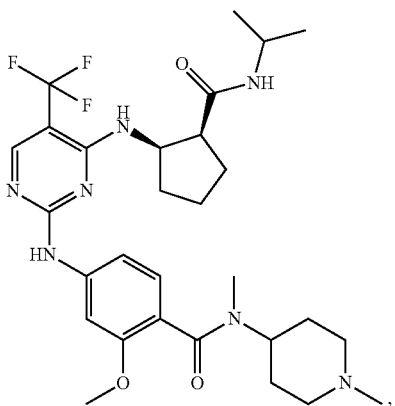
130
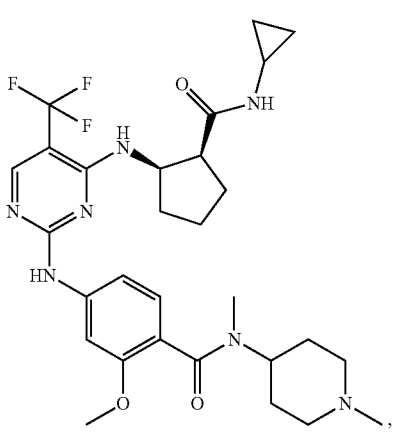
131
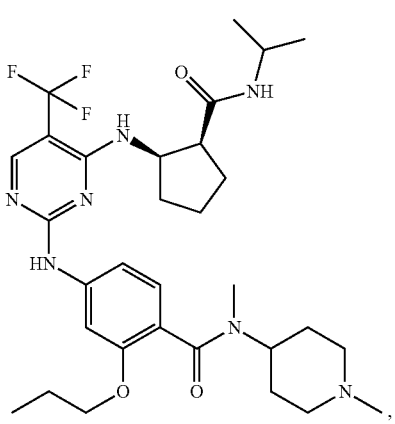
132
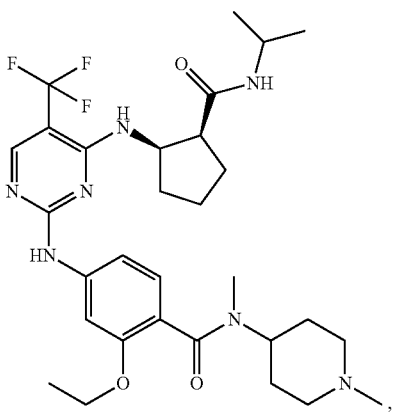

173
-continued
134
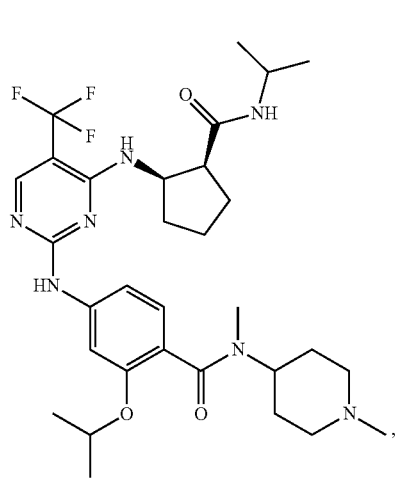
136
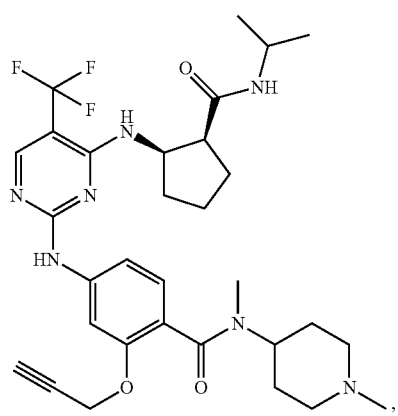
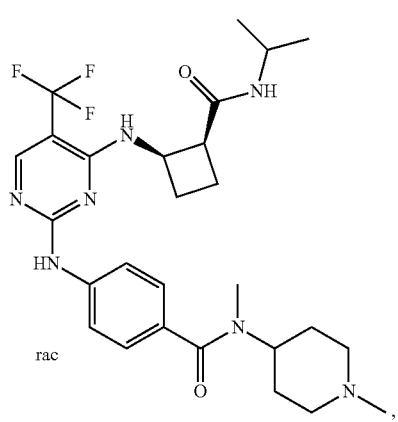
174
-continued
133
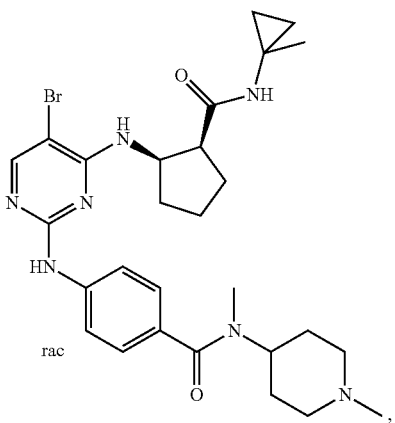
137
138
139
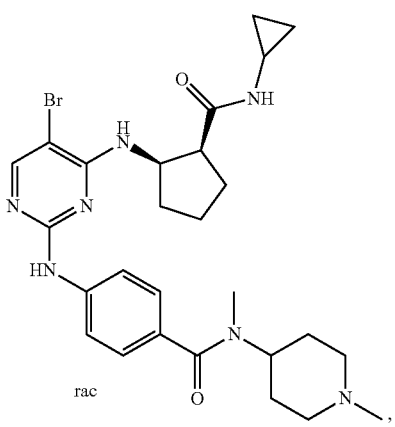

140
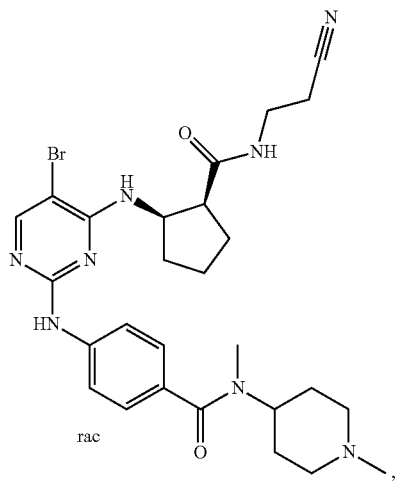
rac
141
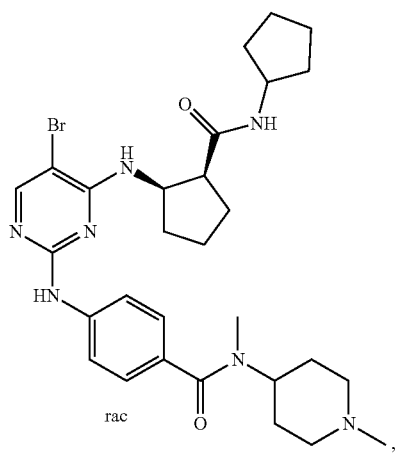
rac
142
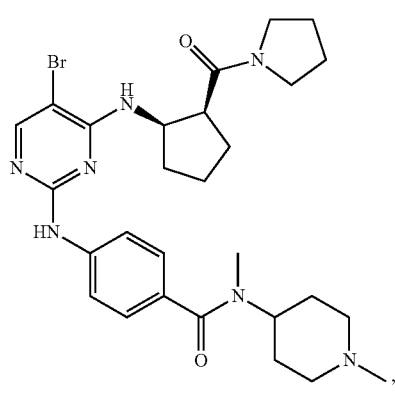
143
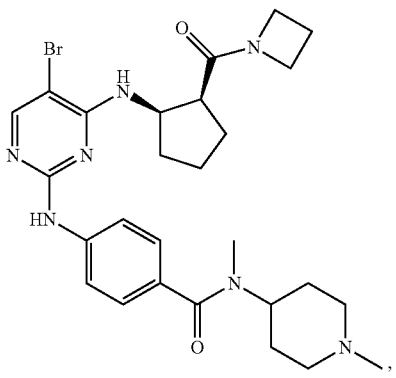
144
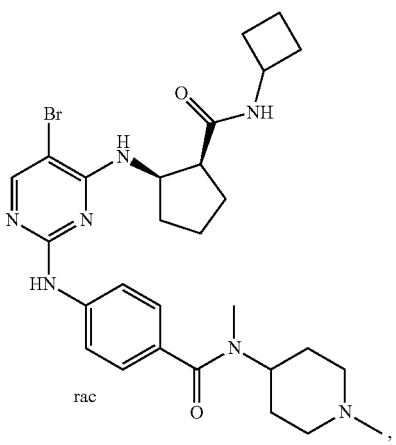
rac
145
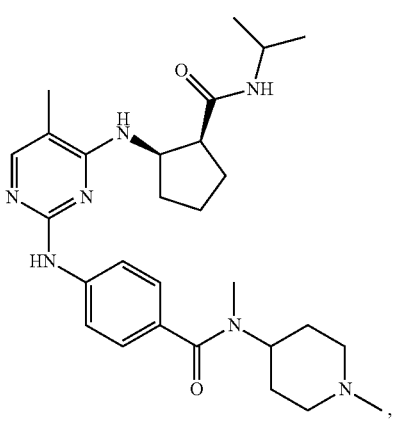
146
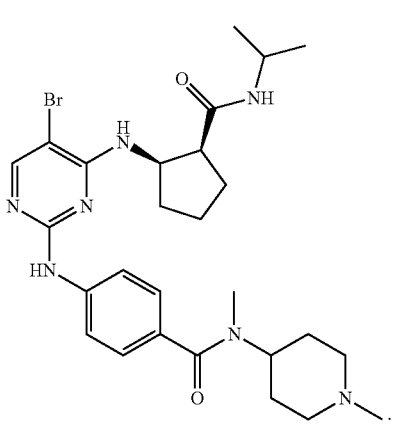

-continued

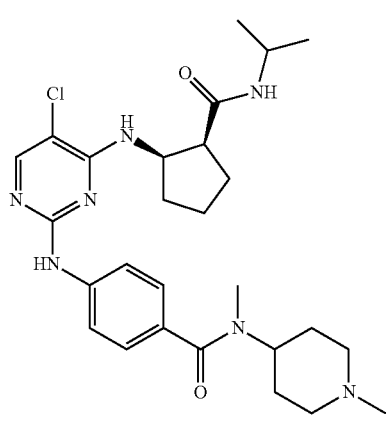

and a pharmaceutically acceptable salt of any of the foregoing.

11. A compound of the formula

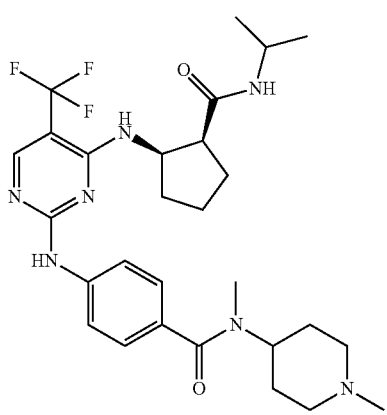

or a pharmaceutically acceptable salt thereof.

12. A compound of the formula

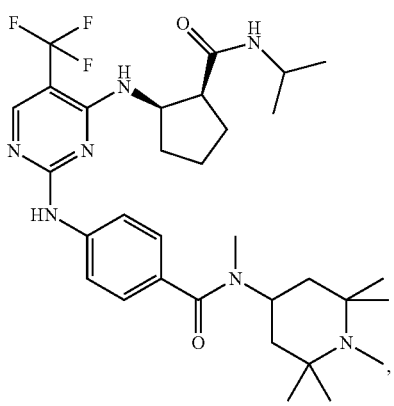

or a pharmaceutically acceptable salt thereof.

13. A compound of the formula

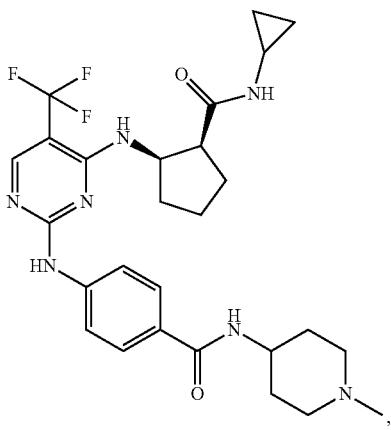

or a pharmaceutically acceptable salt thereof.

14. A compound of the formula

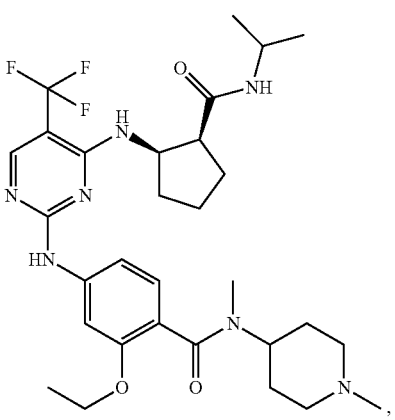

or a pharmaceutically acceptable salt thereof.

15. A compound of the formula

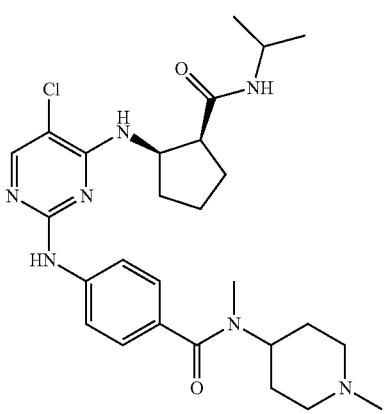

or a pharmaceutically acceptable salt thereof.

* * * * *